US011872324B2

(12) United States Patent
Salmeron-Sanchez et al.

(10) Patent No.: US 11,872,324 B2
(45) Date of Patent: Jan. 16, 2024

(54) MATERIALS AND METHODS FOR TISSUE REGENERATION

(71) Applicants: The University Court of the University of Glasgow, Glasgow (GB); Georgia Tech Research Corporation, Atlanta, GA (US)

(72) Inventors: Manuel Salmeron-Sanchez, Glasgow (GB); Matthew J. Dalby, Glasgow (GB); Andres J. Garcia, Atlanta, GA (US)

(73) Assignees: The University Court of the University of Glasgow, Glasgow (GB); Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 15/576,718

(22) PCT Filed: May 26, 2016

(86) PCT No.: PCT/EP2016/061925
§ 371 (c)(1),
(2) Date: Nov. 23, 2017

(87) PCT Pub. No.: WO2016/189094
PCT Pub. Date: Dec. 1, 2016

(65) Prior Publication Data
US 2018/0133364 A1     May 17, 2018

(30) Foreign Application Priority Data

May 26, 2015 (GB) ...................... 1508931

(51) Int. Cl.
| | |
|---|---|
| A61L 27/36 | (2006.01) |
| A61L 27/22 | (2006.01) |
| A61L 27/54 | (2006.01) |
| A61K 38/18 | (2006.01) |
| A61L 27/34 | (2006.01) |

(52) U.S. Cl.
CPC ........ *A61L 27/225* (2013.01); *A61K 38/1825* (2013.01); *A61K 38/1841* (2013.01); *A61K 38/1866* (2013.01); *A61K 38/1875* (2013.01); *A61L 27/227* (2013.01); *A61L 27/34* (2013.01); *A61L 27/54* (2013.01); *A61L 2300/414* (2013.01); *A61L 2300/426* (2013.01); *A61L 2400/18* (2013.01)

(58) Field of Classification Search
CPC .......... A61L 27/00; A61L 27/04; A61L 27/06; A61L 27/10; A61L 27/20; A61L 27/28; A61L 27/36; A61L 27/3633
See application file for complete search history.

(56) References Cited

U.S. PATENT DOCUMENTS

| | | | |
|---|---|---|---|
| 4,828,563 A | 5/1989 | Mueller-Lierheim | |
| 5,013,649 A | 5/1991 | Wang | |
| 5,166,058 A | 11/1992 | Wang | |
| 5,618,924 A | 4/1997 | Wang | |
| 5,631,142 A | 5/1997 | Wang | |
| 6,172,872 B1 * | 1/2001 | Katsui .................. | H01L 23/467 361/695 |
| 6,179,872 B1 * | 1/2001 | Bell ....................... | A61L 27/24 428/304.4 |
| 8,815,275 B2 * | 8/2014 | Zhou ...................... | A61F 2/82 424/423 |
| 2007/0274962 A1 | 11/2007 | Lui | |

FOREIGN PATENT DOCUMENTS

WO     2014/161036 A1     10/2014

OTHER PUBLICATIONS

Vanterpool et al., A Material-Based Platform to Modulate Fibronectin Activity and Focal Adhesion Assembly, Bioresearch Open Access, vol. 3, No. 6, Dec. 2014 (Year: 2014).*
Zhu et al., Fibronectin at Select Sites Binds Multiple Growth Factors and Enhances their Activity: Expansion of the Collaborative ECM-GF Paradigm, Journal of Investigative Dermatology, 134, 895-901, 2014 (Year: 2014).*
Tsimbouri, et al. (2012) Using nanotopography and metabolomics to identify biochemical effectors of multipotency. ACS Nano 6(11): 10239-10249.
Dave PC, Dingal P, Discher DE (2014) Combining insoluble and soluble factors to steer stem cell fate. Nat Mater 13(6):532-537.
Martino M M, Hubbell JA (2010) The 12th-14th type III repeats of fibronectin function as a highly promiscuous growth factor-binding domain. FASEB J 24(12):4711-4721.
Martino MM, Tortelli F, Mochizuki M, Traub S, Ben-David D, Kuhn GA, Muller R, Livne Bo E, Eming SA, Hubbell JA (2011) Engineering the growth factor microenvironment with fibronectin domains to promote wound and bone tissue healing. Sci Transl Med 3:100ra89.
Martino MM, Briquez PS, Ranga A, Lutolf MP, Hubbell JA (2013) Heparin-binding domain of fibrin(ogen) binds growth factors and promotes tissue repair when incorporated within a synthetic matrix. Proc Natl A cad Sci USA 110( 12):4563-4568.
Martino MM, Briquez PS, Esra G, Tortelli F, Kilarski WW, Metzger S, Rice JJ, Kuhn GA, Muller R, Swartz MA, Hubbell JA (2014) Growth factors engineered for super-affinity to the extracellular matrix enhance tissue healing. Science 343(6173):885-888.

(Continued)

*Primary Examiner* — Micah Paul Young
(74) *Attorney, Agent, or Firm* — FisherBroyles, LLP; Adelaide Leitzel; Adam Whiting

(57) ABSTRACT

The invention provides materials presenting a biologically active matrix comprising a physiological fibrillar fibronectin network, such as implantable constructs, and their use for modulating cell behaviour and fate, including cell growth, proliferation and/or differentiation, such as for promoting tissue regeneration, for example, bone regeneration or vascularization. Also provided are constructs presenting a biologically active matrix comprising a physiological fibrillar fibronectin network for sustaining growth of stem cells or maintaining stem cells (maintaining stemness).

29 Claims, 39 Drawing Sheets

Specification includes a Sequence Listing.

(56) References Cited

OTHER PUBLICATIONS

Lo KW, Ulery BD, Ashe KM, Laurencin CT (2012) Studies of bone morphogenetic protein-based surgical repair. Adv Drug De/iv Rev 64912):1277-1291.
Woo EJ (2012) Recombinant human bone morphogenetic protein-2: adverse events reported to the manufacturer and user facility device experience database. Spine J 12(10):894-899.
Panel Executive Summary for P050036 Medtronic's Amplify ™ rhBMP-2 Matrix. U. S. Food and Drug Administration, Silver Spring, MD, 2010.
Vo TN, Kasper FK, Mikos AG (2012) Strategies for controlled delivery of growth factors and cells for bone regeneration. Adv Drug Def Rev 64(12):1292-1309.
Lutolf MP, Hubbell JA (2005) Synthetic biomaterials as instructive extracellular microenvironments for morphogenesis in tissue engineering. Nat Biotechnof 23(1 ):47-55.
Wylie RG, Ahsan S, Aizawa Y, Maxwell KL, Morshead CM, Shoichet MS (2011) Spatially controlled simultaneous patterning of multiple growth factors in three-dimensional hydrogels. Nat Mater 10(10):799-806.
Comoglio PM, Boccaccio C, Trusolino L (2003) Interactions between growth factor receptors and adhesion molecules: Breaking the rules. Curr Opin Ceff Biol 15(5):565-571.
Pankov R, Yamada KM (2002) Fibronectin at a glance. J Ceff Sci 115(Pt20):3861-3863.
Kanchanawong P, Shtengel G, Pasapera AM, Ramko EB, Davidson MW, Hess HF, Waterman CM (201 0) Nanoscale architecture of integrin-based cell adhesions. Nature 468(7323):580-584.
Gugutkov D, Gonzalez-Garcia C, Hernandez JCR, Altankov G, Salmeron-Sanchez M (2009) Biological activity of the substrate-induced fibronectin network: insight into the third dimension through electrospun fibers. Langmuir 25 (18):10893-10900.
Llopis-Hernandez V, Rico P, Moratal D, Altankov G, Salmeron-Sanchez M (2013) Role of material-driven fibronectin fibrillogenesis in protein remodelling. BioRes Open Access 2(5):364-373.
Klotzsch E, Smith ML, Kubow KE, Muntwyler S, Little WC, Beyeler F, Gourdon D, Nelson BJ, Vogel V (2009) Fibronectin forms the most extensible biological fibers displaying switchable force-exposed cryptic binding sites. Proc Nat Acad Sci USA 106(43):18267-72.
Muller C, Stamov DR, Werner C, Pompe T (2012) Nanoscale characterization of cell receptors and binding sites on cell-derived extracellular matrices. Uftramicroscopy 118:44-52.
Hernandez JC, Salmeron-Sanchez M, Soria JM, Ribelles JLG, Pradas MM (2007) Substrate chemistry-dependent conformations of single laminin molecules on polymer surfaces are revealed by the phase signal of atomic force microscopy. Biophys J 93(1 ), 202-207.
Fu L, Tang T, Miao Y, Zhang S, Qu Z, Dai K (2008) Stimulation of osteogenic Substrate chemistry-dependent conformations of single laminin molecules on polymer surfaces are revealed by the phase signal of atomic force microscopy. Biophys J 93(1 ), 202-207.
Greenblatt MB, Shim JH, Zou W, Sitara D, Schweitzer M, Hu D, Lotinun S, Sano Y, Baron R, Park JM, Arthur S, Xie M, Schneider MD, Zhai B, Gygi S, Davis R, Glimcher LH (2010) The p38 MAPK pathway is essential for skeletogenesis and bone homeostasis in mice. J Clin Invest 120 (7):2457-2473.
Phimphilai M, Zhao Z, Soules H, Roca H, Franceschi RT (2006) BMP signaling is required for RUNX2-dependent induction of the osteoblast phenotype. J Bone Miner Res 21 (4):637-646.
Huebsch N, Arany PR, Mao AS, Shvartsman D, Ali OA, Bencherif SA, Rivera-Feliciano J, Mooney DJ (2010) Harnessing traction-mediated manipulation of the cell/matrix interface to control stem-cell fate. Nat Mater 9(6):518-526.
Trappmann B, Gautrot JE, Connelly JT, Strange DG, Li Y, Oyen ML, Cohen Stuart MA, Boehm H, Li B, Vogel V, Spatz JP, Watt FM, Huck WT (2012) Extracellular-matrix tethering regulates stem-cell fate. Nat Mater 11, 642-649.

Wen JH, Vincent LG, Fuhrmann A, Choi YS, Hribar KC, Taylor-Weiner H, Chen S, Engler AJ (2014) Interplay of matrix stiffness and protein tethering in stem cell differentiation. Nat Mater 13 (10):979-987.
Baneyx G, Baugh L, Vogel, V. Coexisting conformations of fibronectin in cell culture maged using fluorescence resonance energy transfer (2001) Proc Natl Acad Sci USA 98(25):14464-14468.
Watt FM, Hogan BL (2000) Out of Eden: stem cells and their niches. Science 287(5457):1427-1430.
Cantini, M, Rico P, Moratal D, Salmeron-Sanchez M (2012) Controlled wettability, same chemistry: biological activity of plasma-polymerized coatings. Soft Matter 8:5575-5584.
Ulmer J, Geiger B, Spatz J (2008) Force-induced fibronectin fibrillogenesis in vitro. Soft Matter 4, 1998-2007.
Pompe T, Renner L, Werner C (2005) Nanoscale features of fibronectin fibrillogenesis depend on protein-substrate interaction and cytoskeleton structure. Biophys J 88, 527-534.
Olsson AK, Dim berg A, Kreuger J, Claesson-Welsh L. VEGF receptor signalling—in control of vascular function. Nature Reviews Molecular Cell Biology. 2006;7:359-71.
Stratman AN, Davis MJ, Davis GE. VEGF and FGF prime vascular tube morphogenesis and sprouting directed by hematopoietic stem cell cytokines. Blood. 2011; 117:3709-19.
Hallmann R, Horn N, Selg M, Wendler 0, Pausch F, Sorokin LM. Expression and function of laminins in the embryonic and mature vasculature. Physiological Reviews. 2005;85:979-1000.
Moulton KS, Olsen BR, Sann S, Fukai N, Zurakowski D, Zeng XK. Loss of collagen XVIII enhances neovascularization and vascular permeability in atherosclerosis. Circulation. 2004; 110: 1330-6.
Rice JJ, Martino MM, De Laporte L, Tortelli F, Briquez PS, Hubbell JA. Engineering the Regenerative Microenvironment with Biomaterials. Advanced Healthcare Materials. 2013;2:57-71.
Sacchi V, Mittermayr R, Hartinger J, Martino MM, Lorentz KM, Wolbank S, et al. Long-lasting fibrin matrices ensure stable and functional angiogenesis by highly tunable, sustained delivery of recombinant VEGF164. Proceedings of the National Academy of Sciences. 2014;111 :6952-7.
Traub S, Morgner J, Martino MM, Hoening S, Swartz MA, Wickstroem SA, et al. The promotion of endothelial cell attachment and spreading using FNIII10 fused to VEGF-A(165). Biomaterials. 2013;34:5958-68.
Hanft JR, Pollak RA, Barbu I A, van Gils C, Kwon PS, Gray SM, et al. Phase I trial on the safety of topical rhVEGF on chronic neuropathic diabetic foot ulcers. Journal of wound care. 2008;17:30-2, 4-7.
Olea FD, Janavel GV, Cuniberti L, Yannarelli G, Meckert PC, Cors J, et al. Repeated, but not single, VEGF gene transfer affords protection against ischemic muscle lesions in rabbits with hindlimb ischemia. Gene Therapy. 2009;16:716-23.
Chen TT, Luque A, Lee S, Anderson SM, Segura T, Iruela-Arispe ML. Anchorage of VEGF to the extracellular matrix conveys differential signaling responses to endothelial cells. Journal of Cell Biology. 2010;188:595-609.
Hood JD, Frausto R, Kiosses WB, Schwartz MA, Cheresh DA. Differential alpha v integrin-mediated Ras-ERK signaling during two pathways of angiogenesis. Journal of Cell Biology. 2003;162:933-43.
Takahashi T, Yamaguchi S, Chida K, Shibuya M. A single autophosphorylation site on KDR/Flk-1 is essential for VEGF-A-dependent activation of PLC-gamma and DNA synthesis in vascular endothelial cells. EMBO Journal. 2001 ;20:2768-78.
Eming SA, Hubbell JA. Extracellular matrix in angiogenesis: dynamic structures with translational potential. Experimental Dermatology. 2011 ;20:605-13.
Fujio Y, Walsh K. Akt mediates cytoprotection of endothelial cells by vascular endothelial growth factor in an anchorage-dependent manner. Journal of Biological Chemistry. 1999;274:16349-54.
Friedlander M, Brooks PC, Shaffer RW, Kincaid CM, Varner JA, Cheresh DA. Definition of 2 Angiogenic Pathways by Distinct Alpha(V) Integrins. Science. 1995;270:1500-2.
Avraamides CJ, Garmy-Susini B, Varner JA. Integrins in angiogenesis and lymphangiogenesis. Nature Reviews Cancer. 2008; 8:604-17.

(56) References Cited

OTHER PUBLICATIONS

Saldi R, Mitola S, Strasly M, Defilippi P, Tarone G, Bussolino F. Role of alpha(v)beta(3) integrin in the activation of vascular endothelial growth factor receptor-2. EMBO Journal. 1999; 18:882-92.
Agarwal, et al. (2015) Biomaterial strategies for engineering implants for enhanced osseointegration and bone repair. Adv Drug Deliv Rev. 94: 53-62.
Nyberg, et al. Growth factor-eluting technologies for bone tissue engineering. Drug Deliv. and Transl. Res. (2016) 6:184-194.
Harada, et al. (2003) Control of osteoblast function and regulation of bone mass. Nature 423:349-355.
Gregory, et al. (2005) Adult Bone Marrow Stem/Progenitor Cells (MSCs) are Preconditioned by Microenvironmental Niche in Culture: A Two-Stage Hypothesis for Regulation of MSC Fate. Sci. STKE 2005, pe37.
Wagner, et al. (2008) Replicative Senescence of Mesenchymal Stem Cells: A Continuous and Organized Process. PLoS ONE 3(5): e2213.
Izadpanah, et al. (2008) Long-term In vitro Expansion Alters the Biology of Adult Mesenchymal Stem Cells. Cancer Res. 68(11): 4229-4238.
McBeath, et al. (2004) Cell Shape, Cytoskeletal Tension, and RhoA Regulate Stem Cell Lineage Commitment. Developmental Cell 6: 483-495.
Kilian, et al. (2010) Geometric cues for directing the differentiation of mesenchymal stem cells. PNAS 107(11): 4872-4877.
Yang, et al. (2014) Mechanical memory and dosing influence stem cell fate. Nature Materials 13(6): 645-652.
Curran, et al. (2006) The guidance of human mesenchymal stem cell differentiation in vitro by controlled modifications to the cell substrate. Biomaterials 27(27): 4783-4793.
Benoit, et al. (2008) Small functional groups for controlled differentiation of hydrogel-encapsulated human mesenchymal stem cells. Nat Mater. 7(10): 816-823.
Dalby, et al. (2007) Nanotopographical control of human osteoprogenitor differentiation. Curr. Stem Cell Res. Ther. 2, 129-38.
Oh, et al. (2009) Stem cell fate dictated solely by altered nanotube dimension. PNAS 106(7): 2130-2135.
McMurray, et al. (2011) Nanoscale surfaces for the long-term maintenance of mesenchymal stem cell phenotype and multipotency. Nat. Mater. 10: 637-644.
Engler, et al. (2006) Matrix elasticity directs stem cell lineage specification. Cell 126: 677-89.
Gilbert, et al. (2010) Substrate elasticity regulates skeletal muscle stem cell self-renewal in culture. Science 329: 1078-81.
Chaudhuri, 0. et al. (2016) Hydrogels with tunable stress relaxation regulate stem cell fate and activity. Nat Mater. 15(3): 326-334.
Salmerón-Sánchez, et al. (2011) Role of material-driven fibronectin fibrillogenesis in cell differentiation. Biomaterials 32: 2099-2105.
Ballester-Beltran, et al. (2012) Effect of topological cues on material-driven fibronectin fibrillogenesis and cell differentiation. J. Mater. Sci. Mater. Med. 23: 195-204.
Keselowsky, et al. (2004) Surface chemistry modulates focal adhesion composition and signaling through changes in Integrin binding. Biomaterials 25: 5947-5954.
Keselowsky, et al. (2005) Integrin binding specificity regulates biomaterial surface chemistry effects on cell differentiation. PNAS 102(17): 5953-5957.
Michael, et al. (2009) Focal adhesion kinase modulates cell adhesion strengthening via integrin activation. Mol. Biol. Cell 20: 2508-19.
Mei et al. (2010) Combinatorial development of biomaterials for clonal growth of human pluripotent stem cells. Nature Materials 9: 768-778.
Rico, et al. (2009) Substrate-induced assembly of fibronectin into networks: influence of surface chemistry and effect on osteoblast adhesion. Tissue Eng. Part A 15: 3271-3281.
Rico, et al. (2010) Molecular assembly and biological activity of a recombinant fragment of fibronectin (FNIII7-10) on poly(ethylacrylate). Colloids Surfaces B Biointerfaces 78: 310-316.
Guerra, et al. (2010) Subtle variations in polymer chemistry modulate substrate stiffness and fibronectin activity. Soft Matter 6: 4748-4755.
Reznikoff, et al. (1973) Establishment and Characterization of a Cloned Line of C3H Mouse Embryo Cells Sensitive to Postconfluence Inhibition of Division. Cancer Research 33: 3231-3238.
Penney, et al. (1989) 10T1/2 Cells: An In Vitro Model for Molecular Genetic Analysis of Mesodermal Determination and Differentiation. Environmental Health Perspectives 80: 221-227.
Gonzalez-Garcia, et al. (2012) Surface mobility regulates skeletal stem cell differentiation. Integr. Biol. (Camb). 4: 531-539.
Pittenger, et al. (1999) Multilineage Potential of Adult Human Mesenchymal Stem Cells. Science 284(5411): 143-147.
Dominici, et al. (2006) Position Paper: Minimal criteria for defining multipotent mesenchymal stromal cells. Cytotherapy 8(4): 315-317.
Chamberlain, et al. (2007) Concise review: mesenchymal stem cells: their phenotype, differentiation capacity, Immunological features, and potential for homing. Stem Cells 25: 2739-2749.
Kirkham et al. (2007) Genes and Proteins Involved in the Regulation of Osteogenesis. In Topics in Tissue Engineering, Eds. N Ashammakhi, R Reis & E Chiellini. vol. 3, Ch. 13.
Kim, et al. (2010) Ras activation contributes to the maintenance and expansion of Sca-1 pas cells in a mouse model of breast cancer. Cancer Lett. 287: 172-181.
Satelli, et al. (2011) Vimentin in cancer and its potential as a molecular target for cancer therapy. Cell. Mol. Life Sci. 68: 3033-3046.
Griffin, et al. (2004) Adhesion-contractile balance in myocytedifferentiation. J. Cell Sci. 117(24): 5855-5863.
Roca-Cusachs et al. (2012) Finding the weakest link—exploring integrin-mediated mechanical molecular pathways. Journal of Cell Science 125: 3025-3038.
Kaibuchi, et al. (1999) Regulation of the cytoskeleton and cell adhesion by the Rho family GTPases in mammalian cells. Annu. Rev. Biochem. 68: 459-486.
Narumiya, et al. (Elsevier, 2000) Regulators and Effectors of Small GTPases—Part D: Rho Family. Methods Enzymol. 325: 273-284.
Kovacs et al. (2004) Mechanism of Blebbistatin Inhibition of Myosin II. J. Bio. Chem. 279(34): 35557-35563.
Dalby, et al. (2007) The control of human mesenchymal cell differentiation using nanoscale symmetry and disorder. Nature Materials 6: 997-1003.
Phillips, et al. (2010) Human mesenchymal stem cell differentiation on self-assembled monolayers presenting different surface chemistries. Acta Biomater 6, 12-20.
Keselowsky, et al. (2003) Surface chemistry modulates fibronectin conformation and directs integrin binding and specificity to control cell adhesion. J. Biomed. Mater. Res. 66A: 247-259.
Chen, et al. (1997) Geometric Control of Cell Life and Death. Science 276(5317): 1425-1428.
Discher, et al. (2009) Growth factors, matrices, and forces combine and control stem cells. Science 324(5935): 1673-1677.
Geiger, et al. (2001) Transmembrane extracellular matrix- cytoskeleton crosstalk. Nat. Rev. Molecular Cell Biol. 2: 793-805.
Mitra, et al. (2005) Focal adhesion kinase: in command and control of cell motility. Nat. Rev. Mol. Cell Biol. 6: 56-68.
Schaller, et al. (1994) Autophosphorylation of the Focal Adhesion Kinase, pp125FAK Directs SH2-Dependent Binding of pp60src. Mol. Cell. Bio. 14(3): 1680-1688.
Lee, et al. (2009) Engineering integrin signaling for promoting embryonic stem cell self-renewal in a precisely defined niche. Biomaterials 31(6): 1219-1226.
Vanterpool et al., BioResearch Open Access (2014) 3(6): 286-296.
Dalby, et al. (2014) Harnessing nanotopography and integrin-matrix interactions to influence stem cell fate. Nature Materials (13): 558-569.
Bultmann, H., et al., "Fibronectin Fibrillogenesis Involves the Heparin II Binding Domain of Fibronectin." The Journal of Biological Chemistry, vol. 273, No. 5, Issue of Jan. 30, 1998, pp. 2601-2609.
Salmeron-Sanchez, M., et al., "Role of material-driven fibronectin fibrillogenesis in cell differentiation." Biomaterials 32 (2011) 2099-2105, www.elsevier.com/locate/biomaterials.

(56) References Cited

OTHER PUBLICATIONS

Wijelath, E., et al., "Heparin-II Domain of Fibronectin Is a Vascular Endothelial Growth Factor-Binding Domain—Enhancement of VEGF Biological Activity by a Singular Growth Factor/Matrix Protein Synergism." American Heart Association, Circulation Research, Oct. 13, 2006, pp. 853-860.
Hastings et al. (2015) Drug and cell delivery for cardiac regeneration. Advanced Drug Delivery Reviews 84: 85-106.
Shekaran, et al. (2014) Bone regeneration using an alpha 2 beta 1 integrin-specific hydrogel as a BMP-2 delivery vehicle. Biomateria/s 35, 5453-5461.
Search Report for GB1508931.1.
International Search Report for PCT/EP2016/061925.

\* cited by examiner a)

b)

SEQUENCE LISTING

<160> NUMBER OF SEQ ID NOS: 18

<210> SEQ ID NO 1
<211> LENGTH: 21
<212> TYPE: DNA
<213> ORGANISM: Artificial Sequence
<220> FEATURE:
<223> OTHER INFORMATION: Synthetic construct

<400> SEQUENCE: 1
cagcgaggta gtgaagagac c                                              21

<210> SEQ ID NO 2
<211> LENGTH: 22
<212> TYPE: DNA
<213> ORGANISM: Artificial Sequence
<220> FEATURE:
<223> OTHER INFORMATION: Synthetic construct

<400> SEQUENCE: 2
tctggagttt atttgggagc ag                                             22

<210> SEQ ID NO 3
<211> LENGTH: 20
<212> TYPE: DNA
<213> ORGANISM: Artificial Sequence
<220> FEATURE:
<223> OTHER INFORMATION: Synthetic construct

<400> SEQUENCE: 3
agaatgagaa gcgcctggag                                                20

<210> SEQ ID NO 4
<211> LENGTH: 20
<212> TYPE: DNA
<213> ORGANISM: Artificial Sequence
<220> FEATURE:
<223> OTHER INFORMATION: Synthetic construct

<400> SEQUENCE: 4
ctgccagtgt acagggaaga                                                20

<210> SEQ ID NO 5
<211> LENGTH: 20
<212> TYPE: DNA
<213> ORGANISM: Artificial sequence
<220> FEATURE:
<223> OTHER INFORMATION: Synthetic construct

<400> SEQUENCE: 5
gtcagtggtg gacctgacct                                                20

<210> SEQ ID NO 6
<211> LENGTH: 20
<212> TYPE: DNA
<213> ORGANISM: Artificial sequence
<220> FEATURE:
<223> OTHER INFORMATION: Synthetic construct

<400> SEQUENCE: 6
acctggtgct cagtgtagcc                                                20

<210> SEQ ID NO 7
<211> LENGTH: 20
<212> TYPE: DNA
<213> ORGANISM: Artificial sequence

```
<220> FEATURE:
<223> OTHER INFORMATION: Synthetic construct

<400> SEQUENCE: 7
tgagagtagg tgtcccgcct                                                    20

<210> SEQ ID NO 8
<211> LENGTH: 23
<212> TYPE: DNA
<213> ORGANISM: Artificial sequence
<220> FEATURE:
<223> OTHER INFORMATION: synthetic construct

<400> SEQUENCE: 8
tgtggattaa aaggacttgg tgc                                                23

<210> SEQ ID NO 9
<211> LENGTH: 19
<212> TYPE: DNA
<213> ORGANISM: Artificial sequence
<220> FEATURE:
<223> OTHER INFORMATION: Synthetic construct

<400> SEQUENCE: 9
tttgcctgtt tggcattgc                                                     19

<210> SEQ ID NO 10
<211> LENGTH: 20
<212> TYPE: DNA
<213> ORGANISM: Artificial sequence
<220> FEATURE:
<223> OTHER INFORMATION: Synthetic construct

<400> SEQUENCE: 10
tgggtgcagg ctgtaaagct                                                    20

<210> SEQ ID NO 11
<211> LENGTH: 19
<212> TYPE: DNA
<213> ORGANISM: Artificial sequence
<220> FEATURE:
<223> OTHER INFORMATION: Synthetic construct

<400> SEQUENCE: 11
agcaaagagg tggccatcc                                                     19

<210> SEQ ID NO 12
<211> LENGTH: 17
<212> TYPE: DNA
<213> ORGANISM: artificial construct
<220> FEATURE:
<223> OTHER INFORMATION: Synthetic construct

<400> SEQUENCE: 12
cttgcacggc ttctacg                                                       17

<210> SEQ ID NO 13
<211> LENGTH: 19
<212> TYPE: DNA
<213> ORGANISM: Artificial sequence
<220> FEATURE:
<223> OTHER INFORMATION: Synthetic construct

<400> SEQUENCE: 13
tgccctaagg acccctgaa                                                     19
```

```
<210> SEQ ID NO 14
<211> LENGTH: 20
<212> TYPE: DNA
<213> ORGANISM: Artificial sequence
<220> FEATURE:
<223> OTHER INFORMATION: Synthetic construct

<400> SEQUENCE: 14
cagttagaca cagagtctgc                                              20

<210> SEQ ID NO 15
<211> LENGTH: 20
<212> TYPE: DNA
<213> ORGANISM: Artificial sequence
<220> FEATURE:
<223> OTHER INFORMATION: Synthetic construct

<400> SEQUENCE: 15
gaccctggag gcacacagcc                                              20

<210> SEQ ID NO 16
<211> LENGTH: 24
<212> TYPE: DNA
<213> ORGANISM: Artificial sequence
<220> FEATURE:
<223> OTHER INFORMATION: Synthetic construct

<400> SEQUENCE: 16
catgtgggaa cattgcagga cccc                                         24

<210> SEQ ID NO 17
<211> LENGTH: 20
<212> TYPE: DNA
<213> ORGANISM: Artificial sequence
<220> FEATURE:
<223> OTHER INFORMATION: Synthetic construct

<400> SEQUENCE: 17
ggaggaatgt aacacgactg                                              20

<210> SEQ ID NO 18
<211> LENGTH: 23
<212> TYPE: DNA
<213> ORGANISM: Artificial sequence
<220> FEATURE:
<223> OTHER INFORMATION: Synthetic construct

<400> SEQUENCE: 18
tgcccactgc tgacttagga atc                                          23
```

MATERIALS AND METHODS FOR TISSUE REGENERATION

RELATED APPLICATIONS

This application is a National Stage filing and claims the benefit under 35 U.S.C. § 120 to PCT Application PCT/EP2016/061925, filed May 26, 2016, which claims priority to United Kingdom Patent Application Serial No. 1508931.1, filed May 26, 2015. The disclosures of the foregoing applications are herein incorporated by reference in their entireties.

SEQUENCE LISTING

The instant application contains a Sequence Listing which has been submitted in ASCII format via EFS-Web and is hereby incorporated by reference in its entirety. Said ASCII copy, created on Dec. 1, 2023, is named 4553.008US1 seq list 2 ST25.txt and is 3,913 bytes in size.

FIELD OF THE INVENTION

The invention relates to materials presenting a biologically active matrix comprising a physiological fibrillar fibronectin network, and in particular to their use for modulating cell behaviour and fate, including cell growth, proliferation and/or differentiation, such as for promoting tissue regeneration, for example, bone regeneration or vascularization.

BACKGROUND OF THE INVENTION

Following injury or disease, an organism undergoes a variety of (natural or induced) processes to direct cells, tissues and cellular processes towards healing and eventually regeneration. These processes generally involve growth factors (GFs), substances that control cell function through the activation of specific signalling pathways and that are capable of stimulating cellular growth, proliferation, and cellular differentiation. For example, current treatments in surgical orthopaedics and traumatology include bone autografts, bone substitutes and the use of GFs, especially bone morphogenetic proteins (BMP), despite limited success and significant drawbacks. The role of GFs in tissue regeneration is broadly recognised but the delivery of these GFs to enhance tissue healing has been only partially successful. One of the reasons for this poor clinical translation might lie in the rapid breakdown and clearance of GFs from tissue sites in vivo. To improve GF retention within the healing site, soluble administration and matrix delivery (e.g., collagen sponges) have relied on increasing the concentration of the GF used (6, 7). For example, current clinical delivery of BMP-2 involves the incorporation of the GF in a collagen sponge carrier at a concentration of 1.5 mg/ml to promote robust bone repair (8). However, it is important to note that catastrophic collateral risks have been described due to the high dosage. Reported serious respiratory, neurological, and inflammatory adverse effects eventually led the FDA in the USA to issue a Public Health Notification of life threatening complications associated with this therapeutic gold standard for bone repair. As another example, research aimed towards in vivo vascularization in pathological conditions is focused on endothelial cell growth in different 3D environments (hydrogels, synthetic polymer matrices) containing a combination of important GFs such as vascular endothelial growth factor (VEGF), fibroblast growth factor (FGF), platelet-derived growth factor (PDGF) or insulin-like growth factor (IGF) (44). However, similar significant drawbacks are encountered since this approach is very demanding on GF supply and faces issues like low GF stability and accessibility. Techniques incorporating molecules able to sequester these proteins seem to be one of the ways forward as it can considerably reduce GF concentration needed for biological response as well as present them in more efficient form (40). ECM proteins like fibrinogen or fibronectin or their engineered fragments have been utilized to bind GF such as BMP-2, PDGF, or VEGF, and were proven in in vivo wound healing assays (45, 46, 4). Concerns have also been raised about the progression of metastatic tumour lesions as side effects of the prolonged administration of angiogenic growth factors (61), such as the VEGF extensively used in preclinical models.

More generally, tissue environments control cell differentiation in response to regenerative demands using extracellular matrix (ECM) protein and growth factor (GF) cues. In tissues, the activity of GFs are regulated by their binding to ECM proteins (1). In vitro, highly engineered environments have been fabricated that demonstrate that cell signalling can be synergistically enhanced by the nanoscale co-localisation of integrins and GF receptors (2, 3). A major hurdle to translation of these seminal in vitro observations to medical devices is that while in vivo tissues have evolved to present complex cues in concert, man-made materials rely on complex engineering strategies to maximise GF activity (4, 5). The controlled delivery (localising and limiting release) of growth factors, including BMP-2, has been used in combination with biomaterial carriers with some successes in restoring tissue function and controlling stem cell differentiation (9-11). Elegant work has shown that cell signalling can be synergistically enhanced by the formation of clusters between integrins and GF receptors when the integrin binding ($FNIII_{9-10}$) and GF binding ($FNIII_{12-14}$) sites of fibronectin (FN) are presented together within the same engineered molecule (13). The approach promoted significant bone repair and wound healing via the incorporation of recombinant FN fragments within a fibrin matrix (3). The adequate presentation of GFs bound to the ECM is so crucial that a new generation of GFs has been engineered with super-binding affinity for a variety of ECM proteins (5).

Fibronectin (FN) is a ubiquitous extracellular matrix protein (ECM) protein that is organized into fibrillar networks by cells through an integrin-mediated process that involves contractile forces. FN is a glycoprotein which forms dimers consisting of two subunits (~220 kDa) linked by a single disulfide bond near the carboxyl termini. Each subunit contains three types of repeating modules (types I, II and III), which mediate interactions with other FN molecules, other ECM components, and cell surface receptors (FIG. 1a) (14). Most cells assemble rich matrices via an integrin-dependent contractile process that incorporates FN molecules, either synthesized by cells or reorganized from their surroundings, into matrix fibrils. FN fibril assembly involves the 70 kDa amino-terminal domain of FN, through binding of $I_{1-5}$ either to $III_{1-2}$ or $III_{12-14}$ domains (37). Attempts at inducing FN fibrillogenesis in vitro have yielded various results. Different ways of inducing FN fibrillogenesis in vitro produce different conformations of FN with different domains exposed depending on the surface properties and microenvironments produced by the substrate material and methods used (38, 39). It has been shown that certain materials can drive the self-organization of FN into (nano)networks capable of presenting integrins upon simple adsorption from a solution (12, 17).

The effective clinical translation of GFs into regenerative medicine demands robust, safe and effective systems that control delivery. The lack of effective ways to deliver GFs has thus limited their large potential clinical impact. Thus, there is an unmet clinical need to develop new therapeutic approaches for tissue regeneration, such as bone regeneration and vascularization in non-union bone defects and vascularization in pathological conditions more generally.

SUMMARY OF THE INVENTION

In vivo, tissue environments control cell behaviour and fate, including cell growth, proliferation and/or differentiation, in response to regenerative demands using extracellular matrix (ECM) protein and growth factor (GF) cues. For example, stem cell niches and tissues present structural proteins with cell adhesive cues and growth factors to stem cells. The activities of GFs are regulated by their binding to ECM proteins. While microenvironments which synergistically enhance cell signalling have been engineered in vitro, a major hurdle is that these systems rely on very complex engineering to maximize GF activity.

The inventors' work has shown how a polymer surface is used to engineer biologically complex microenvironments that enhance cell growth, proliferation and/or differentiation, such as mesenchymal stem cell (MSC) differentiation and vasculogenesis. The inventors have provided, for the first time, a simple, robust and translational material-based approach, using an implantable construct comprising a polymer material surface to provide a physiological fibrillar FN network capable of presenting GFs, such as BMP-2 or VEGF, in combination with the integrin binding domain of FN for synergistically enhanced cell signalling to direct cell growth, proliferation and/or differentiation.

Such simple engineering to permit spontaneous formation of synergistic environments represents a significant advance in driving next-generation biomaterials development through amplification of differentiation cues presented to e.g. stem cells. Simple synthetic materials also offer major advantages in drug administration in terms of driving down cost and overcoming safety issues due to the current clinical use of therapeutic GFs at supraphysiological levels. More particularly, such materials provide significant advantages over controlled-release and protein-engineering strategies to provide retention, delivery and presentation of GFs within artificial matrices. Using material supports to tune simultaneous and co-localised integrin and GF receptor signalling allows much lower GF doses to be used (<0.1 mg/cm$^2$), which makes the system robust in terms of safety and effectiveness and, simultaneously, economically more competitive than current commercially available products.

The implantable constructs of the invention are based on biocompatible substrates having a surface coating of a polymer from the alkyl acrylate family that drives FN fibrillogenesis. Poly(ethyl acrylate) (PEA) is a generally preferred component, while the phenomenon occurs also on polymers with increasing length of the side chain such as poly(butyl acrylate) (PBA), poly(heptyl acrylate) and poly (hexyl acrylate) (PHA), and also on copolymers of such polymers with other polymers that do not induce FN fibrillogenesis. The technology is applicable across many substrate materials (e.g. polymers, ceramics, metals, injectable compositions) and substrate topologies (e.g. bulk nonporous materials, hydrogels, porous scaffolds, microparticles, fibers). The material surface comprising the polymer is deposited on the surface of the substrate and induces FN fibrillogenesis. This material-driven FN fibrillogenesis results in a FN (nano)network that is spontaneously assembled on the material surface. Integrin-binding (FNIII$_{9-10}$) as well as growth factor-binding (FNIII$_{12-14}$) domains are displayed and colocalized. Without being bound by any particular theory, the system allows synergistic integrin-growth factor receptor signalling to enhance cell growth, proliferation and/or differentiation and tissue regeneration. Thus this material-based system allowing colocalization of integrins and GF receptors may be used to direct cell behaviour and fate, such as cell differentiation, more efficiently (e.g. with lower doses of GF) compared with the use of soluble GFs. The GF-binding domain of FN is able to sequester a large variety of GFs, including BMP, PDGF, FGF, transforming growth factor (TGF), VEGF, neurotrophic GFs and others (2), such that the constructs of the invention have potential utility in corresponding tissue regeneration scenarios. These constructs have the potential to serve not only as engineered delivery vehicles for GFs to allow synergistically enhanced cell signalling, but also simultaneously as temporary physical supports or scaffolds for regenerating tissue.

Thus, generally, the invention relates to an implantable construct which may be used in modulating cell behaviour and fate, including cell growth, proliferation and/or differentiation, such as for promoting tissue regeneration or growth, for example bone regeneration or vascularization. A construct of the invention is capable of presenting one or more growth factors and FN integrin-binding domain for growth factor receptor and integrin mediated cell signalling at a site at which modulation of cell growth, proliferation and/or differentiation is desired, such as for tissue regeneration or growth, e.g. a site of injury or disease. The construct may in addition serve as a physical support or scaffold for regenerating tissue.

In one aspect, the invention provides an implantable construct. The invention provides an implantable construct comprising:
  (a) a biocompatible substrate having a first surface;
  (b) a material surface comprising an alkyl acrylate polymer deposited on said first surface; and
  (c) a biologically active matrix assembled on said material surface, wherein said biologically active matrix comprises
    (i) fibronectin (FN); and
    (ii) a growth factor (GF).

The invention provides an implantable construct comprising:
  (a) a biocompatible substrate having a first surface;
  (b) a material surface comprising an alkyl acrylate polymer deposited on said first surface;
  (c) fibronectin (FN) adsorbed on said material surface; and
  (d) a growth factor (GF) adsorbed on said FN.

The alkyl acrylate polymer forming the material surface is capable of supporting the formation of a physiological fibrillar network of FN adsorbed on its surface. The FN and GF together provide a biologically active matrix assembled on the material surface.

The implantable construct itself (and components thereof) is cell-free, while the construct is cell-compatible for implantation in vivo or for use in in vitro cell culture.

The biocompatible substrate may be any material suitable for implantation for in vivo use or for use in in vitro cell culture, for example a polymer, a ceramic, a metal, or an alloy or composite thereof. In certain embodiments, the substrate is an implant. In certain embodiments, the substrate is a matrix or scaffold for supporting tissue regeneration or repair. In certain embodiments, the substrate is a matrix or scaffold for supporting in vitro cell culture.

The material surface may comprise, consist essentially of, or consist of an alkyl acrylate polymer.

The alkyl acrylate polymer forming the material surface is capable of supporting the formation of a physiological fibrillar network of FN adsorbed on its surface. Thus, FN has the conformation of a physiological fibrillar FN network upon adsorption on an alkyl acrylate polymer surface according to the invention.

The alkyl acrylate polymer may be a member of the group of polymers having the general formula —(C—C—COO$(CH_2)_xCH_3)_n$ where x=1 to 5. Preferably, the alkyl acrylate polymer is a member of the group of polymers having the formula —(C—C—COO$(CH_2)_xCH_3)_n$ where x=1, 3, or 5. The alkyl acrylate polymer preferably is poly(ethyl acrylate) (PEA) having the formula $CH_2CHCO_2CH_2CH_3$, i.e., where x=1 in the general formula. The alkyl acrylate polymer may be poly(butyl acrylate) (PBA) having the formula —$(CH_2CHCOO(CH_2)_3CH_3)_n$, i.e., where x=3 in the general formula. The alkyl acrylate polymer may be poly(hexyl acrylate) (PHA) having the formula —$(CH_2CHCOO(CH_2)_5CH_3)_n$, i.e., where x=5 in the general formula. The alkyl acrylate polymer may be a member of the group of polymers having the general formula —[$CH_2$—CH—COO—$(CH_2)_xCH_3]_n$— where x is an integer of 1 to 5. In the formula, n is an integer and designates the number of monomer units making up the polymer. Preferably, the alkyl acrylate polymer is a member of the group of polymers having the formula —[$CH_2$—CH—(COO—$(CH_2)_xCH_3]_n$— where x=1, 3, or 5 and n is as defined above. The alkyl acrylate polymer preferably is poly(ethyl acrylate) (PEA) having the formula [$CH_2CH(CO_2CH_2CH_3)]_n$, i.e., where x=1 in the general formula. The alkyl acrylate polymer may be poly(butyl acrylate) (PBA) having the formula [$CH_2CH(COO(CH_2)_3CH_3)]_n$, i.e., where x=3 in the general formula. The alkyl acrylate polymer may be formed using poly(hexyl acrylate) (PHA) monomer subunits having the formula [$CH_2CH(COO(CH_2)_5CH_3)]_n$, i.e., where x=5 in the general formula.

The alkyl acrylate polymer may be a copolymer or blend comprising (1) an alkyl acrylate polymer capable of supporting the formation of a physiological fibrillar network of FN upon adsorption on its surface and (2) an alkyl acrylate polymer which alone is not capable of supporting the formation of a physiological fibrillar network of FN adsorbed on its surface. PEA is a generally preferred first component of such a copolymer or blend, or alternatively PBA or PHA. PMA is a generally preferred second component of such a copolymer or blend. The alkyl acrylate polymer capable of inducing FN fibrillogenesis is present in the copolymer or blend in a sufficiently high amount to provide its function of supporting FN fibrillogenesis. Generally, the amount of alkyl acrylate polymer capable of inducing FN fibrillogenesis in the copolymer or blend is at least about 50%, is > about 50%, or is ≥ about 70%. The percentage may be by weight. For example, the copolymer may be PEA/PMA (70%/30%), PEA/PMA (60%/40%) or PEA/PMA (50%:50%).

The alkyl acrylate polymer is substantially free of low molecular mass substances. The alkyl acrylate polymer surface is deposited as a thin (sub micron) layer surface on the substrate. The alkyl acrylate polymer surface may be a spin-coated surface on the substrate.

The FN has the conformation of a physiological fibrillar FN network upon adsorption on the alkyl acrylate polymer surface, such as a PEA surface.

The FN may be isolated FN from plasma, for example FN isolated from human plasma. The FN may be isolated human FN from plasma. The FN may be produced using recombinant technology or by using chemical protein synthesis. The FN presents the GF binding sites ($FNIII_{12-14}$) such that GFs can be bound thereto, thereby capable of enhancing tissue regeneration and growth as required. The physiological fibrillar FN network ensures that GF bound to the FN is colocalized with binding sites for one or more GF receptors and one or more integrin binding sites favouring cell signalling by GF receptors and integrins. The FN on said material surface may be associated with a further ECM component, for example, vitronectin (VN), collagen IV and laminin, or a mixture thereof. For example up to 20 wt % (by reference to the FN) of such ECM components may be present. The FN and a further ECM component form a biologically active matrix on said material surface.

A growth factor of the construct is capable of binding a growth factor-binding domain of FN. A growth factor is capable of binding at least one of $FNIII_{12-14}$. A growth factor is capable of binding $FNIII_{12-14}$. In certain embodiments, the growth factor is BMP-2 or VEGF.

Thus the invention provides an implantable construct comprising:
  (a) a biocompatible substrate having a first surface;
  (b) a material surface comprising an alkyl acrylate polymer, such as poly(ethylacrylate) (PEA), deposited on said first surface; and
  (c) a biologically active matrix assembled on said material surface, wherein said biologically active matrix comprises
    (i) fibronectin (FN); and
    (ii) BMP-2 or VEGF.

The invention provides an implantable construct comprising:
  (a) a biocompatible substrate having a first surface;
  (b) a material surface comprising an alkyl acrylate polymer deposited on said first surface;
  (c) fibronectin (FN) adsorbed on said material surface; and
  (d) BMP-2 or VEGF adsorbed on said FN.

The alkyl acrylate polymer forming the material surface is capable of supporting the formation of a physiological fibrillar network of FN adsorbed on its surface. The FN and BMP-2, or FN and VEGF, together provide a biologically active matrix assembled on the material surface.

A growth factor may be BMP (e.g. BMP-2, BMP-7), VEGF, PDGF (e.g. PDGF-BB), TGF (e.g. TGF-β), FGF (e.g. FGF2), IGF, HGF, BDNF or a neurotrophic GF. A GF may be a recombinant GF. A GF may be a recombinant human GF. A GF may be an autologous GF with respect to an intended recipient of the implantable construct.

The FN and growth factor are adsorbed on the substrate. The FN is adsorbed on the polymer surface. A GF is adsorbed on the FN network.

The biologically active matrix assembled on said material surface may further comprise a further ECM component capable of forming a biologically active matrix when applied to said material surface, for example, vitronectin (VN), collagen IV and laminin, or a mixture thereof. For example up to 20 wt % (by reference to the FN) of such ECM components may be present.

The construct presents one or more growth factors and an integrin binding site of FN in a conformation favouring simultaneous availability for binding by one or more growth factor receptors and one or more integrins, respectively. The construct presents one or more growth factors in combination with an integrin binding site of FN in a conformation favouring cell signalling by growth factor receptors and integrins to direct cell growth, proliferation and/or differentiation. The construct presents binding sites for one or more growth factor receptors in combination with binding sites for one or more integrins to favour cell signalling to direct cell growth, proliferation and/or differentiation. The construct presents colocalized binding sites for one or more GFs, one or more GFs and GF receptors and one or more integrin binding sites favouring cell signalling by GF receptors and integrins.

The biologically active matrix presents one or more growth factors and an integrin binding site of FN in a conformation favouring simultaneous availability for binding by one or more growth factor receptors and one or more integrins, respectively. The biologically active matrix presents one or more growth factors in combination with an integrin binding site of FN in a conformation favouring cell signalling by growth factor receptors and integrins to direct cell growth, proliferation and/or differentiation. The biologically active matrix presents binding sites for one or more growth factor receptors in combination with binding sites for one or more integrins to favour cell signalling to direct cell growth, proliferation and/or differentiation. The biologically active matrix presents colocalized binding sites for one or more GFs, one or more GFs and GF receptors and one or more integrin binding sites favouring cell signalling by GF receptors and integrins.

An integrin binding site may be within the FN integrin binding domain ($FNIII_{9-10}$). A GF binding site is within the FN GF binding domain ($FNIII_{12-14}$).

The construct favours coordinated cell signalling by one or more growth factor receptors and one or more integrins. The construct favours synergistic cell signalling by one or more growth factor receptors and one or more integrins. The biologically active matrix favours coordinated cell signalling by one or more growth factor receptors and one or more integrins. The biologically active matrix favours synergistic cell signalling by one or more growth factor receptors and one or more integrins. Coordinated or synergistic cell signalling serves to drive or enhance cell growth, proliferation and/or differentiation, tissue regeneration or growth, treatment of injury or disease.

The invention provides an implantable construct obtained or produced by, or obtainable or producible by, methods of preparing a construct as described herein.

In such constructs, the FN and one or more growth factors are presented as a biologically active matrix assembled on the material surface, and the construct is implantable in a subject. The subject may be in need of cell signalling favoured by the biologically active matrix, to direct cell differentiation or tissue regeneration for the treatment of injury or disease for example. The construct is for implanting at a target site such as a site of injury or disease. The particular nature of the cell signalling, cell differentiation, tissue regeneration, injury and disease depends on the nature of the one or more growth factors in the biologically active matrix. For example, a construct comprising the growth factor BMP-2 has utility to direct mesenchymal stem cell (MSC) differentiation and bone regeneration (i.e. osteogenesis) for treatment of bone fractures.

In another aspect, the invention also provides an implantable construct as described above and herein for use in a method of modulating cell behaviour and fate, including cell growth, expansion, proliferation, differentiation and dedifferentiation. Modulation of such cell behaviour may be in vivo, e.g. in a subject in need of such modulated cell behaviour. The method may comprise locating the construct at a site of injury or disease. Modulation of such cell behaviour may be in vitro, e.g. in a cell culture.

The invention also provides an implantable construct as described above and herein for use in a method of promoting tissue regeneration or tissue growth. Promotion of tissue regeneration or growth may be in vivo, e.g. in a subject in need of tissue regeneration or growth. The method may comprise locating the construct at a site of injury or disease. Promotion of tissue regeneration or growth may be in vitro, e.g. in a cell culture.

The invention also provides an implantable construct as described above and herein for use in a method of promoting bone regeneration, for example in treating critical size bone defects after trauma or cancer, or bone growth, for example for spinal fusion. Promotion of bone regeneration or growth may be in vivo, e.g. in a subject in need of bone regeneration or growth. The method may comprise locating the construct at a site of injury or disease. For example, the method may comprise locating the construct at a site of bone damage or in need of vertebral bone fusion. Promotion of bone regeneration or growth may be in vitro, e.g. in a cell culture.

The invention also provides an implantable construct as described above and herein for use in a method of treating bone damage, e.g. bone fracture or a critical size bone defect. The in vivo treatment may be in a subject having bone injury or disease. The method may comprise locating the construct at a site of bone damage, e.g. from injury or disease. For example, the method may comprise locating the construct at a site of bone fracture or a critical size bone defect.

The invention also provides an implantable construct as described above and herein for use in a method of promoting vascularization. Promotion of vascularization may be in vivo, e.g. in a subject in need of vascularization, e.g. as a result of injury or disease. The method may comprise locating the construct at a site of injury or disease. For example, the method may comprise locating the construct at a site of tissue damage. Promotion of vascularization may be in vitro, e.g. in a cell culture.

The invention also provides an implantable construct as described above and herein for use in a method of wound healing or treating a wound. The in vivo treatment may be in a subject having tissue injury or disease. The method may comprise locating the construct at a site of tissue damage, e.g. from injury or disease. For example, the method may comprise locating the construct at a wound site.

In one aspect, the invention also provides a method of modulating cell behaviour and fate comprising locating an implantable construct at a site of injury or disease, wherein the construct is as described above and herein.

The invention also provides a method of promoting tissue regeneration or growth comprising locating an implantable construct at a site of injury or disease, wherein the construct is as described above and herein.

The invention also provides a method of promoting bone regeneration, for example in treating critical size bone defects after trauma or cancer, or bone growth, for example for spinal fusion, comprising locating an implantable construct at a site of injury or disease, wherein the construct is as described above and herein.

The invention also provides a method of treating bone damage, e.g. bone fracture or a critical size bone defect, comprising locating an implantable construct at a site of bone damage, e.g. from injury or disease, wherein the construct is as described above and herein. For example, the method may comprise locating the construct at a site of bone fracture or a critical size bone defect.

The invention also provides a method of promoting vascularization, for example in a subject in need of vascularization, e.g. as a result of injury or disease, comprising locating an implantable construct at a site of tissue damage e.g. from injury or disease, wherein the construct is as described above and herein.

The invention also provides a method of wound healing or treating a wound, for example in a subject having tissue injury or disease, comprising locating an implantable construct at a site of tissue damage, e.g. from injury or disease, wherein the construct is as described above and herein. For example, the method may comprise locating the construct at a wound site.

In one aspect, the invention also provides the use of:
(a) a biocompatible substrate having a first surface;
(b) a material surface comprising an alkyl acrylate polymerposited on said first surface; and
(c) a biologically active matrix assembled on said material surface, wherein said biologically active matrix comprises
  (i) fibronectin (FN); and
  (ii) a growth factor (GF), all as described herein,
in the preparation of an implantable construct for modulating cell behaviour and fate, including cell growth, expansion, proliferation, differentiation and dedifferentiation.

The invention also provides the use of:
(d) a biocompatible substrate having a first surface;
(e) a material surface comprising an alkyl acrylate polymer deposited on said first surface; and
(f) a biologically active matrix assembled on said material surface, wherein said biologically active matrix comprises
  (i) fibronectin (FN); and
  (ii) a growth factor (GF), all as described herein,
in the preparation of an implantable construct for promoting tissue regeneration or growth.

The invention also provides the use of:
(a) a biocompatible substrate having a first surface;
(b) a material surface comprising an alkyl acrylate polymer deposited on said first surface; and
(c) a biologically active matrix assembled on said material surface, wherein said biologically active matrix comprises
  (i) fibronectin (FN); and
  (ii) a growth factor (GF), all as described herein,
in the preparation of an implantable construct for promoting bone regeneration, for example in treating critical size bone defects after trauma or cancer, or bone growth, for example for spinal fusion.

The invention also provides the use of:
(a) a biocompatible substrate having a first surface;
(b) a material surface comprising an alkyl acrylate polymer deposited on said first surface; and
(c) a biologically active matrix assembled on said material surface, wherein said biologically active matrix comprises
  (i) fibronectin (FN); and
  (ii) a growth factor (GF), all as described herein,
in the preparation of an implantable construct for treating bone damage, e.g. from injury or disease, e.g. bone fracture or a critical size bone defect.

The invention also provides the use of:
(d) a biocompatible substrate having a first surface;
(e) a material surface comprising an alkyl acrylate polymer deposited on said first surface; and
(f) a biologically active matrix assembled on said material surface, wherein said biologically active matrix comprises
  (i) fibronectin (FN); and
  (ii) a growth factor (GF), all as described herein,
in the preparation of an implantable construct for promoting vascularization, for example in a subject in need of vascularization, e.g. as a result of injury or disease.

The invention also provides the use of:
(d) a biocompatible substrate having a first surface;
(e) a material surface comprising an alkyl acrylate polymer deposited on said first surface; and
(f) a biologically active matrix assembled on said material surface, wherein said biologically active matrix comprises
  (i) fibronectin (FN); and
  (ii) a growth factor (GF), all as described herein,
in the preparation of an implantable construct for wound healing or treating a wound, e.g. from tissue injury or disease.

Where the construct is used in the context of promoting bone regeneration or growth, or treating bone damage, the growth factor may be BMP-2.

Thus, the invention also provides an implantable construct comprising:
(a) a biocompatible substrate having a first surface;
(b) a material surface comprising an alkyl acrylate polymer, such as poly(ethylacrylate) (PEA), deposited on said first surface; and
(c) a biologically active matrix assembled on said material surface, wherein said biologically active matrix comprises
  (i) fibronectin (FN); and
  (ii) a growth factor (GF), wherein the growth factor is BMP-2.
for use in a method of promoting bone regeneration, e.g. for treating critical size bone defects after trauma or cancer, or promoting bone growth, e.g. for spinal fusion, or treating bone damage, e.g. bone fracture or a critical size bone defect.

The invention also provides a method of promoting bone regeneration, e.g. for treating critical size bone defects after trauma or cancer, or promoting bone growth, e.g. for spinal fusion, or a method of treating bone damage, e.g. bone fracture or a critical size bone defect, comprising locating an implantable construct at a site of injury or disease, or at a site of bone damage, e.g. from injury or disease, wherein the construct comprises:
(a) a biocompatible substrate having a first surface;
(b) a material surface comprising an alkyl acrylate polymer, such as poly(ethylacrylate) (PEA), deposited on said first surface; and
(c) a biologically active matrix assembled on said material surface, wherein said biologically active matrix comprises
  (i) fibronectin (FN); and
  (ii) a growth factor (GF), wherein the growth factor is BMP-2.

Where the construct is used in the context of promoting vascularization, or wound healing, the growth factor may be VEGF.

Thus, the invention also provides an implantable construct comprising:
(d) a biocompatible substrate having a first surface;
(e) a material surface comprising an alkyl acrylate polymer, such as poly(ethylacrylate) (PEA), deposited on said first surface; and (f) a biologically active matrix assembled on said material surface, wherein said biologically active matrix comprises
   (i) fibronectin (FN); and
   (ii) a growth factor (GF), wherein the growth factor is VEGF.
for use in a method of promoting vascularization, e.g. in a subject in need of vascularization as a result of injury or disease, or treating a wound.

The invention also provides a method of promoting vascularization, or a method of treating a wound, comprising locating an implantable construct at a site of tissue damage, e.g. from injury or disease, or at a wound site, wherein the construct comprises:
   (d) a biocompatible substrate having a first surface;
   (e) a material surface comprising an alkyl acrylate polymer, such as poly(ethylacrylate) (PEA), deposited on said first surface; and
   (f) a biologically active matrix assembled on said material surface, wherein said biologically active matrix comprises
      (i) fibronectin (FN); and
      (ii) a growth factor (GF), wherein the growth factor is VEGF.

For these therapeutic uses and methods, the construct presents one or more growth factors and an integrin binding site of FN in a conformation favouring simultaneous availability for binding by one or more growth factor receptors and one or more integrins, respectively. The construct presents one or more growth factors in combination with an integrin binding site of FN in a conformation favouring cell signalling by growth factor receptors and integrins to direct cell growth, proliferation and/or differentiation. The construct presents binding sites for one or more growth factor receptors in combination with binding sites for one or more integrins to favour cell signalling to direct cell growth, proliferation and/or differentiation. The construct presents colocalized binding sites for one or more GFs, one or more GFs and GF receptors and one or more integrin binding sites favouring cell signalling by GF receptors and integrins.

For these therapeutic uses and methods, the biologically active matrix presents one or more growth factors and an integrin binding site of FN in a conformation favouring simultaneous availability for binding by one or more growth factor receptors and one or more integrins, respectively. The biologically active matrix presents one or more growth factors in combination with an integrin binding site of FN in a conformation favouring cell signalling by growth factor receptors and integrins to direct cell growth, proliferation and/or differentiation. The biologically active matrix presents binding sites for one or more growth factor receptors in combination with binding sites for one or more integrins to favour cell signalling to direct cell growth, proliferation and/or differentiation. The biologically active matrix presents colocalized binding sites for one or more GFs, one or more GFs and GF receptors and one or more integrin binding sites favouring cell signalling by GF receptors and integrins.

An integrin binding site may be within the FN integrin binding domain ($FNIII_{9-10}$). A GF binding site is within the FN GF binding domain ($FNIII_{12-14}$).

For these therapeutic uses and methods, the construct favours coordinated cell signalling by one or more growth factor receptors and one or more integrins. The construct favours synergistic cell signalling by one or more growth factor receptors and one or more integrins. The biologically active matrix favours coordinated cell signalling by one or more growth factor receptors and one or more integrins. The biologically active matrix favours synergistic cell signalling by one or more growth factor receptors and one or more integrins. Coordinated or synergistic cell signalling serves to drive or enhance cell growth, proliferation and/or differentiation, tissue regeneration or growth, treatment of injury or disease.

In another aspect, the invention also provides a method of preparing an implantable construct as described above and herein, comprising the steps of:
   (a) depositing an alkyl acrylate polymer on a first surface of a biocompatible substrate to form a material surface;
   (b) applying fibronectin and a growth factor to said material surface to form a biologically active matrix.

The invention also provides a method of preparing an implantable construct as described above, comprising the steps of:
   (a) providing a biocompatible substrate having a first surface;
   (b) depositing an alkyl acrylate polymer on said first surface to form a material surface;
   (c) applying fibronectin and a growth factor to said material surface to form a biologically active matrix.

The method of preparing the construct is cell-free.

The alkyl acrylate polymer surface is deposited as a thin (sub micron) layer surface on the substrate. The alkyl acrylate polymer may be spin coated onto the substrate. The alkyl acrylate polymer may be plasma polymerized onto the substrate.

The FN and GF are adsorbed from solution onto the alkyl acrylate polymer surface. In certain embodiments, the FN and GF are applied sequentially, with the FN applied before the GF. In certain embodiments, the FN and GF are applied concomitantly.

The step of applying fibronectin and a growth factor to said material surface to form a biologically active matrix may further comprise applying to said material surface a further ECM component capable of forming a biologically active matrix when applied to said material surface, e.g. vitronectin (VN), collagen IV, laminin. The further ECM component is adsorbed from solution onto the alkyl acrylate polymer surface. The further ECM component may be applied sequentially or concomitantly with respect to the FN and/or GF.

In another aspect, the invention also provides a kit comprising an implantable construct of the invention as described above and herein and instructions for using the kit. The instructions may indicate use of the kit in a method of tissue regeneration or growth, such as bone regeneration or vascularization. The instructions may indicate use of the kit for the treatment of bone damage, e.g. from injury or disease, e.g. a bone fracture or a critical size bone defect, or for vertebral bone fusion, or for the treatment of a wound, as described in detail herein. Where the kit is indicated for use in the context of promoting bone regeneration or growth or treating bone damage, the growth factor may be BMP-2. Where the kit is indicated for use in me context of promoting vascularization or wound healing, the growth factor may be VEGF.

The invention also provides a kit for an implantable construct comprising:
   (a) a biocompatible substrate having a first surface and a material surface comprising an alkyl acrylate polymer deposited on said first surface; and
   (b) fibronectin (FN) and a growth factor (GF) capable of forming a biologically active matrix when applied to said material surface; and (c) instructions for adsorbing the fibronectin (FN) and a growth factor (GF) onto the material surface to form a biologically active matrix, thus forming an implantable construct.

The construct and components of the construct of the kit are cell-free.

The construct and components of the construct of the kit are as described herein in the context of constructs and uses of constructs, including in respect of their compositions and properties, i.e. their structural and functional features.

The kit may further comprise a further ECM component, for example, vitronectin (VN), collagen IV, laminin, capable of forming a biologically active matrix when applied to said polymer surface and further instructions for adsorbing said further ECM component onto the material surface to form a biologically active matrix.

Instructions for using the kit may indicate use of the kit in a method of tissue regeneration or growth, such as bone regeneration or vascularization. The instructions may indicate use of the kit for the treatment of bone damage, e.g. from injury or disease, e.g. a bone fracture or a critical size bone defect, or for vertebral bone fusion, or for the treatment of a wound, as described in detail herein. Where the kit is indicated for use in the context of promoting bone regeneration or growth or treating bone damage, the growth factor may be BMP-2. Where the kit is indicated for use in the context of promoting vascularization or wound healing, the growth factor may be VEGF.

In one aspect, the invention concerns an implantable construct essentially as described herein wherein a growth factor (GF) is an endogenous GF in a subject in which the construct is implanted. An endogenous GF is capable of binding a growth factor-binding domain of fibronectin (FN), in particular $FNIII_{12-14}$. The alkyl acrylate polymer forming the material surface is capable of supporting the formation of a physiological fibrillar network of FN adsorbed on its surface, which is capable of recruiting and binding endogenous GFs. The FN and GF together provide a biologically active matrix assembled on the material surface. The physiological fibrillar network of FN may also bind an exogenous GF provided, such as a recombinant GF, preferably a recombinant human GF, or an autologous GF with respect to the subject in which the construct is implanted. Thus the biologically active matrix assembled on the material surface may comprise both an endogenous GF and an exogenous GF.

Thus, in one aspect, the invention provides such an implantable construct for use in a method of modulating cell behaviour and fate, including cell growth, expansion, proliferation, differentiation and dedifferentiation; promoting tissue regeneration or tissue growth; promoting bone regeneration, for example in treating critical size bone defects after trauma or cancer, or bone growth, for example for spinal fusion; treating bone damage, e.g. bone fracture or a critical size bone defect; promoting vascularization; or wound healing or treating a wound.

Such modulating, promoting or treating may be in vivo, e.g. in a subject in need of such modulation, promotion or treatment. The method may comprise locating the construct at a site of injury or disease.

For example, promotion of bone regeneration or growth may be in vivo, e.g. in a subject in need of bone regeneration or growth. The method may comprise locating the construct at a site of injury or disease. For example, the method may comprise locating the construct at a site of bone damage or in need of vertebral bone fusion. For example, the in vivo treatment may be in a subject having bone injury or disease.

The method may comprise locating the construct at a site of bone damage, e.g. from injury or disease. For example, the method may comprise locating the construct at a site of bone fracture or a critical size bone defect.

The implantable construct for use may comprise:
a biocompatible substrate having a first surface;
a material surface comprising an alkyl acrylate polymer deposited on said first surface; and
a biologically active matrix assembled on said material surface, wherein said biologically active matrix comprises fibronectin (FN); and
optionally, a growth factor (GF).

The implantable construct for use may comprise:
a biocompatible substrate having a first surface;
a material surface comprising an alkyl acrylate polymer deposited on said first surface; fibronectin (FN) adsorbed on said material surface; and
optionally, a growth factor (GF) adsorbed on said FN.

The components of the implantable construct for use are as described herein. In particular, the implantable construct itself (and components thereof) is cell-free, while the construct is cell-compatible for implantation in vivo.

In one aspect, the invention also provides: a method of modulating cell behaviour and fate comprising locating such an implantable construct at a site of injury or disease; a method of promoting tissue regeneration or growth comprising locating such an implantable construct at a site of injury or disease; a method of promoting bone regeneration, for example in treating critical size bone defects after trauma or cancer, or bone growth, for example for spinal fusion, comprising locating such an implantable construct at a site of injury or disease; a method of treating bone damage, e.g. bone fracture or a critical size bone defect, comprising locating such an implantable construct at a site of bone damage, e.g. from injury or disease, for example locating the construct at a site of bone fracture or a critical size bone defect; a method of promoting vascularization, for example in a subject in need of vascularization, e.g. as a result of injury or disease, comprising locating an implantable construct at a site of tissue damage e.g. from injury or disease; or a method of wound healing or treating a wound, for example in a subject having tissue injury or disease, comprising locating an implantable construct at a site of tissue damage, e.g. from injury or disease, for example locating the construct at a wound site.

The implantable construct used in the method may comprise:
a biocompatible substrate having a first surface;
a material surface comprising an alkyl acrylate polymer deposited on said first surface; and
a biologically active matrix assembled on said material surface, wherein said biologically active matrix comprises fibronectin (FN); and
optionally, a growth factor (GF).

The implantable construct used in the method may comprise:
a biocompatible substrate having a first surface;
a material surface comprising an alkyl acrylate polymer deposited on said first surface; fibronectin (FN) adsorbed on said material surface; and
optionally, a growth factor (GF) adsorbed on said FN.

The components of the implantable construct are as described herein. In particular, the implantable construct itself (and components thereof) is cell-free, while the construct is cell-compatible for implantation in vivo.

In one aspect, the invention also provides the use of:
a biocompatible substrate having a first surface;
a material surface comprising an alkyl acrylate polymer-posited on said first surface; and
a biologically active matrix assembled on said material surface, wherein said biologically active matrix comprises
fibronectin (FN); and
optionally, a growth factor (GF), all as described herein, in the preparation of an implantable construct for: modulating cell behaviour and fate, including cell growth, expansion, proliferation, differentiation and dedifferentiation; promoting tissue regeneration or growth; promoting bone regeneration, for example in treating critical size bone defects after trauma or cancer, or bone growth, for example for spinal fusion; treating bone damage, e.g. from injury or disease, e.g. bone fracture or a critical size bone defect; promoting vascularization, for example in a subject in need of vascularization, e.g. as a result of injury or disease; or wound healing or treating a wound, e.g. from tissue injury or disease.

The components of the implantable construct are as described herein. In particular, the implantable construct itself (and components thereof) is cell-free, while the construct is cell-compatible for implantation in vivo.

In the aspects above in which the implantable construct optionally comprises a GF, said optional GF is an exogenous GF provided to the construct, such as a recombinant GF, preferably a recombinant human GF, or an autologous GF with respect to the subject in which the construct is for use or is used. The physiological fibrillar network of FN on the surface of the alkyl acrylate polymer forming the material surface of the implantable construct is capable of recruiting and binding an endogenous GF of a subject in which the construct is used, such that an endogenous GF binds a growth factor-binding domain of fibronectin (FN), in particular $FNIII_{12-14}$. Thus, in the implantable construct in use, the FN and GF (endogenous or both endogenous and exogenous) together provide a biologically active matrix assembled on the material surface. The FN presents the GF binding sites ($FNIII_{12-14}$) such that endogenous GFs can be recruited onto the matrix and bound thereto, thereby enhancing tissue regeneration and growth as required. The physiological fibrillar FN network ensures that GF recruited and bound to the FN is colocalized with binding sites for one or more GF receptors and one or more integrin binding sites favouring cell signalling by GF receptors and integrins.

For these therapeutic uses and methods, the construct in use presents one or more growth factors and an integrin binding site of FN in a conformation favouring simultaneous availability for binding by one or more growth factor receptors and one or more integrins, respectively. The construct in use presents one or more growth factors in combination with an integrin binding site of FN in a conformation favouring cell signalling by growth factor receptors and integrins to direct cell growth, proliferation and/or differentiation. The construct in use presents binding sites for one or more growth factor receptors in combination with binding sites for one or more integrins to favour cell signalling to direct cell growth, proliferation and/or differentiation. The construct in use presents colocalized binding sites for one or more GFs, one or more GFs and GF receptors and one or more integrin binding sites favouring cell signalling by GF receptors and integrins.

For these therapeutic uses and methods, the biologically active matrix in use presents one or more growth factors and an integrin binding site of FN in a conformation favouring simultaneous availability for binding by one or more growth factor receptors and one or more integrins, respectively. The biologically active matrix in use presents one or more growth factors in combination with an integrin binding site of FN in a conformation favouring cell signalling by growth factor receptors and integrins to direct cell growth, proliferation and/or differentiation. The biologically active matrix in use presents binding sites for one or more growth factor receptors in combination with binding sites for one or more integrins to favour cell signalling to direct cell growth, proliferation and/or differentiation. The biologically active matrix in use presents colocalized binding sites for one or more GFs, one or more GFs and GF receptors and one or more integrin binding sites favouring cell signalling by GF receptors and integrins.

An integrin binding site may be within the FN integrin binding domain ($FNIII_{9-10}$). A GF binding site is within the FN GF binding domain ($FNIII_{12-14}$).

For these therapeutic uses and methods, the construct in use favours coordinated cell signalling by one or more growth factor receptors and one or more integrins. The construct in use favours synergistic cell signalling by one or more growth factor receptors and one or more integrins. The biologically active matrix in use favours coordinated cell signalling by one or more growth factor receptors and one or more integrins. The biologically active matrix in use favours synergistic cell signalling by one or more growth factor receptors and one or more integrins. Coordinated or synergistic cell signalling serves to drive or enhance cell growth, proliferation and/or differentiation, tissue regeneration or growth, treatment of injury or disease.

In another aspect, the invention concerns a construct having features essentially as described herein for sustaining growth of stem cells or maintaining stem cells (maintaining stemness).

Thus, in one aspect, the invention provides such a construct for use in a method of sustaining growth of stem cells or maintaining stem cells (maintaining stemness).

The construct for use may comprise:
a biocompatible substrate having a first surface;
a material surface comprising an alkyl acrylate polymer deposited on said first surface; and
a biologically active matrix assembled on said material surface, wherein said biologically active matrix comprises fibronectin (FN).

The construct for use may comprise:
a biocompatible substrate having a first surface;
a material surface comprising an alkyl acrylate polymer deposited on said first surface; and fibronectin (FN) adsorbed on said material surface.

The components of the construct for use are as described herein for implantable constructs of the invention. In particular, the construct itself (and components thereof) is cell-free, while the construct is cell-compatible for culture with cells in vitro.

In one aspect, the invention also provides a method of sustaining growth of stem cells or maintaining stem cells (maintaining stemness).

The construct used in the method may comprise:
a biocompatible substrate having a first surface;
a material surface comprising an alkyl acrylate polymer deposited on said first surface; and
a biologically active matrix assembled on said material surface, wherein said biologically active matrix comprises fibronectin (FN).

The construct used in the method may comprise:
a biocompatible substrate having a first surface;
a material surface comprising an alkyl acrylate polymer deposited on said first surface; and
fibronectin (FN) adsorbed on said material surface.

The components of the construct are as described herein for implantable constructs of the invention. In particular, the construct itself (and components thereof) is cell-free, while the construct is cell-compatible for culture with cells in vitro.

In one aspect, the invention also provides use of a construct for sustaining growth of stem cells or maintaining stem cells (maintaining stemness). The invention provides use of a construct for the preparation of a stem cell culture. The culture is capable of sustaining growth of stem cells or maintaining stem cells (maintaining stemness).

Such sustaining growth of stem cells or maintaining stem cells (maintaining stemness) in any of these aspects may be in vitro, e.g. in in vitro culture with stem cells.

The stem cells may be mesenchymal stem cells (MSCs). The stem cells may be murine stem cells, for example murine MSCs. The stem cells may be human stem cells. The stem cells may not be human embryonic cells unless they are obtained without the use, involving the destruction, of a human embryo.

The stem cells may be obtained from a subject in need of: modulated cell behaviour and fate, including cell growth, expansion, proliferation, differentiation and dedifferentiation; tissue regeneration or tissue growth; bone regeneration, for example in treatment of critical size bone defects after trauma or cancer, or bone growth, for example for spinal fusion; treatment of bone damage, e.g. bone fracture or a critical size bone defect; vascularization; or wound healing or treating a wound.

The method or use may comprise contacting the construct with a stem cell, for example a mesenchymal stem cell (MSC), under conditions capable of supporting stem cell viability or growth, for example in basal media, which lack soluble factors such as growth factors. For example, murine MSCs may be cultured in Dulbecco's modified Eagle's growth medium (DMEM) with 10% fetal bovine serum, for example as described in the experimental examples herein. Examples of suitable media such as basal media for supporting stem cell viability or growth are also well known in the art.

Sustained growth of stem cells or maintained stem cells (maintained stemness) may be determined by analysing the morphology of cells and/or the expression of suitable specific stem cell markers, e.g. Sca1, for example using immunohistochemistry assays or PCR, for example as described in the experimental examples herein. Examples of suitable immunohistochemistry assays and PCR and specific stem cell markers are also known in the art.

In one aspect, the invention provides a composition comprising a construct, said construct comprising a biocompatible substrate having a first surface, a material surface comprising an alkyl acrylate polymer deposited on said first surface and fibronectin (FN) adsorbed on said material surface, and a murine MSC. The composition may comprise Dulbecco's modified Eagle's growth medium (DMEM) with 10% fetal bovine serum. The components of the construct are as described herein for implantable constructs of the invention. In particular, the construct itself (and components thereof) is cell-free.

In one aspect, the invention provides a stem cell culture comprising a construct, said construct comprising a biocompatible substrate having a first surface, a material surface comprising an alkyl acrylate polymer deposited on said first surface and fibronectin (FN) adsorbed on said material surface, and a murine MSC. The cell culture may comprise Dulbecco's modified Eagle's growth medium (DMEM) with 10% fetal bovine serum. The components of the construct are as described herein for implantable constructs of the invention. In particular, the construct itself (and components thereof) is cell-free.

The above aspects, features and embodiments of the invention are described further below.

Constructs, Methods of Preparing Constructs and Uses of Constructs

The construct typically provides a conducive environment for cell signalling of one or more growth factor receptors (GF receptors) and one or more integrins in a subject in which the construct is implanted, or in vitro, e.g. in a cell culture in which the construct is present, and thus to direct cell growth, proliferation and/or differentiation or tissue regeneration or growth, for the treatment of injury or disease or use therein, for example.

The construct presents one or more growth factors and an integrin binding site of FN in a conformation favouring simultaneous availability for binding by one or more growth factor receptors and one or more integrins, respectively. The construct presents one or more growth factors in combination with an integrin binding site of FN in a conformation favouring cell signalling by growth factor receptors and integrins to direct cell growth, proliferation and/or differentiation. The construct presents binding sites for one or more growth factor receptors in combination with binding sites for one or more integrins to favour cell signalling to direct cell growth, proliferation and/or differentiation. The construct presents colocalized binding sites for one or more GFs, one or more GFs and one or more integrin binding sites favouring cell signalling by GF receptors and integrins.

An integrin binding site may be within the FN integrin binding domain ($FNIII_{9-10}$). FN also contains other integrin binding sites, extradomain A (EDA) and a variable domain (V) (FIG. 5a). A GF binding site is within the FN GF binding domain ($FNIII_{12-14}$).

The construct favours coordinated cell signalling by one or more growth factor receptors and one or more integrins. The construct favours synergistic cell signalling by one or more growth factor receptors and one or more integrins. Coordinated or synergistic cell signalling serves to drive or enhance cell growth, proliferation and/or differentiation, tissue regeneration or growth, treatment of injury or disease.

Coordinated or synergistic cell signalling means cell signalling resulting from binding of one or more growth factor receptors and one or more integrins to simultaneously available one or more growth factors and one or more integrin binding sites of FN, respectively. Binding of one or more growth factor receptors and one or more integrins may be simultaneous or substantially simultaneous, e.g., temporally overlapping binding. Such binding results from colocalization or clustering of binding sites for one or more growth factors, one or more growth factors and one or more integrin binding sites of FN.

The colocalization of GF binding sites, GFs and integrin binding sites and the coordinated or synergistic cell signalling by GF receptors and integrins allows the construct to enhance cell growth, proliferation and/or differentiation and its downstream effects compared with use of soluble GFs (i.e. without colocalization).

The construct itself is cell-free. The construct is cell-compatible for implantation in vivo or for use in vitro, e.g. in cell culture.

The substrate of the construct is composed of a biocompatible material. In certain embodiments, the substrate is bioresorbable such that the material can be broken down within the body, to reduce or eliminate the need for further intervention to remove the construct after use.

The biocompatible substrate may be any material suitable for implantation in vivo or for in vitro cell culture use, as are known in the art and understood by those skilled in the art. The substrate is cell-free. The substrate is cell-compatible for implantation in vivo or for use in vitro in cell culture.

Suitable materials include synthetic and natural materials such as polymers, ceramics and metals, including alloys and composites of such materials.

For example, biocompatible synthetic and natural polymers include polyvinyl alcohol (PVA), oligo[poly[ethylene glycol) fumarate] (OPF), and polymers and copolymers of monomers such as glycolic acid and lactic acid, such as poly(glycolic acid) (PGA), poly(lactic acid) (PLA) and poly(lactic-co-glycolic acid) (PLGA), polyether ether ketone (PEEK), polycaprolactone (PCL), chitosan and glycosaminoglycans (GAGs). Biocompatible polymers may be in the form of gels, including hydrogels, or structural scaffolds or matrices.

For example, biocompatible ceramics include hydroxyl carbonate apatite (HCA), calcium phosphate, hydroxyapatite (HA), tricalcium phosphate, bioactive glasses, alumina, zirconia, graphite and graphene. Biocompatible ceramics may be in the form of structural scaffolds or matrices.

For example, biocompatible metals include stainless steel, cobalt-chromium, titanium and titanium alloys. Biocompatible metals may be in the form of structural scaffolds or matrices.

The biocompatible substrate may be a metal coated ceramic particle, such as a metal coated hydroxyapatite particle such as described in WO 2010/136777. The metal coating can optionally be titanium or a titanium alloy.

Biocompatible substrates may be particulate. The construct may thus be in the form of a composition for example, which is implantable at a target site by injection or infusion. For example, the construct may be introduced to the site of disease or injury by injection of a pharmaceutically acceptable composition comprising the construct. For example, biocompatible polymer particles (e.g. polylactic acid, PLLA), having a size of about 100 μm for example, in a pharmaceutically acceptable carrier may be used.

Suitable biocompatible particles are known in the art, as are pharmaceutically acceptable carriers as is readily understood by those skilled in the art.

In a similar manner as described herein for the construct as a whole, the material of the substrate depends on the particular nature of the intended location of the construct in the subject according to the therapeutic use for which it is to be employed, as is readily apparent to those skilled in the art. For example, the material of the substrate may be adapted to serve as a delivery vehicle of one or more growth factors and/or may be adapted to serve as a structural or physical support or scaffold for regenerating tissue.

Also in a similar manner as described herein for the construct as a whole, the conformation of the substrate depends on the particular nature of the intended location of the construct in the subject according to the therapeutic use for which it is to be employed, as is readily apparent to those skilled in the art. For example, the conformation of the substrate may be adapted to serve as a structural or physical support or scaffold for regenerating tissue. For example, the substrate may be adapted to fit the target site in the subject. The substrate may be planar or may be a complex 3D shape.

In certain embodiments, the substrate is an implant, for example an orthopaedic implant or a dental implant.

In a particular example, the substrate may be a biocompatible porous material having a conformation adapted to fit between the damaged ends of a critical size bone defect, e.g. a hollow tube or sleeve. In a particular example, the substrate may be a biocompatible porous material having a conformation adapted to fit around (e.g. overlay) the damaged area in a bone fracture, e.g. to form a hollow tube or sleeve. In a particular example, the substrate may be a biocompatible metal or alloy having a conformation adapted to fit internally or adjacent to a damaged bone or bone fragments, e.g. a rod or plate, such as a commercially available orthopaedic implant. In a particular example, the substrate may be a biocompatible porous material having a conformation adapted to fit around (e.g. overlay) or between two adjacent vertebrae to be fused. In a particular example, the substrate may be a biocompatible hydrogel or polymer matrix having a conformation adapted to provide a scaffold to support and direct a developing vascular network.

Suitable substrates for in vivo therapeutic implants are described in the art (e.g. 59, 60).

The alkyl acrylate polymer layer (and thus the FN layer) may cover the entirety of a first surface. Alternatively the alkyl acrylate polymer layer (and thus the FN layer) may be in the form of a discontinuous (patchy) layer across the entirety of a first surface or cover only a portion of a first surface.

Corresponding considerations, e.g. as to material and conformation of the substrate, apply when the biocompatible substrate is for in vitro cell culture use. For example, the substrate may be adapted to serve as a structural or physical support or scaffold for cells growing in culture, e.g. a biocompatible porous polymer matrix.

The material surface may comprise, consist essentially of, or consist of an alkyl acrylate polymer.

The alkyl acrylate polymer forming the material surface is capable of supporting the formation of a physiological fibrillar network of FN adsorbed on its surface. Thus, FN has the conformation of a physiological fibrillar FN network upon adsorption on an alkyl acrylate polymer surface according to the invention.

An alkyl acrylate polymer may be referred to herein also as poly(alkyl acrylate) or (alkyl acrylate)$_n$. An alkyl acrylate polymer for use in the construct is a polymer of the general formula $—(C—C—COO(CH_2)_xCH_3)_n$ where x=1, 2, 3, 4, 5, 6, 7, 8, 9 or 10 . . . etc. In the formula, n designates the number of monomer units making up the polymer. For example, the alkyl acrylate polymer may be a member of the group of polymers having the formula $—(C—C—COO(CH_2)_xCH_3)_n$ where x=1 to 5. For example, the alkyl acrylate polymer may be a member of the group of polymers having the formula $—(C—C—COO(CH_2)_xCH_3)_n$ where x=1, 3, or 5. For example, the alkyl acrylate polymer preferably is poly(ethyl acrylate) (PEA) having the formula $CH_2CHCO_2CH_2CH_3$, i.e., where x=1 in the general formula. The alkyl acrylate polymer may be poly(butyl acrylate) (PBA) having the formula $—(CH_2CHCOO(CH_2)_3CH_3)_n$, i.e., where x=3 in the general formula. The alkyl acrylate polymer may be poly(hexyl acrylate) (PHA) having the formula $—(CH_2CHCOO(CH_2)_5CH_3)_n$, i.e., where x=5 in the general formula. The general formula above may also be written as $—[CH_2—CH—(COO(CH_2)_xCH_3)]_n—$ where x=1, 2, 3, 4, 5, 6, 7, 8, 9 or 10 . . . etc., where in the formula, n is an integer and designates the number of monomer units making up the polymer.

The alkyl acrylate polymer may be a co-polymer or blend of an alkyl acrylate producing a polymer capable of supporting the formation of a physiological fibrillar network of FN upon adsorption on its surface as described herein and any other monomer. For example, a co-polymer or blend may comprise an alkyl acrylate polymer capable of supporting the formation of a physiological fibrillar network of FN upon adsorption on its surface and an alkyl acrylate polymer which alone is not capable of supporting the formation of a physiological fibrillar network of FN adsorbed on its surface. PEA is a generally preferred first component of such a copolymer or blend, or alternatively PBA or PHA. PMA is a generally preferred second component of such a copolymer or blend.

The alkyl acrylate polymer capable of inducing FN fibrillogenesis is present in the copolymer or blend in a sufficiently high amount to provide its function of supporting FN fibrillogenesis as may be determined by those skilled in the art, for example using methods as described herein. Generally, the amount of alkyl acrylate polymer capable of inducing FN fibrillogenesis in the copolymer or blend is at least about 50%, is > about 50%, or is ≥ about 70%, for example is at least about 50% by weight, is > about 50% by weight, or is ≥ about 70% by weight. For example, the copolymer may be PEA/PMA (70%/30%), PEA/PMA (60%/40%) or PEA/PMA (50%:50%). The copolymer may be PEA with any one of PMA, polyacrylic acid (PAAc), polycaprolactone, polylactic acid, or polyacrylamide (PAAm), for example.

The alkyl acrylate polymer is substantially free of low molecular mass substances. Alkyl acrylate polymers such as PEA are stable polymers in physiological solutions and environments. For example, PEA has a glass transition temperature of about −20° C. The alkyl acrylate polymer, such as PEA or a copolymer thereof, is cell-free.

The alkyl acrylate polymer surface is deposited as a thin (sub micron) layer surface on the substrate.

The biologically active matrix comprises fibronectin (FN) and one or more growth factors (GF). The biologically active matrix is cell-free. FN and one or more growth factors together provide a biologically active matrix assembled on the polymer surface of the construct.

The fibronectin has the conformation of a physiological fibrillar FN network upon adsorption on the polymer surface. The FN is cell-free. Without being bound by any particular theory, adsorption of FN onto the alkyl acrylate polymer surface induces exposure of self-assembly sites ($FNI_{1-5}$) in FN to drive fibrillar FN assembly at the interface with the polymer surface. The process involves the 70 kDa amino acid fragment of FN, which is the hallmark of physiological cell-induced FN fibrillogenesis.

The FN presents a growth factor-binding site of FN in combination with an integrin binding site of FN. The FN presents a growth factor-binding site of FN in combination with an integrin binding site of FN in a conformation favouring simultaneous availability of said growth factor-binding site and integrin binding site for binding. The FN is in a conformation that favours the simultaneous availability of the growth factor (GF) binding domain ($FNIII_{12-14}$) next to the integrin binding domain ($FNIII_{9-10}$). The FN comprises FN fibrils in which the growth factor (GF) binding domain ($FNIII_{12-14}$) is colocalized with an integrin binding domain. The FN comprises fibrils in which $FNIII_{12-14}$ is colocalized with $FNIII_{9-10}$.

The FN growth factor-binding domain is bound by one or more growth factors capable of binding the FN growth factor-binding domain.

Thus the biologically active matrix comprises a physiological fibrillar FN network, in which the growth factor binding domain of FN and an integrin binding site of FN are present in a conformation favouring simultaneous availability of said growth factor-binding domain and integrin binding site for binding, and one or more growth factors bound to said growth factor-binding domain.

The biologically active matrix presents binding sites for one or more growth factor receptors in combination with binding sites for one or more integrins to favour cell signalling to direct cell growth, proliferation and/or differentiation, e.g. cell differentiation. The biologically active matrix presents binding sites for one or more growth factor receptors and for one or more integrins in a cell-exploitable conformation. The biologically active matrix presents colocalized binding sites for one or more growth factor receptors and for one or more integrins to favour cell signalling to direct cell growth, proliferation and/or differentiation e.g. cell differentiation.

The biologically active matrix presents one or more growth factors and an integrin binding site of FN in a conformation favouring simultaneous availability for binding by one or more growth factor receptors and one or more integrins, respectively. The biologically active matrix presents one or more growth factors in combination with an integrin binding site of FN in a conformation favouring cell signalling by growth factor receptors and integrins to direct cell growth, proliferation and/or differentiation e.g. cell differentiation. The biologically active matrix presents one or more growth factors and an integrin binding site of FN in a cell-exploitable conformation. The biologically active matrix is capable of colocalizing growth factor receptors and integrins favouring cell signalling to direct cell growth, proliferation and/or differentiation e.g. stem cell differentiation.

An integrin binding site of FN may be within the FN integrin binding domain ($FNIII_{9-10}$). FN also contains other integrin binding sites, extradomain A (EDA) and a variable domain (V) (FIG. 5a). A GF binding site is within the FN growth factor binding domain ($FNIII_{12-14}$).

The biologically active matrix favours coordinated cell signalling by one or more growth factor receptors and one or more integrins. The biologically active matrix favours synergistic cell signalling by one or more growth factor receptors and one or more integrins. Coordinated or synergistic cell signalling serves to drive or enhance cell growth, proliferation and/or differentiation, tissue regeneration or growth, treatment of injury or disease.

The fibronectin may be any fibronectin suitable for in vivo use or for in vitro cell culture use. In certain embodiments, the FN is isolated human FN. The FN may be recombinant human FN. The FN may be isolated plasma or cellular FN. The FN may be isolated from the recipient subject of the construct.

A growth factor may be any growth factor suitable for in vivo use or for in vitro cell culture use. In certain embodiments, the GF is an isolated human GF. The GF may be a recombinant human GF. The GF may be isolated from the recipient subject of the construct.

A growth factor is capable of binding a growth factor-binding domain of FN. A growth factor is capable of binding $FNIII_{12-14}$. In certain embodiments, the growth factor is BMP-2 or VEGF. A growth factor may be BMP (e.g. BMP-2 or BMP-7), VEGF, PDGF (e.g. PDGF-BB), TGF (e.g. TGF-β) or a neurotrophic GF.

The biologically active matrix may further comprise one or more additional ECM components, e.g. vitronectin (VN), collagen IV, laminin. These may be any ECM components suitable for in vivo use or for in vitro cell culture use. In certain embodiments, the ECM component is an isolated human ECM component. The ECM component may be a recombinant human ECM component. The ECM component may be isolated from the recipient subject of the construct.

For therapeutic use, the construct is implantable, for example in a subject in need of cell signalling favoured by the biologically active matrix, to direct cell growth, proliferation and/or differentiation or tissue regeneration or growth, for the treatment of injury or disease or use therein for example. The construct when implanted may also serve as a temporary structural or physical support or scaffold for regenerating tissue.

The construct is for implanting at a location in a subject depending on the particular nature of the construct and the therapeutic use for which it is to be employed, in particular in the context of the biocompatible substrate and/or the one or more growth factors of the biologically active matrix of the construct, as is readily apparent to those skilled in the art. For example, the construct is for implanting at a target site such as a site of injury or disease consistent with, for example, the size, shape, structure, overall conformation, material of the substrate of the construct. For example, the construct is for implanting at a target site such as a site of injury or disease consistent with a particular GF used in the construct. In certain embodiments, the construct is for implanting at a site of bone damage, e.g. from injury or disease, for example at a site of a bone fracture or a critical size bone defect, for treatment of the bone damage. In certain embodiments, the construct is for implanting at a site requiring vascularization, e.g. where there is tissue damage or tissue regeneration at a site of injury or disease, for example at a wound site, for wound healing or treatment of the wound or disease.

The nature of suitable constructs for implantation at a particular location in a subject and/or for a particular therapeutic use, in terms of the biocompatible substrate and/or the one or more growth factors of the biologically active matrix of the construct, is readily apparent to those skilled in the art. For example, those skilled in the art are well aware of biocompatible substrates suitable for implantation at a site of injury or disease, e.g. bone damage, for treatment of the injury or disease, in terms of suitable materials and suitable overall conformation, depending on the nature and site of the injury and disease. Thus the construct may comprise a biocompatible substrate of any material suitable for implantation in vivo or for in vitro cell culture use, as are known in the art and understood by those skilled in the art. Thus the construct may comprise a biocompatible substrate of any overall conformation suitable for implantation in vivo or for in vitro cell culture use, as are known in the art and understood by those skilled in the art.

The construct thus has an overall conformation depending on the particular nature of the intended location in the subject according to the therapeutic use for which it is to be employed. For example, the construct may be planar or may be a complex 3D shape. In certain embodiments, the construct is based on an implant, such as an orthopaedic implant.

For therapeutic applications, the particular nature of the cell signalling, cell growth, proliferation and/or differentiation, tissue regeneration or growth, injury and disease depends on the nature of the one or more growth factors in the biologically active matrix, as will be readily apparent to those skilled in the art and as described herein.

In a particular example, as described in detail herein, a construct comprising the growth factor BMP-2 has utility to direct mesenchymal stem cell (MSC) differentiation and bone regeneration or growth (i.e. osteogenesis) for use in bone related surgical procedures or for treatment of bone damage. For example, for treatment of bone fracture or critical size bone defects after trauma or cancer, for spinal fusion, in orthopaedic implants to promote integration with bone.

In a particular example, as described in detail herein, a construct comprising the growth factor VEGF has utility to direct vascularization for use in treating tissue damage, for example in wound healing.

The construct may be introduced to the target site by a surgical procedure. Methods and considerations for surgically introducing a therapeutic implant into a subject are well known in the art and understood by those skilled in the art. The construct may be introduced to the target site by injection or infusion, e.g. where the construct is in the form of a composition comprising particles.

Corresponding considerations, e.g. as to biocompatible substrate (material and conformation of the substrate) and/or the one or more growth factors of the biologically active matrix of the construct, apply when the construct is for in vitro cell culture use. For example, the construct may be adapted to serve as a structural or physical support or scaffold for cells growing in culture.

Constructs may be prepared using the following methods or any described herein.

A method of preparing an implantable construct as described herein may generally comprise the steps of: depositing an alkyl acrylate polymer on a first surface of a biocompatible substrate to form a material surface; applying fibronectin and a growth factor to said material surface to form a biologically active matrix. A method of preparing an implantable construct as described herein, may generally comprise the steps of: providing a biocompatible substrate having a first surface; depositing an alkyl acrylate polymer on said first surface to form a material surface; applying fibronectin and a growth factor to said material surface to form a biologically active matrix.

The method of preparing the construct is cell-free.

The alkyl acrylate polymer surface is deposited as a thin (sub micron) layer surface on the substrate. The alkyl acrylate polymer may be spin-coated onto the substrate. The alkyl acrylate polymer may be plasma polymerized onto the substrate. The alkyl acrylate polymer may be sprayed onto the substrate. The alkyl acrylate polymer may be polymerized onto the substrate by chemical synthesis routes.

The FN and GF are adsorbed from solution onto the alkyl acrylate polymer material surface. In certain embodiments, the FN and GF are applied sequentially, with the FN applied before the GF. In certain embodiments, the FN and GF are applied concomitantly.

The step of applying fibronectin and a growth factor to said material surface to form a biologically active matrix may further comprise applying to said material surface a further ECM component capable of forming a biologically active matrix when applied to said material surface, e.g. vitronectin (VN), collagen IV, laminin. The further ECM component is adsorbed from solution onto the alkyl acrylate polymer material surface. The further ECM component may be applied sequentially or concomitantly with respect to the FN and/or GF.

Material surfaces of the constructs may be prepared with the desired poly(alkyl acrylate) surface coating, for example, a poly(ethyl acrylate) (PEA) coating, deposited on the desired substrate. Polymer sheets may be obtained by radical polymerization of a solution of the corresponding alkyl acrylate monomer, e.g., ethyl acrylate (Sigma-Aldrich), or blend of monomers for a copolymer surface coating as described herein, using about 0.2 to 1 wt % benzoin (98% pure, Scharlau) as a photoinitiator. The polymerization is carried out up to limiting conversion. After polymerization, low molecular-mass substances are extracted from the polymer by drying in vacuo to constant weight. Thin films may be prepared by making use of a spin-coater (Brewer Science). The synthesized polymer is dissolved in toluene at a concentration of about 1 to 4 wt %. Spin casting is performed on the substrate, for example a 12 mm glass coverslip, at 2000 rpm for 30 s. Samples are dried in vacuo at 60° C.

The polymer surface coating on the substrate may be prepared by plasma polymerization on the substrate. A plasma chamber at low pressure may be used to prepare the polymer surface coating by plasma polymerization onto a substrate. A plasma system is needed that is able to work at low pressure (lower than $2 \times 10^{-2}$ mbar at some stages of the process), and that is able to work with fine control of emitted and reflected power (under 50 Watt). The desired polymer, e.g., ethyl acrylate (>98% purity), should be stored at 4° C. before use. Substrate surfaces are cleaned and dried with a suitable method before starting the plasma polymerization protocol. For example, porous polymer substrates may be simply blown with a compressed air gun. For example, glass or metal substrates may be cleaned in ethanol in a sonication bath and dried at 60° C. before their use. Substrate samples are then placed in a tray inside the plasma chamber. The plasma polymerization protocol includes several stages of varying length depending on the expected coating properties. These stages generally comprise vacuum pumping, $O_2$ activation, and plasma polymerisation. Depending on the substrate material, a preliminary treatment in an oxygen plasma may improve the final properties of the product. This treatment generally requires short exposure (1-5 minutes) at low power (around or lower than 100 Watt). For example, plasma polymerisation of ethyl acrylate is generally achieved with good results starting at a pressure lower than $2 \times 10^{-2}$ mbar and increasing the monomer flow up to a chamber pressure of around $1 \times 10^{-1}$ to $2 \times 10^{-1}$ mbar, and a power output lower than 100 Watt. Deposition ratios of 3 to 7 µm of PEA per minute are generally accomplished.

The polymer surface coating on the substrate may also be prepared by spraying the polymer with a carrier gas or chemical polymerization such as Atomic Transfer Radical Polymerisation (ATRP).

Fibronectin (FN), e.g. from plasma or recombinant sources, is then adsorbed on the polymer surface-coated substrate by immersing the surfaces in a solution of FN, at concentrations from about 2 to 20 µg/ml for example, in phosphate-buffered saline (PBS). After adsorption, surfaces are rinsed in PBS to eliminate the non-adsorbed protein. Atomic force microscopy (AFM) may be performed in the tapping mode immediately after adsorption to verify FN fibrillogenesis. The FN has the conformation of a physiological fibrillar FN network upon simple adsorption, without application of external force, on the polymer surface of the construct.

A desired GF is adsorbed on the surface by immersing the surface in a solution of GF, at concentrations from about 5 ng/ml to 5 µg/ml for example, in Dulbecco's phosphate-buffered saline (DPBS). For example, BMP-2, e.g. from recombinant sources, may be adsorbed on the surface by immersing the surface in a BMP-2 solution in DPBS at a concentration of from 5 ng/ml to 5 µg/ml. For example, VEGF, e.g. from recombinant sources, may be adsorbed on the surface by immersing the surface in a VEGF solution in PBS (e.g., 25 ng/ml) for 1 hour. After adsorption, surfaces are rinsed in PBS to eliminate the non-adsorbed protein.

Presence of GF on the substrate may be assayed directly by AFM, using an immunogold reaction. AFM may be performed in the tapping mode immediately after adsorption and washing to verify that GF is sequestered by the (nano) network of FN fibrils assembled on the polymer surface. Presence of GF on the substrate may be assayed indirectly by measuring remaining GF in the coating solution using a sandwich ELISA. The FN and GF together provide a biologically active matrix assembled on the polymer surface of the construct.

A further ECM component capable of forming a biologically active matrix with the FN and GF when applied to said polymer surface, e.g. vitronectin (VN), collagen IV, laminin, may be applied in a similar way as described for FN and GF, i.e. by adsorption. Thus a further ECM component may be adsorbed onto the surface by immersing the surface in a solution of the ECM component, at concentrations from about 2 to 20 µg/ml for example, or from about 5 ng/ml to 5 µg/ml, for example, in PBS or DPBS.

Preparation of the construct is cell-free. Prepared constructs may be used immediately or stored to preserve biological integrity and effectiveness of the components, as known in the art and as will be understood by those skilled in the art.

The invention will now be described in more detail, by way of example and not limitation, by reference to the accompanying drawings and examples.

DESCRIPTION OF THE DRAWINGS

FIG. 3. Integrin co-ligation with BMP-2 receptor and differential signalling. a. Co-IP of integrin β1 and BMP-2 receptor I occurred on BMP-2 sequestered by FN on PEA and was prevented by blocking the GF binding domain of FN (using P5F3 against FNIII12-14) before BMP-2 adsorption. b. Phosphorylation of ERK1/2 was significantly enhanced on PEA when BMP-2 was presented at the material interface, sequestered on FN, compared to the presence of the same doses of the soluble factor. c. Smad signalling was drastically altered when BMP-2 was presented bound on FNIII12-14; blocking this GF binding domain of FN reduces Smad signalling. Results show mean±SD, n=9. Symbols show statistical significant differences with all the other conditions on PEA (* p 0.001, ¥ p 0.01).

Figure 4:
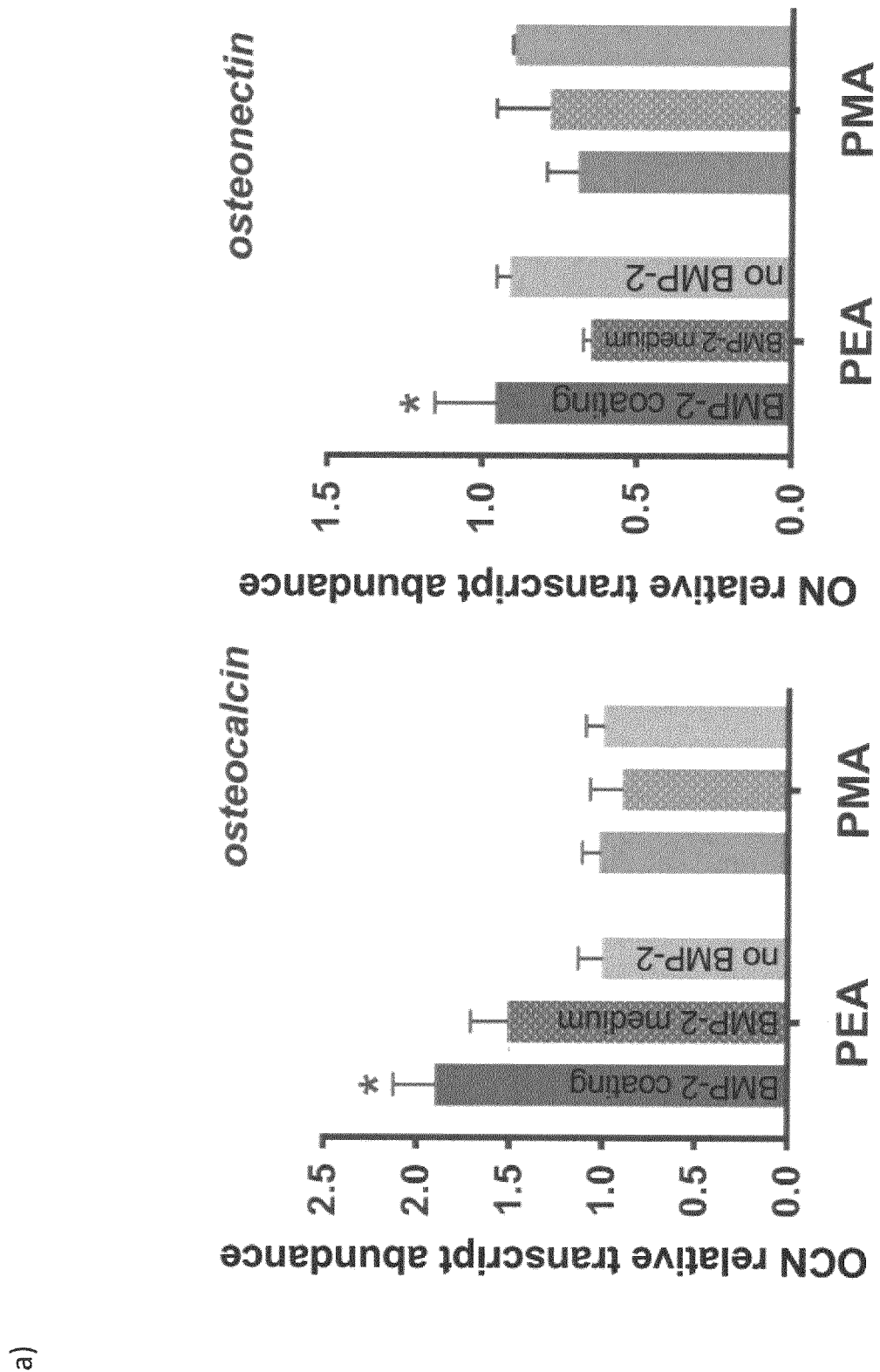
Figure 4:
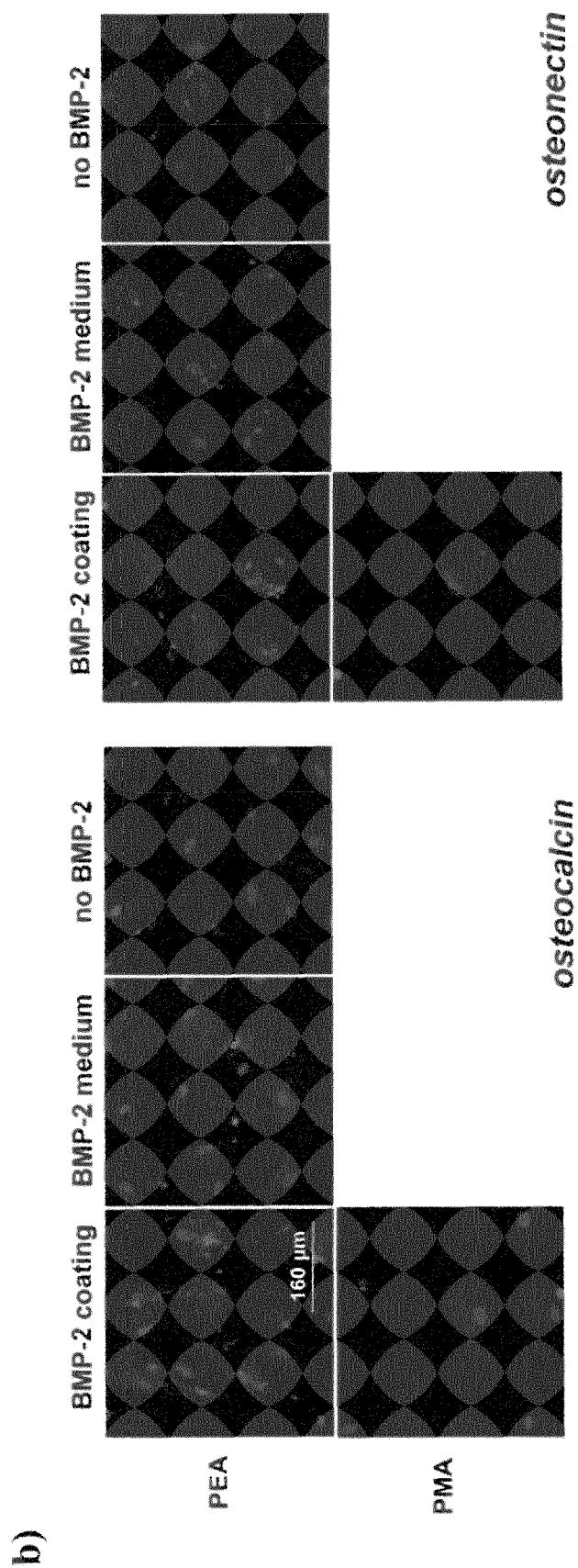
Figure 4:
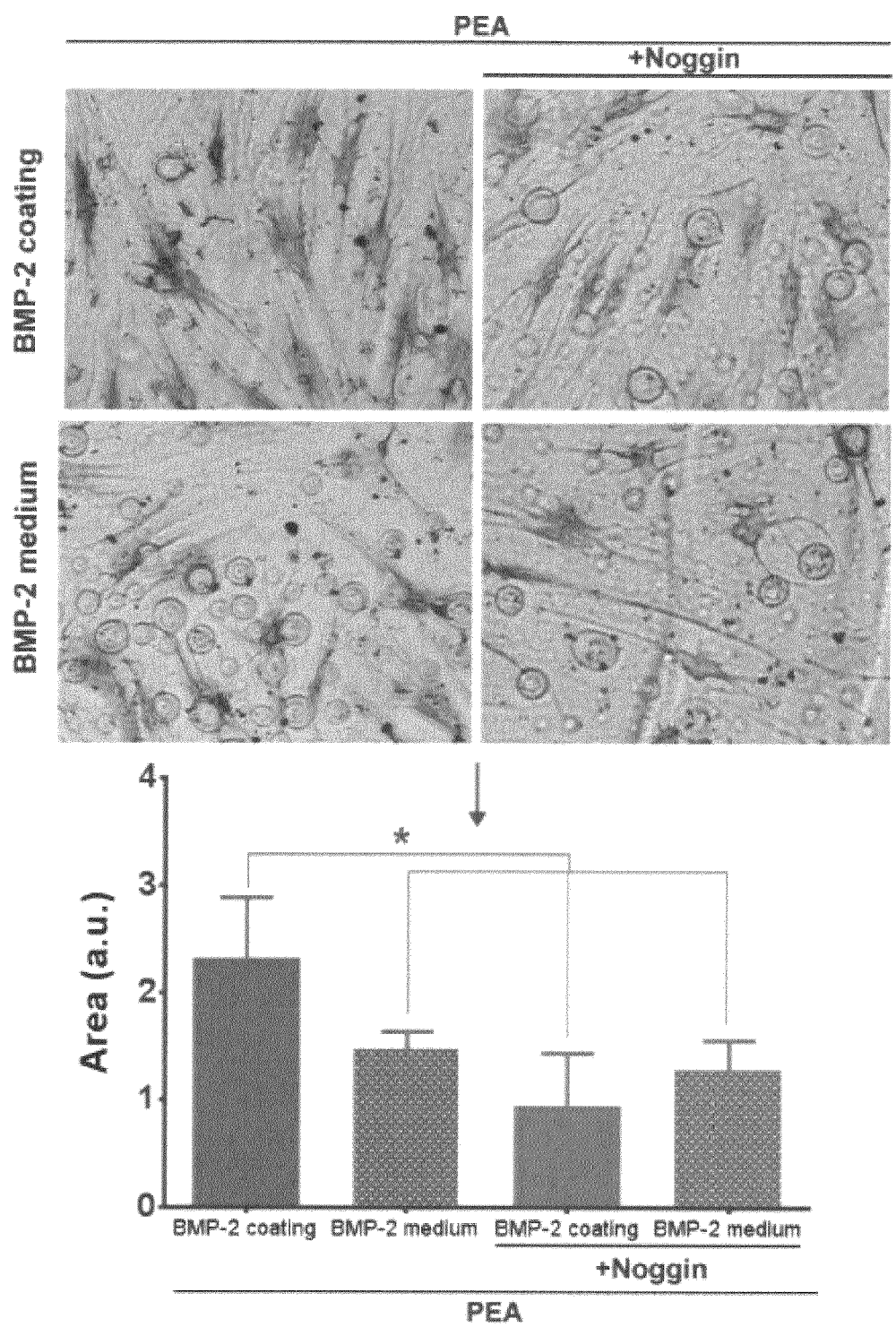

FIG. 4. Osteogenic differentiation on BMP-2 bound to FN (nano)networks. a. qPCR for osteocalcin and osteonectin after 14 days of culture. Enhanced expression occurs when BMP-2 was presented bound on FN compared to soluble administration of the GF or when BMP-2 was sequestered on the material surface (PMA) but not bound to FN. b. Immunofluorescence for osteocalcin and osteonectin confirmed results obtained at the gene level (red=osteocalcin/osteonectin, blue=DAPI). Results show mean±SD, n=9. Symbols show statistical significant differences with all the other conditions (* p 0.001, ¥ p 0.01). c. ALP staining on PEA comparing BMP-2 bound on FN fibrils versus soluble BMP-2. Noggin (50 ng/ml) was used in both conditions as BMP-2 inhibitor to prevent activity (image quantification included in the graph). Results show mean±SD (n=3 for all experiments except in c. where 9 images were used). The Tukey-Kramer method was used with multiple-comparisons post-test analysis of variance (ANOVA). Symbols show statistical significant differences with all the other conditions (* p 0.001, ¥ p 0.01).

Figure 5:
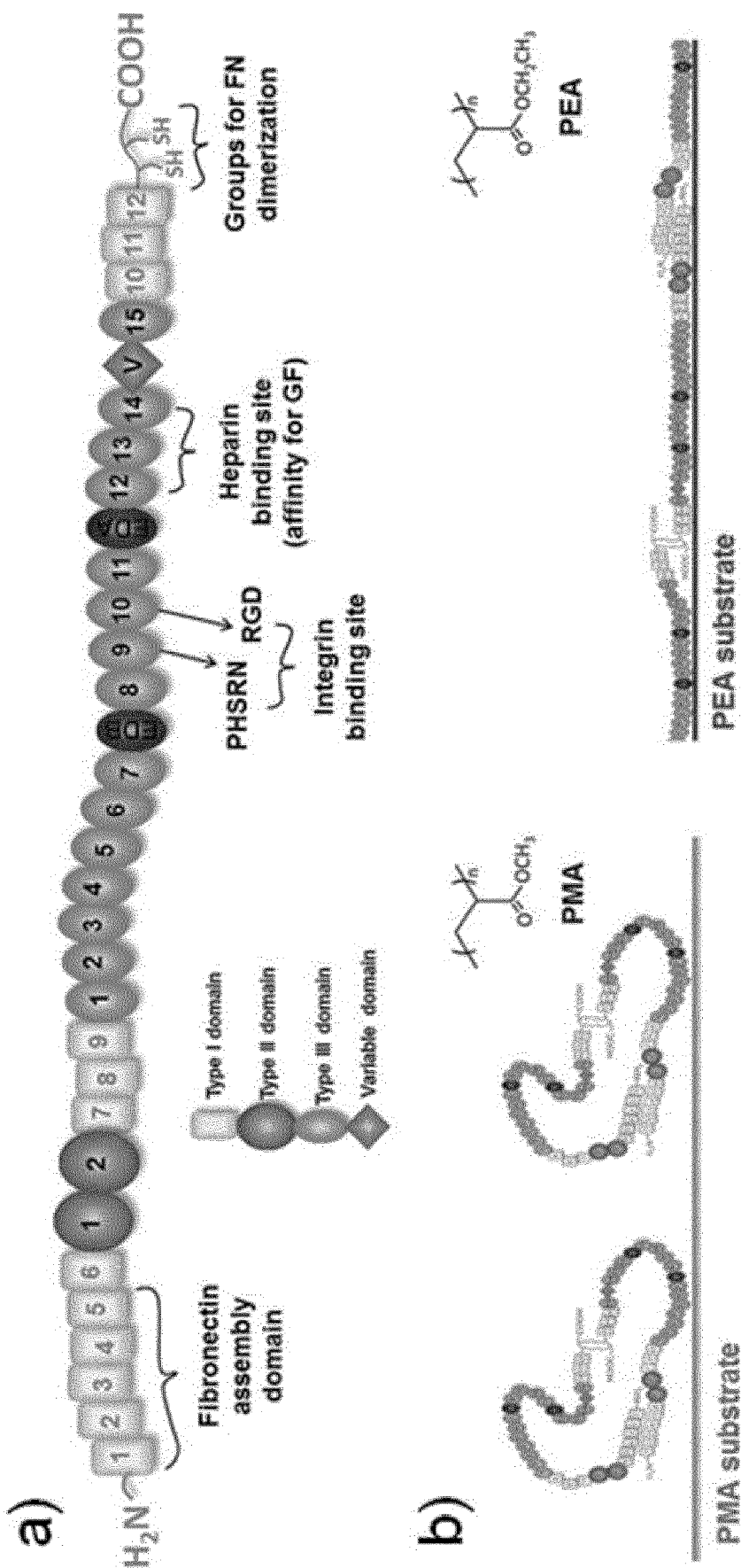
Figure 5:
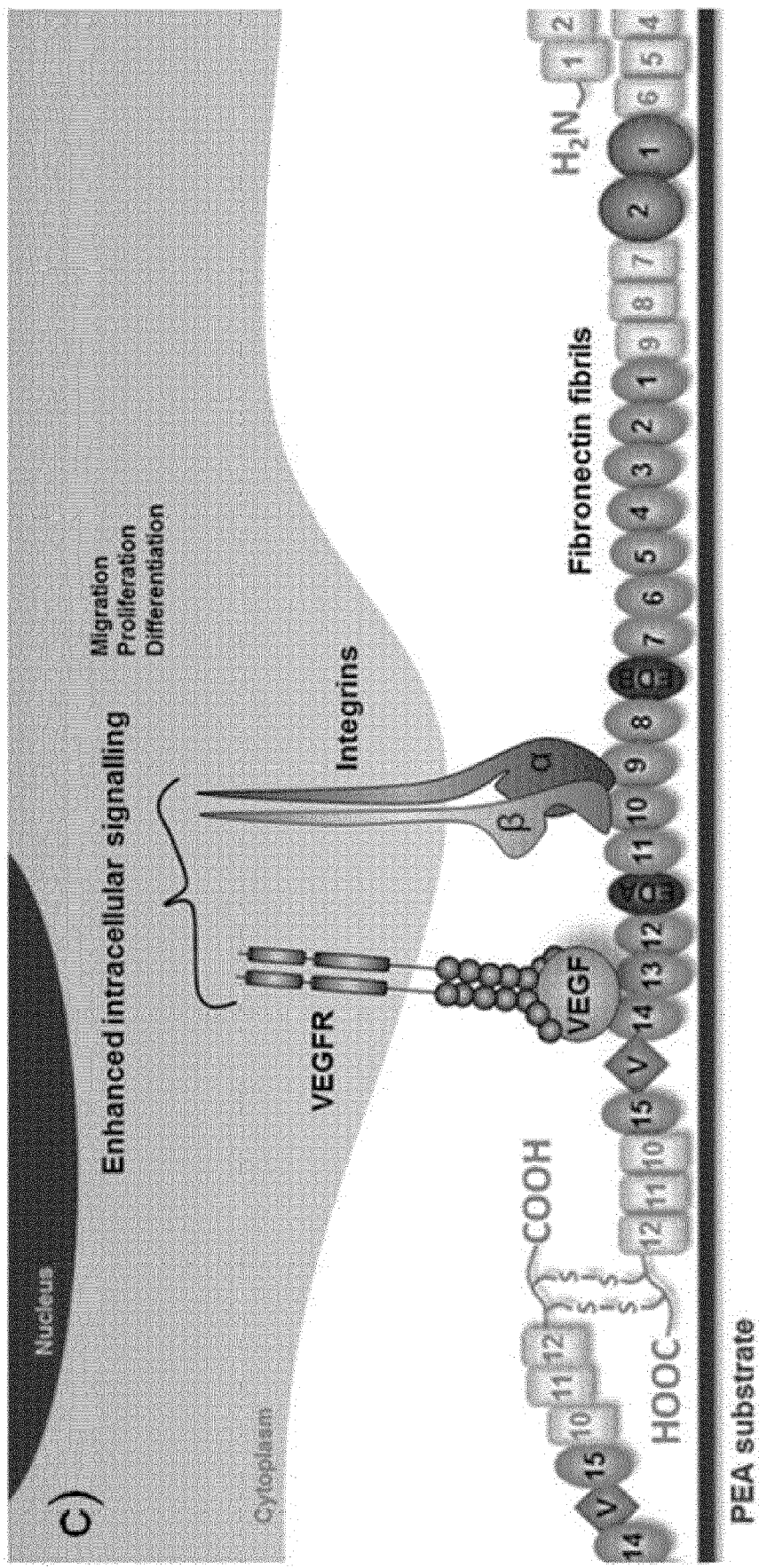

FIG. 5. Conceptual image of material-driven FN fibrillogenesis. a. FN molecule with depicted domains. b. FN assembly on two different polymer substrates; on PMA the FN stays in globular conformation, on PEA FN fibrillogenesis is triggered and FN network is formed; c. Scheme of synergistic effect of FN functionalized with VEGF on cell signaling: the presentation of VEGF bound to FN in close vicinity of integrin binding sites effectively enhances out-in signaling and allows to VEGF receptor (VEGFR) and integrins to work in synergy.

Figure 6:
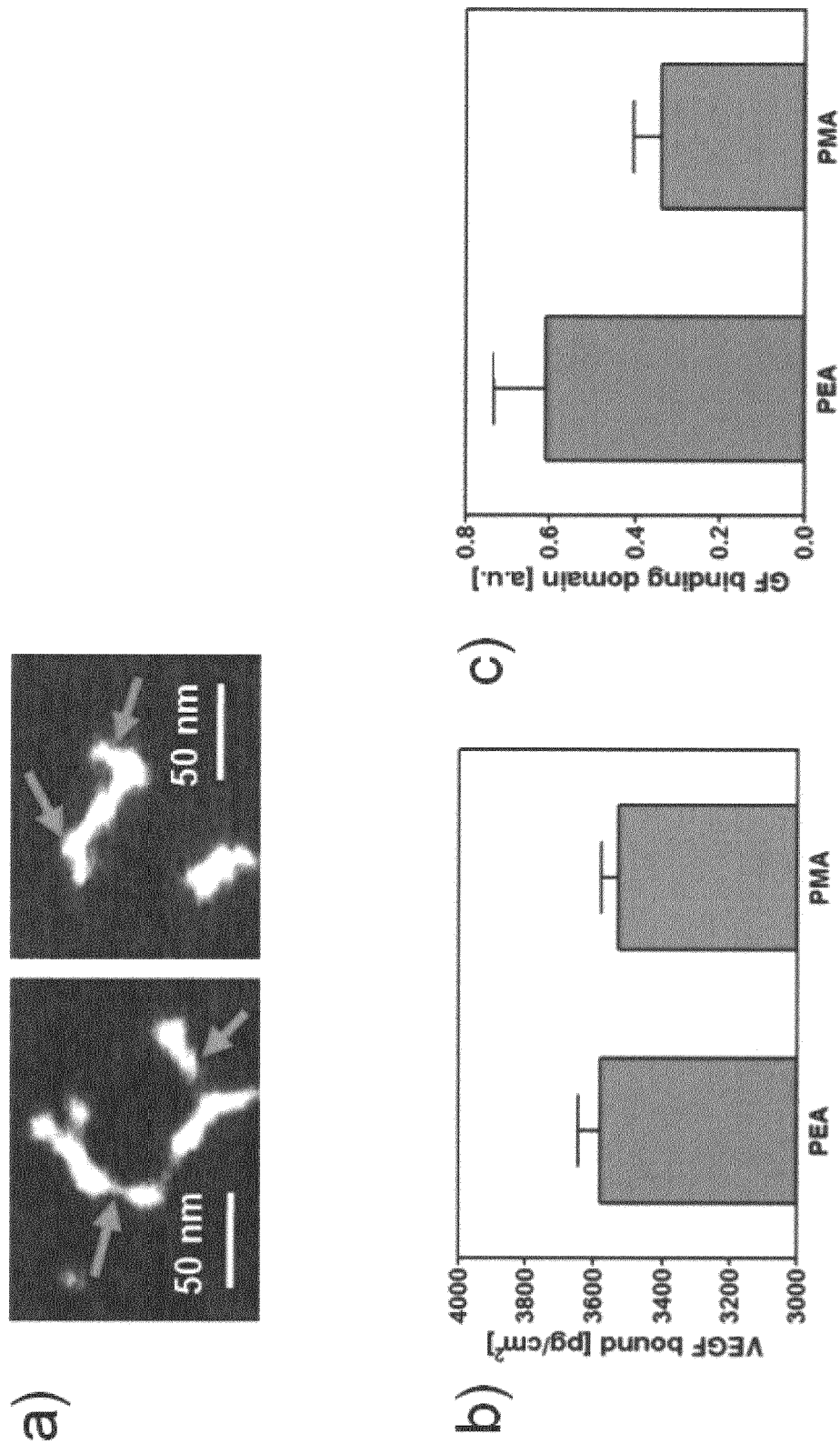
Figure 6:
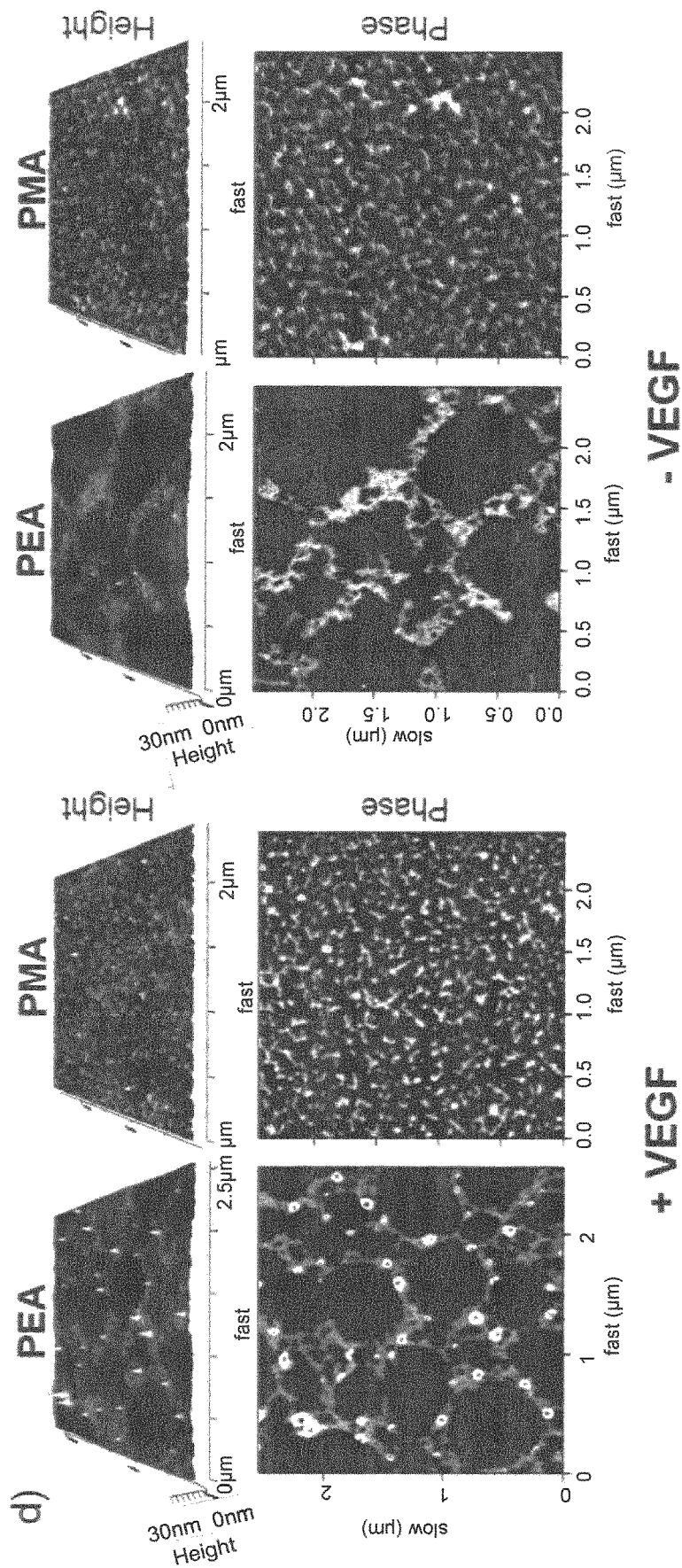

FIG. 6. Characterization of VEGF binding to biosynthetic substrates. A. AFM images of FN-coated PEA incubated with (right) and without (left) VEGF: images are showing stretched FN molecules (with monomer length ~50 nm); blue arrows (left) depict approximate position of $FNIII_{12-15}$ domains (GF binding site) with no GF present; green arrows (right) shows thickening of FN fibers where $FNIII_{12-15}$ domains are located, suggesting presence of VEGF molecule. b. and c. Comparison of VEGF amount bound to FN-coated substrates: b. although ELISA did not show significant difference between VEGF bound to PEA and PMA surfaces, c. the availability of GF binding domains is significantly higher on the PEA surface which suggests higher level of non-specific VEGF binding with the PMA surface. d. AFM imaging of FN-coated substrates after immunogold reaction with VEGF in presence of the GF (left) and without the GF (right): white peaks represent VEGF bound to PEA while no VEGF was detected on PMA (left); only FN network (PEA) or scattered FN molecules (PMA) are visible on VEGF negative controls (right). Multiple washes necessary for this experiment can explain that VEGF non-specifically bound to PMA (and detected by ELISA) was removed, while specific binding to PEA was not affected.

Figure 7:
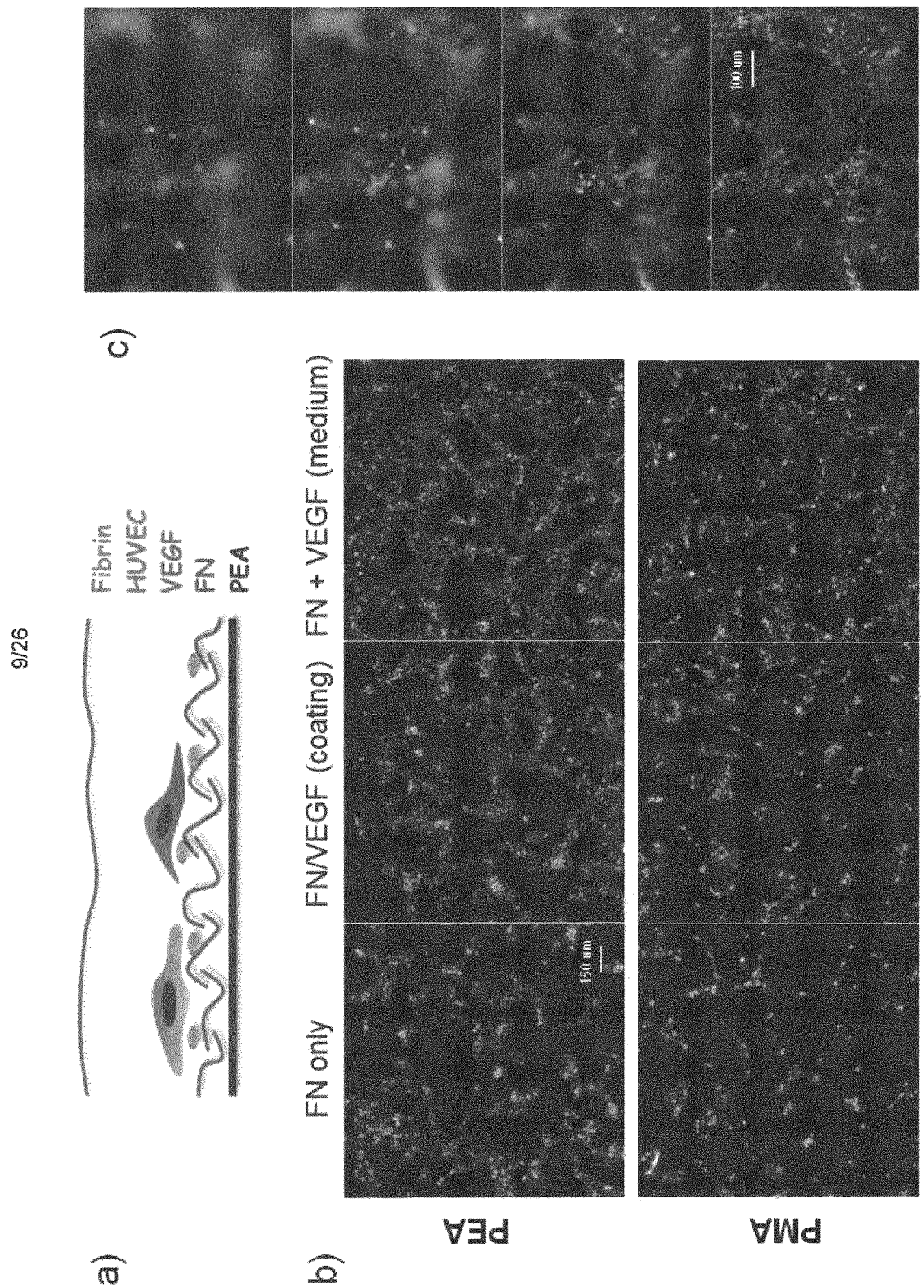

FIG. 7. HUVEC forming network structures on functionalized substrates. a. Scheme of system components: after polymers were coated with FN and GF, cells were seeded on the top, and finally covered with thin layer of fibrin matrix. b. Fluorescence images of cell cultures after 6 days of incubation: FN/VEGF-coated PEA showed better cell attachment and higher degree of aligned structures in comparison to PMA treated in the same way (central images); negative controls (samples with no GF coating) and positive controls (samples with no GF coating but with VEGF constantly present in media) are also shown (left and right, respectively). c. Stack images showing 3D sprouting of HUVEC cells into fibrin matrix: bottom image is at the level of synthetic polymer substrate, height difference between bottom and top image is 200 µm.

Figure 8:
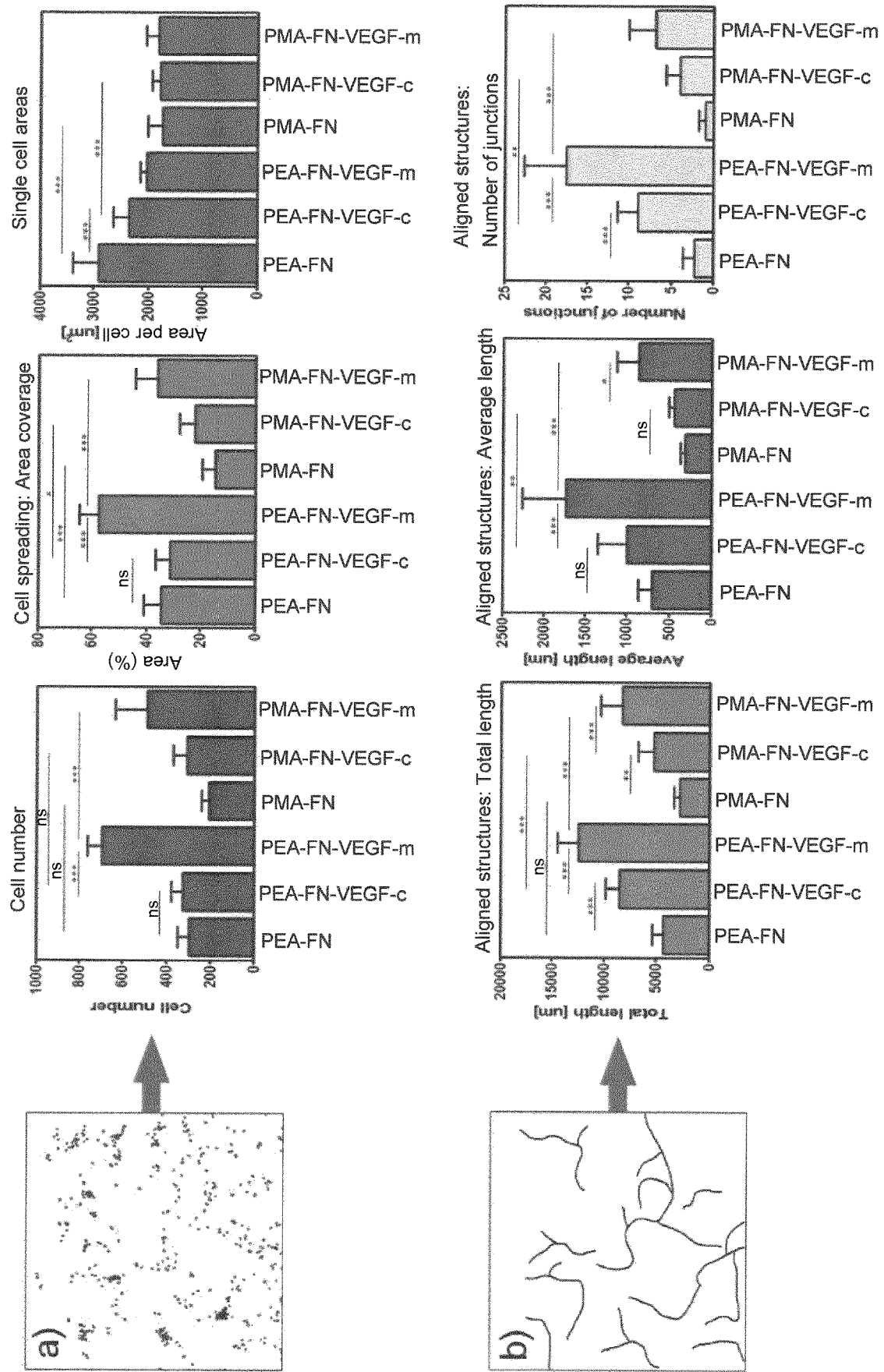

FIG. 8. Image analysis of HUVEC behaviour on functionalized substrates. a. A merged image of a DAPI staining and a mask from actin staining: these raw images were used for quantification of cell count and cell spreading after 6 days of incubation. The cell number (blue bars) did not vary apart from "FN-VEGF-m" controls (FN-coated polymer substrates with VEGF present in medium); the total area coverage (green bars) was higher on PEA surfaces when compared to PMA surfaces for individual conditions: FN coated only (FN), FN and VEGF coated (FN-VEGF-c), and FN-coated with VEGF in medium (FN-VEGF-m), showing better cell adhesion and spreading on PEA-FN surfaces. This is supported by larger single cell area (grey bars) on PEA surfaces when comparing PEA-FN vs. PMA-FN and also PEA-FN-VEGF-c vs. PMA-FN-VEGF-c. An observation that in the case of PEA surfaces single cell area decreased when VEGF was present while for all PMA surfaces stayed constant, suggests that individual cells can cover a smaller area when in a higher level of cell organization. b. Simplified binary image of actin staining used for quantification of cell organization. Statistical analysis of total length of aligned structures per image (orange bars) as well as an average length of these structures (red bars) including number of junctions per image (cream bars) showed higher level of cell alignment on PEA-FN-VEGF samples when compared to their respective PMA-FN-VEGF controls. Total length and number of junctions were significantly higher in PEA-FN-VEGF-c samples when compared to no-GF PEA control (PEA-FN) which clearly shows a vasculogenic effect of VEGF coating. One way ANOVA with Tukey's multiple comparison post-test was carried out for statistical analysis; * P<0.05;  P<0.01; * P<0.001; ns=non-significant.

Figure 9:
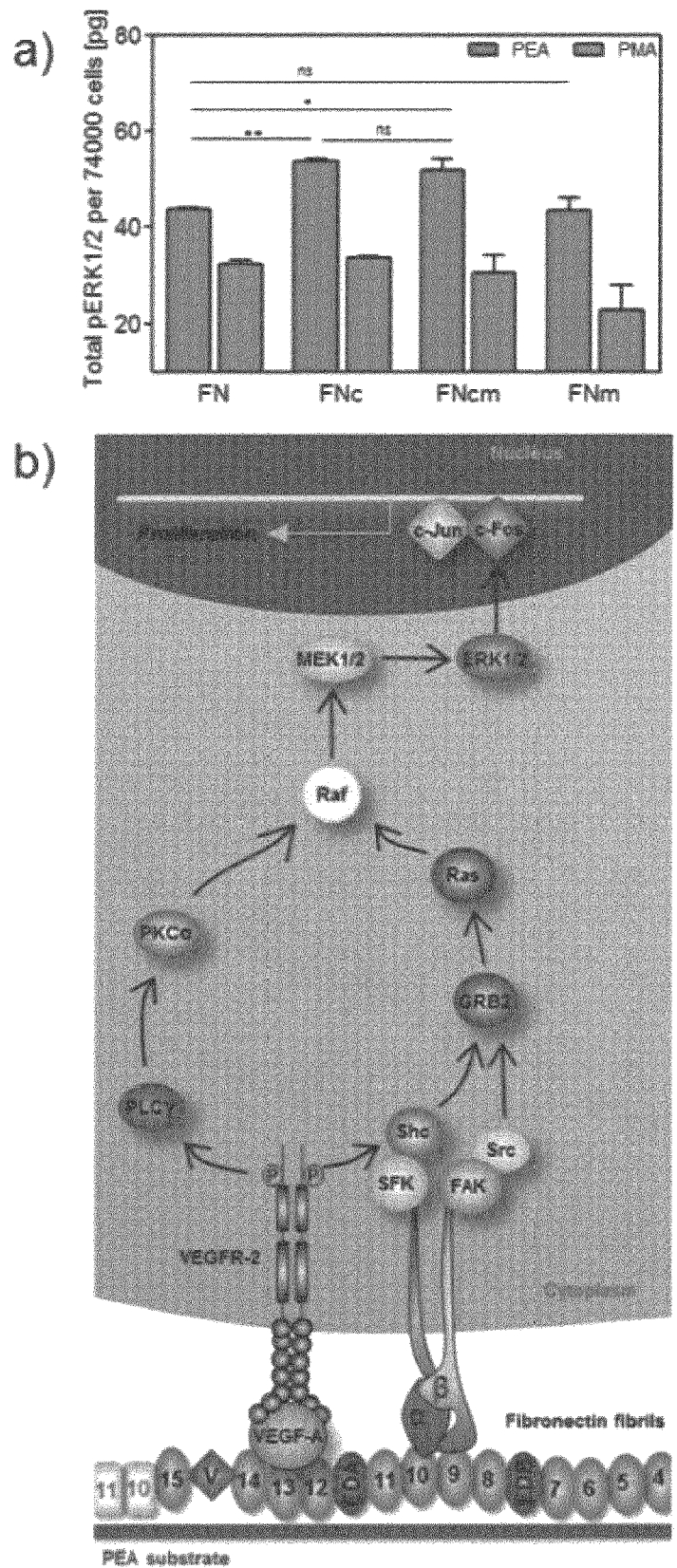

FIG. 9. ERK1/2 phosphorylation in HUVEC. a. ELISA quantification of pERK1/2 after 30 min incubation showed significantly higher phosphorylation in cells on PEA (green bars) than on PMA (orange bars) surfaces assuming that better signaling is generally related to better cell adhesion onto PEA surface. Focusing on PEA surfaces only, VEGF-coated sample (FNc) showed higher level of ERK1/2 phosphorylation when compared to PEA without bound VEGF (FN) showing that VEGF bound to the substrate can facilitate stimulation of ERK1/2 pathway via VEGF receptor. Interestingly, PEA samples with VEGF present in the medium (FNm) did not show any difference in ERK1/2 phosphorylation from PEA sample without any VEGF (FN). This result was further consistent with phosphorylation level in PEA samples where VEGF was present both in the coating and in the medium (FNcm), as this sample behaved the same as sample with VEGF coating only (FNc), with no additional phosphorylation coming from stimulation by VEGF from the medium. This indirectly supports the hypothesis about synergistic effect of FN bound ligands, as only the FN-adhered VEGF in close vicinity of integrin binding sites was able to stimulate cells, while VEGF dissolved in the medium did not have any effect at this time point. b. Scheme of VEGF signaling pathway towards ERK1/2 stimulation: phosphorylation of 1175Tyr in VEGF receptor (VEGFR-2) after VEGF binding can stimulate Raf kinase via two different pathways—phosphorylation of phospholipase Cγ (PLCγ) followed by activation of protein kinase Cα (PKCα), or stimulation of Src homology 2 domain (Shc) and subsequent activation of growth factor receptor-bound protein 2 (GRB2). Activated Raf leads to phosphorylation of mitogen-activated protein kinase kinase 1 and 2 (MEK1/2) that phosphorylates mitogen-activated kinase 1 and 2 (ERK1/2) that eventually leads to activation of c-Fos transcription factor which forms heterodimers with c-Jun and binding to DNA results in increased cell proliferation.

Figure 10:
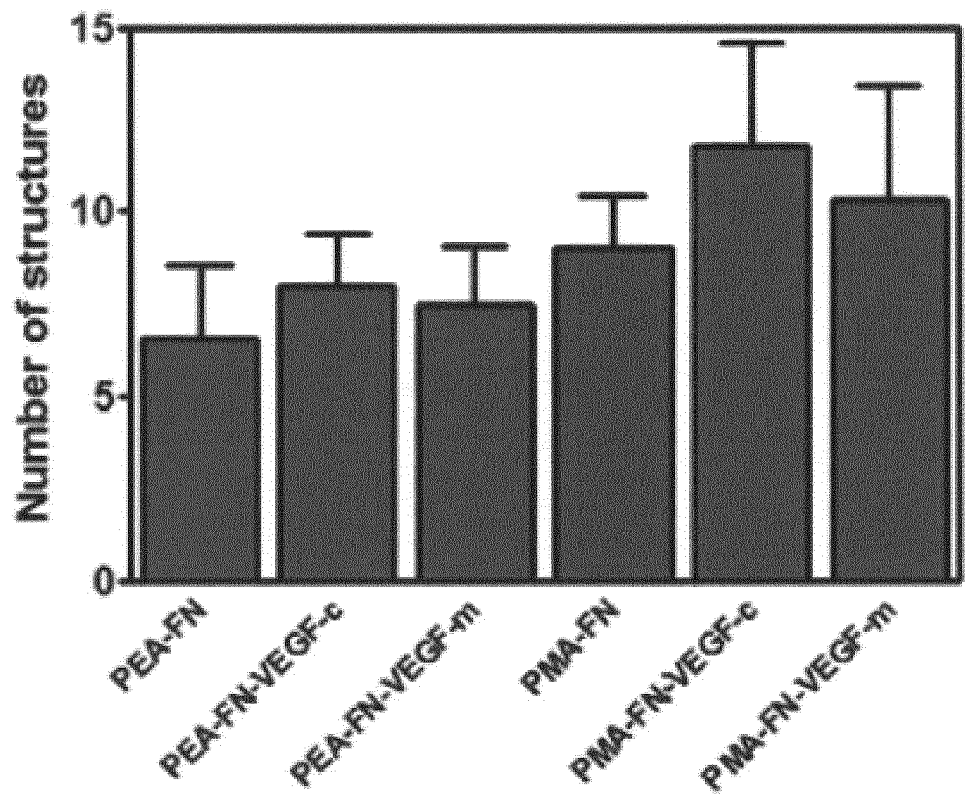

FIG. 10. Quantification of number of HUVEC aligned structures on functionalized substrates.

Figure 11:
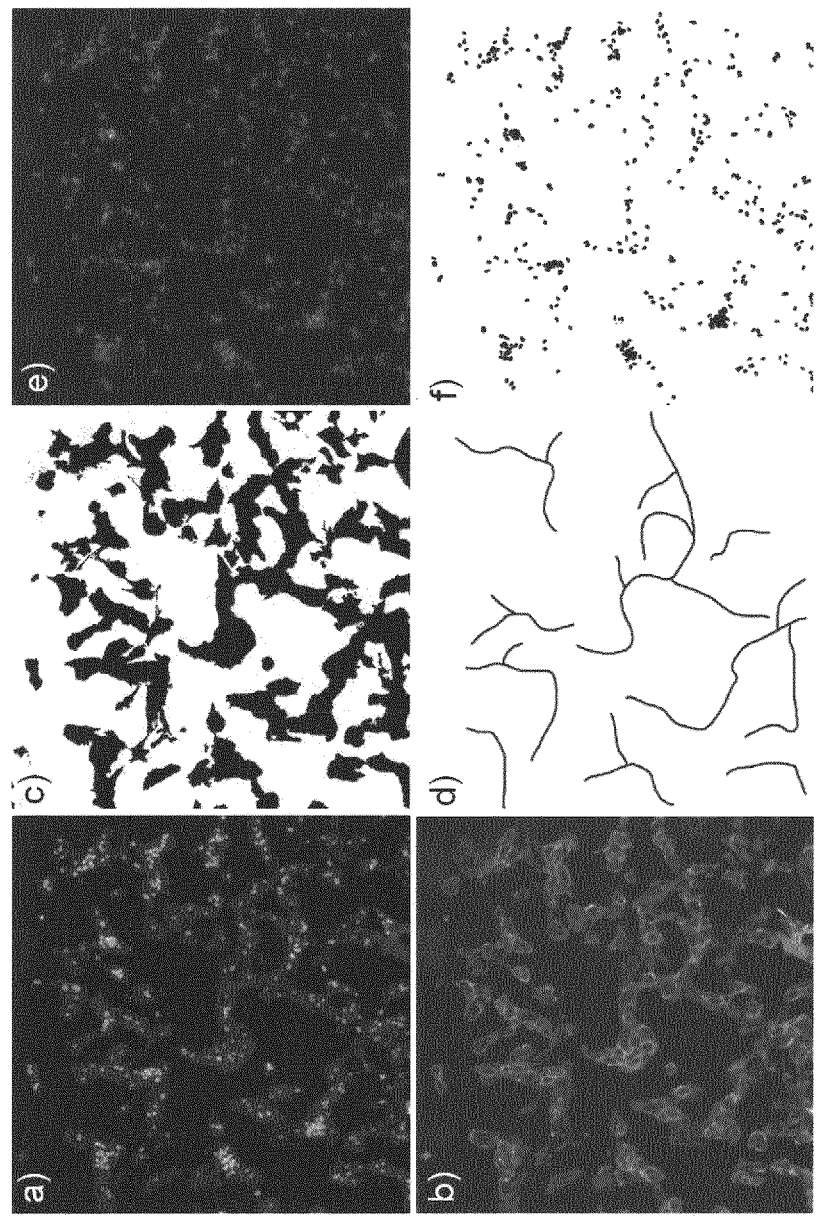

FIG. 11. An example of image processing used for image analysis of HUVEC growth and alignment on functionalized substrates (PEA-FN-VEGF-coated example). a. composite image of actin (red, outer staining) and DAPI (cyan, inner staining) staining. b. Raw image of actin staining from which a mask image (c.) was prepared and used for quantification of cell area coverage. Raw actin image was also used for making a simplified binary image cell alignment (d.) from which lengths and numbers of aligned structures and junctions were calculated. e. Raw image of DAPI staining from which a binary image (f.) was produced to count cells per area.

Figure 12:
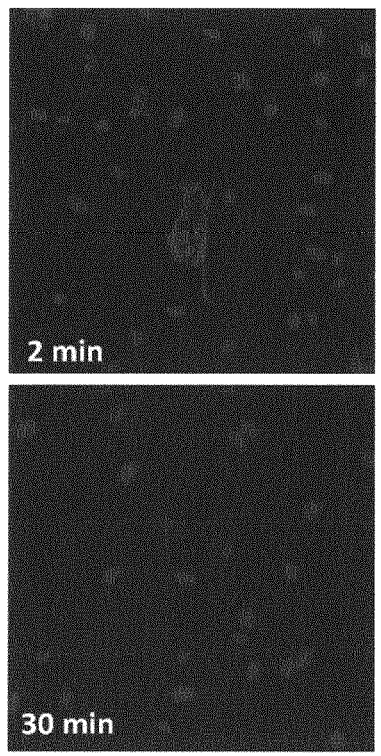

FIG. 12. Phosphorylation of VEGFR-2 in HUVEC after 2 and 30 min of stimulation with VEGF. After 2 min of stimulation the phosphorylated receptor was observed (red staining, only present in 2 min image), while after 30 min incubation no phosphorylation was detected anymore (blue staining for nuclei, same present in both 2 min and 30 min image).

Figure 13:
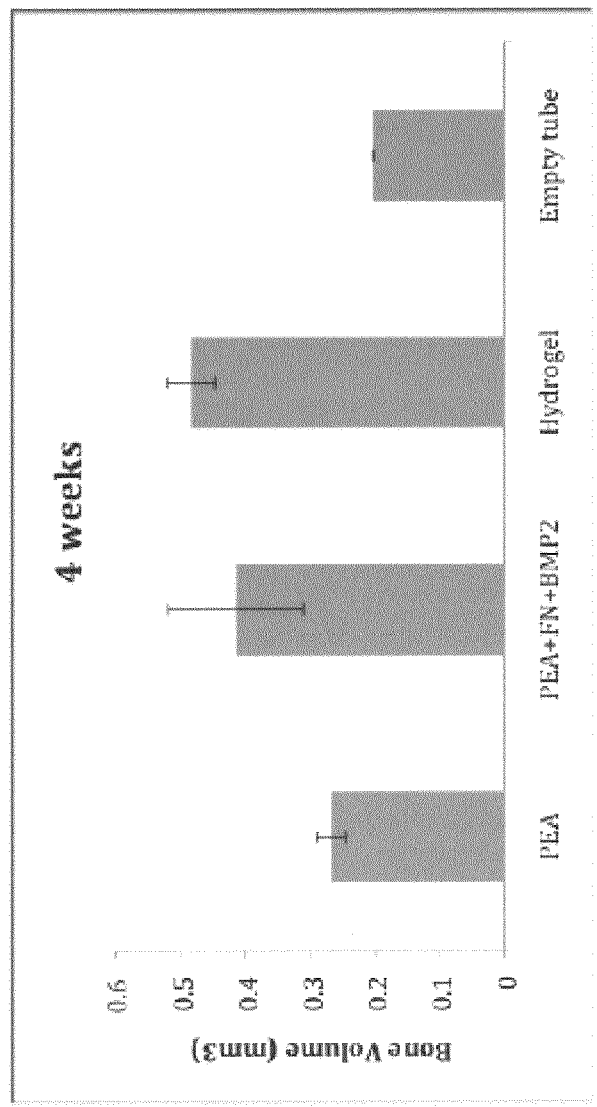

FIG. 13. Bone volume achieved using a construct for a critical size bone defect in a small animal model.

Figure 14:
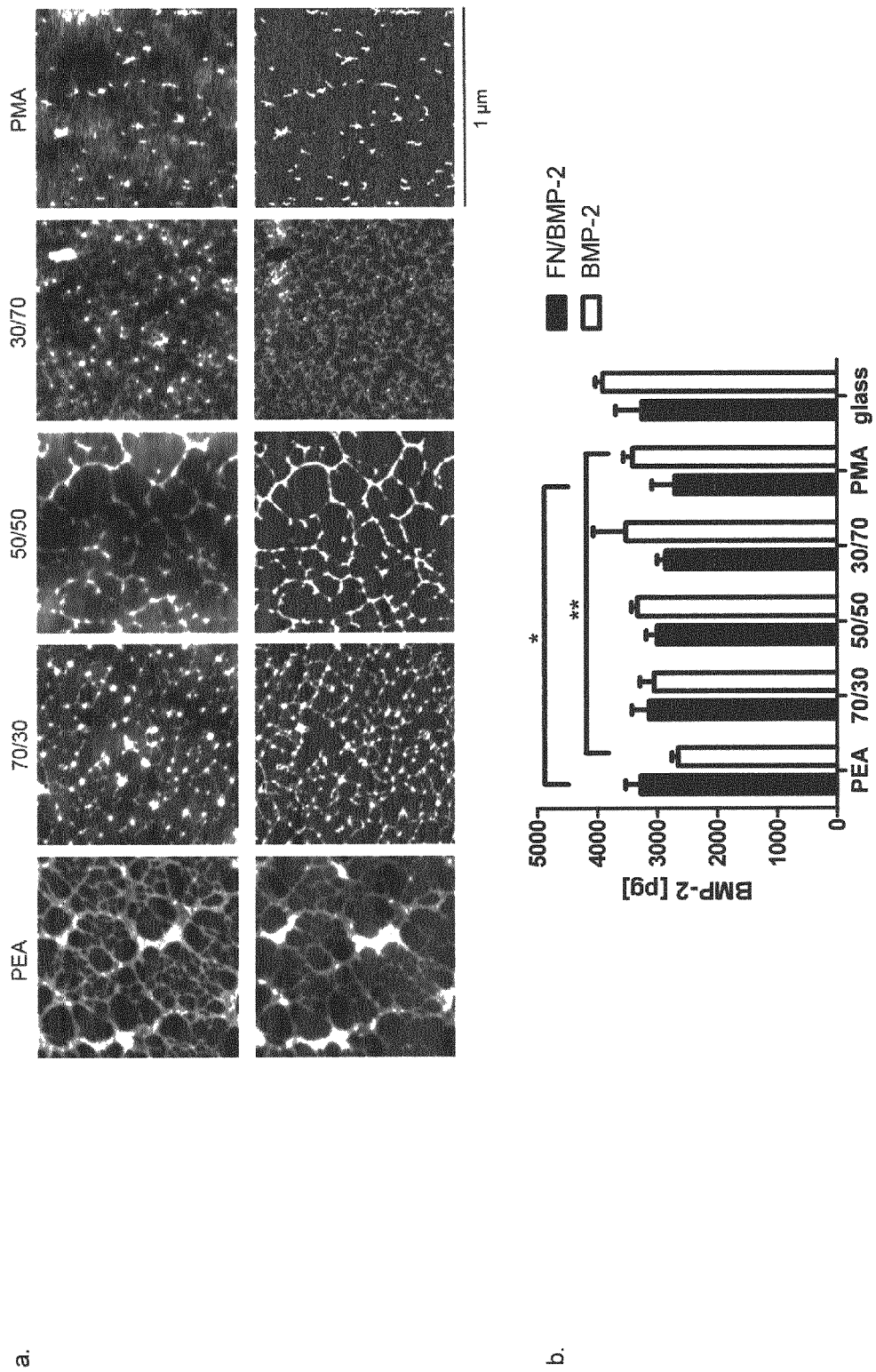
Figure 14:
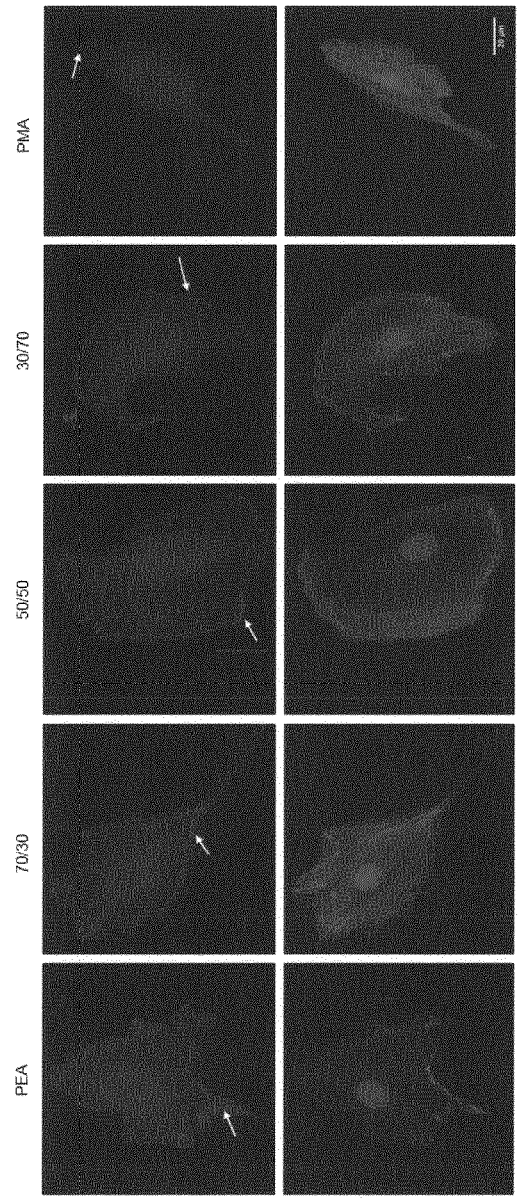

FIG. 14. Interaction between BMP-2 and FN on various polymer-driven FN networks. Polymer solutions were prepared from bulk co-polymers of poly(ethyl acrylate) (PEA) and poly(methyl acrylate) (PMA): PEA (100%), PEA/PMA (70/30), PEA/PMA (50/50), PEA/PMA (30/70) and PMA, and spin-coated on substrates. a. Height (upper) and phase (lower) AFM images of spin-coated substrate samples for each of the various polymer surfaces. b. Amount of BMP-2 on FN-coated and non-FN-coated substrates for each of the various polymer surfaces. c. Cell adhesion of hMSCs on FN/BMP-2-coated samples 1 d after seeding, with fluorescent staining of focal adhesion (red), actin cytoskeleton (green) and nuclei (blue).

Figure 15:
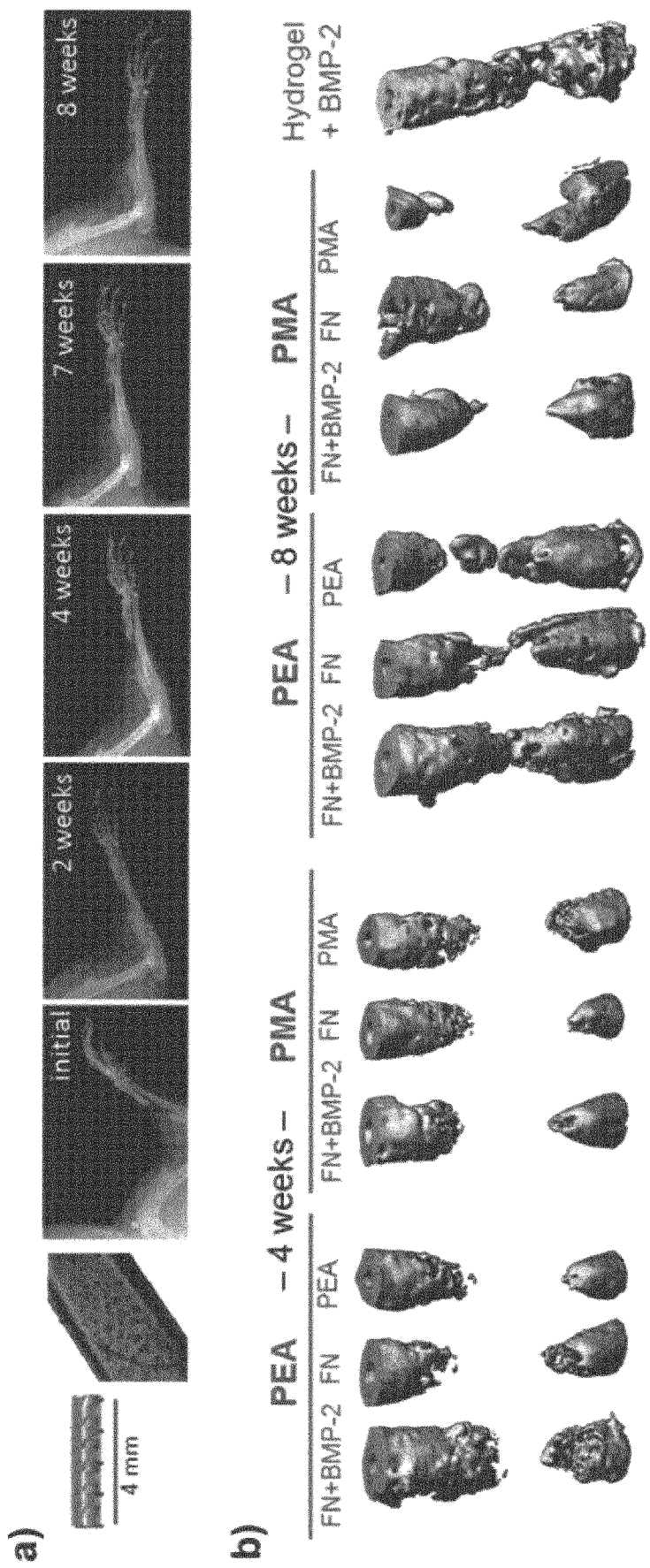
Figure 15:
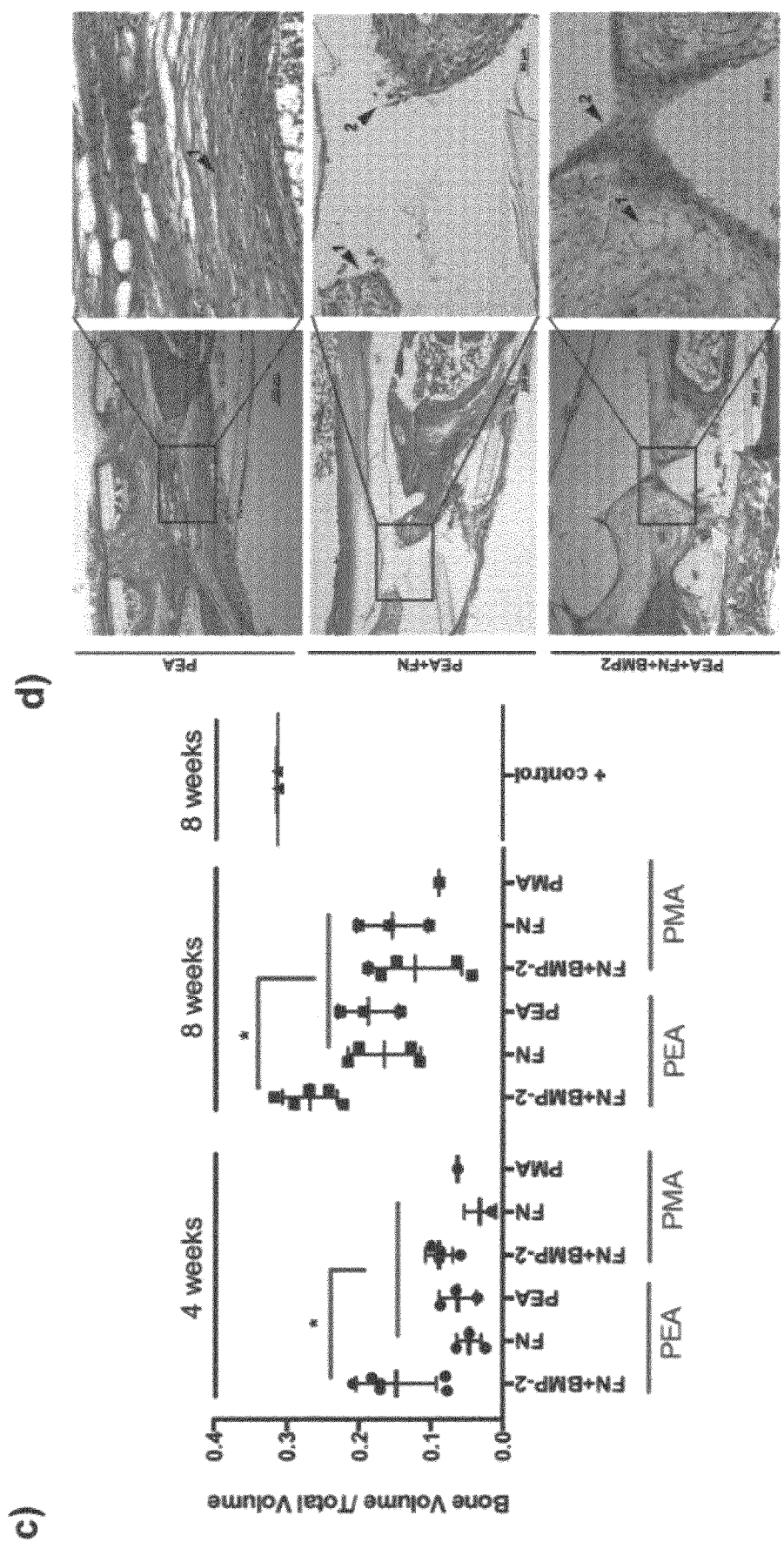

FIG. 15. Bone regeneration in a critical size defect with very low doses of BMP-2. a. A cylindric polyimide sleeve was coated with the polymers (either PEA or PMA, the figure shows a picture of the sleeve and the coating is shown with a florescence dye) and implanted in a critical size defect, 2.5 mm, in a murine radius. Faxitron images shows the evolution of the defect after implanting PEA coated with FN and BMP-2 after different time points. The total amount of BMP-2 was ~15 ng. b. 3D mCT reconstructions for both polymers PEA and PMA after 4 and 8 weeks, with three conditions: polymer only (PEA, PMA); FN coating on the polymer (FN), FN coating on the polymer followed by BMP-2 adsorption (FN+MBP-2). The positive control is a PEG hydrogel loaded with ~175 ng of BMP-2. c. mCT measures of bone volume within the defects. d. Sections of 8 week radial samples stained with Safranin-O/Fast Green. Arrow 1 shows the fibroblast-like morphology of cells. Arrows 2 and 3 show the new bone cells coming out of both distal and proximal sides. Arrow 4 shows bone-marrow like cavities found in the new bone. Arrow 5 shows the point at the contact point of new bone, coming out of both distal and proximal sides. Five animals (n=5) per condition were used. Symbols show statistical significant differences with all the other conditions (* p 0.001).

Figure 16:
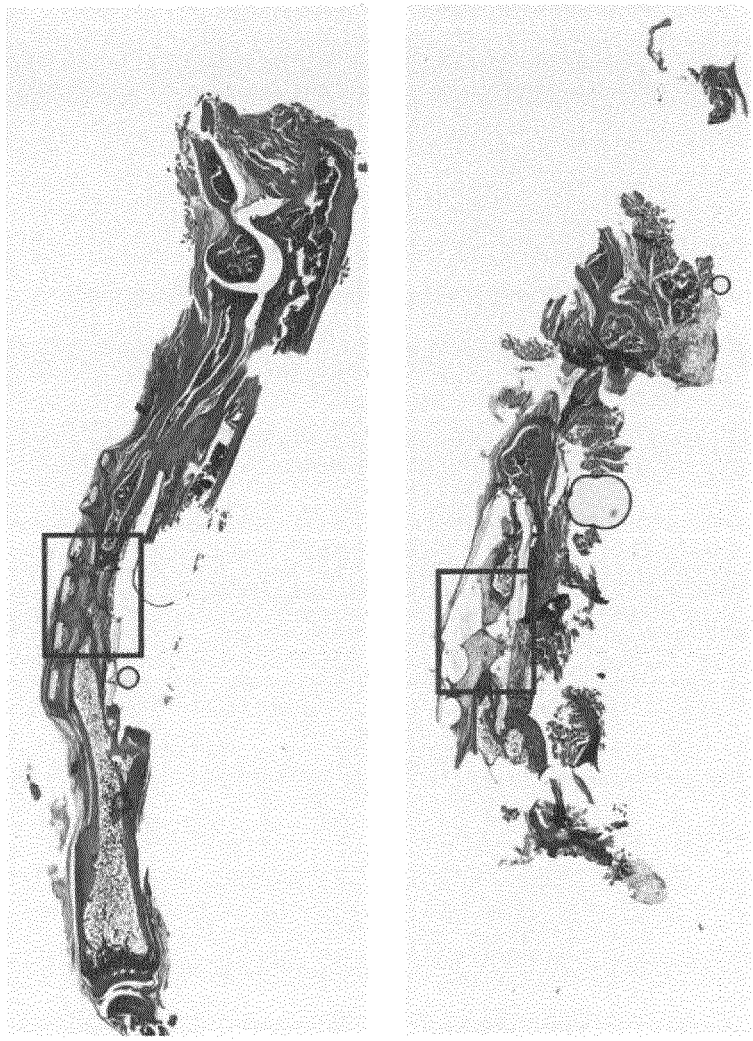

FIG. 16. Full longitudinal sections of 8 weeks radial samples stained with Safranin-O/Fast Green. The area inside the rectangle is shown in FIG. 15.

Figure 17:
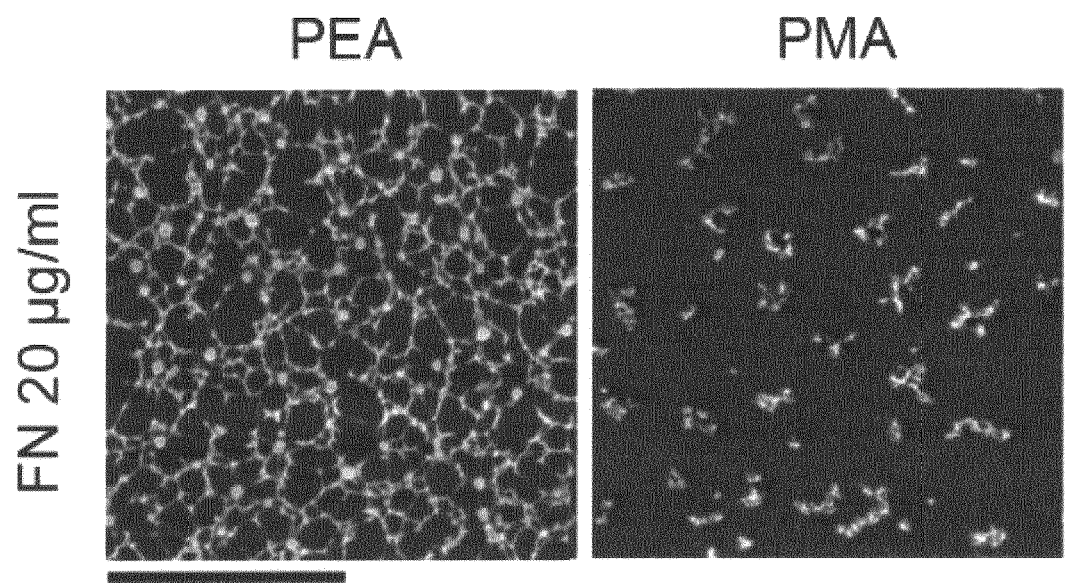

FIG. 17. FN conformation on material substrates. PEA and PMA coated from a solution of 20 μg/ml FN. Images obtained by AFM. Scale bar is 0.5 μm.

Figure 18:
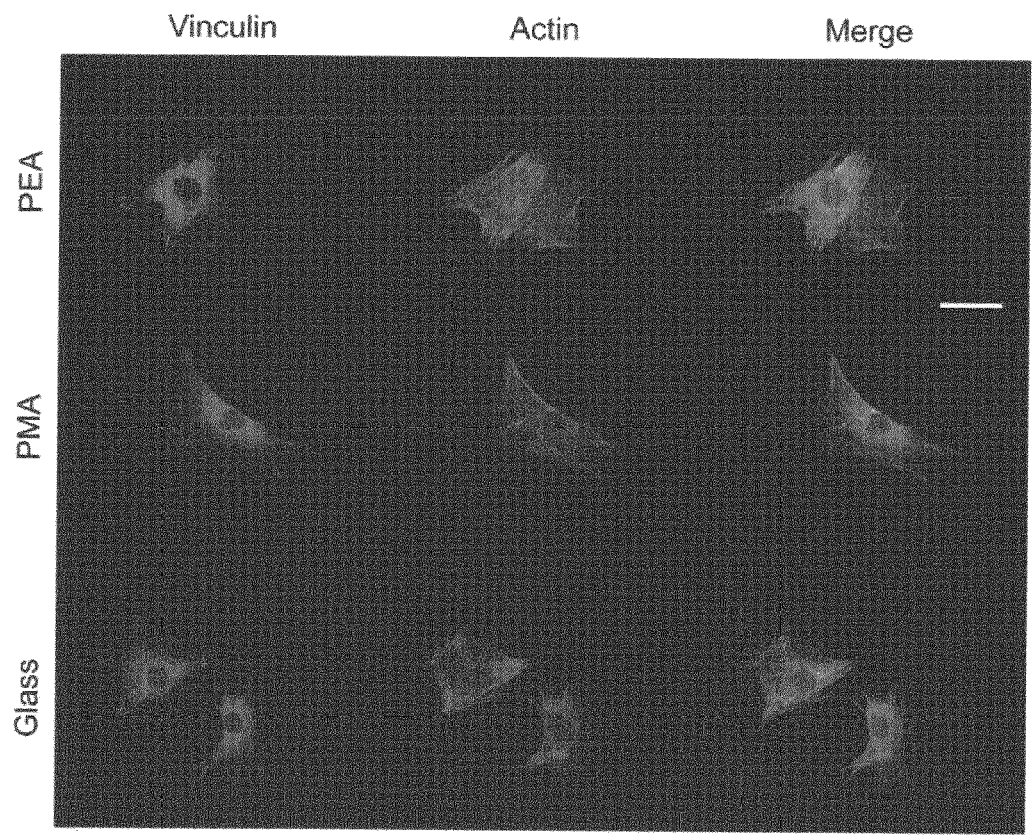
Figure 18:
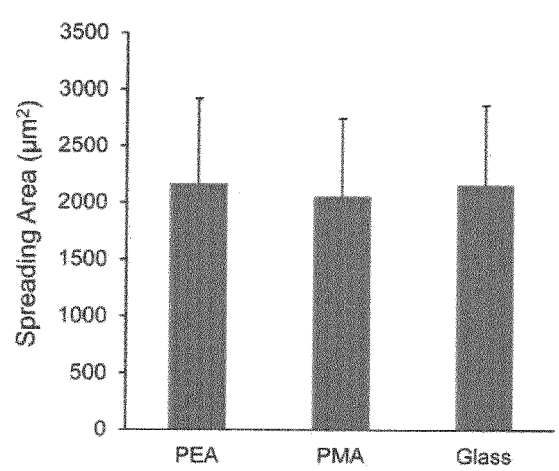
Figure 18:
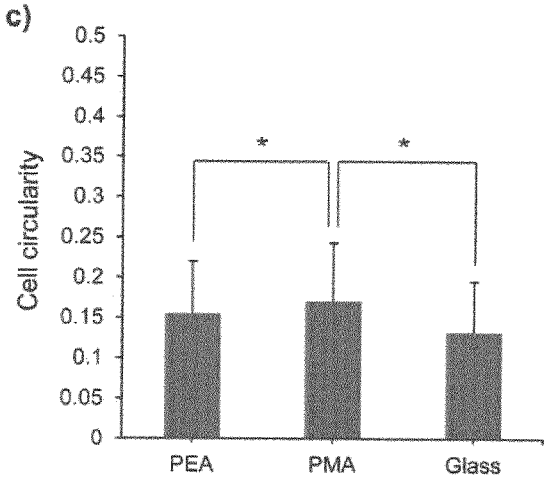

FIG. 18. Adhesion of mMSC on FN coated substrates. a) Spread morphology of cells. Green staining shows actin stress fibres and magenta denote focal adhesion protein vinculin. Scale bar 50 μm. b) Quantification of spreading area of cells (n>200 cells) resulted in similar values for all substrates. c) Quantification of cell circularity values (n>200 cells), PMA presented higher values of circularity compared with PEA and Glass. b) and c) shoed mean±standard deviation. $*p<0.05$.

Figure 19:
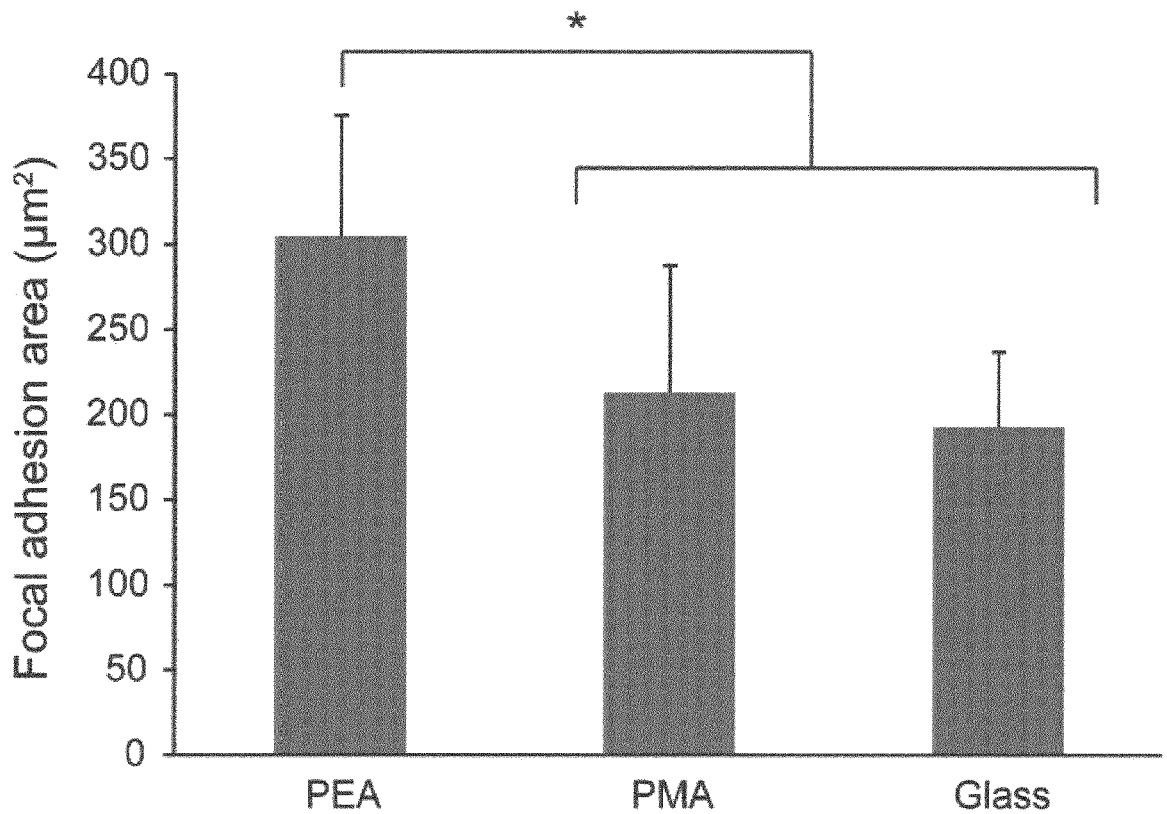
Figure 19:
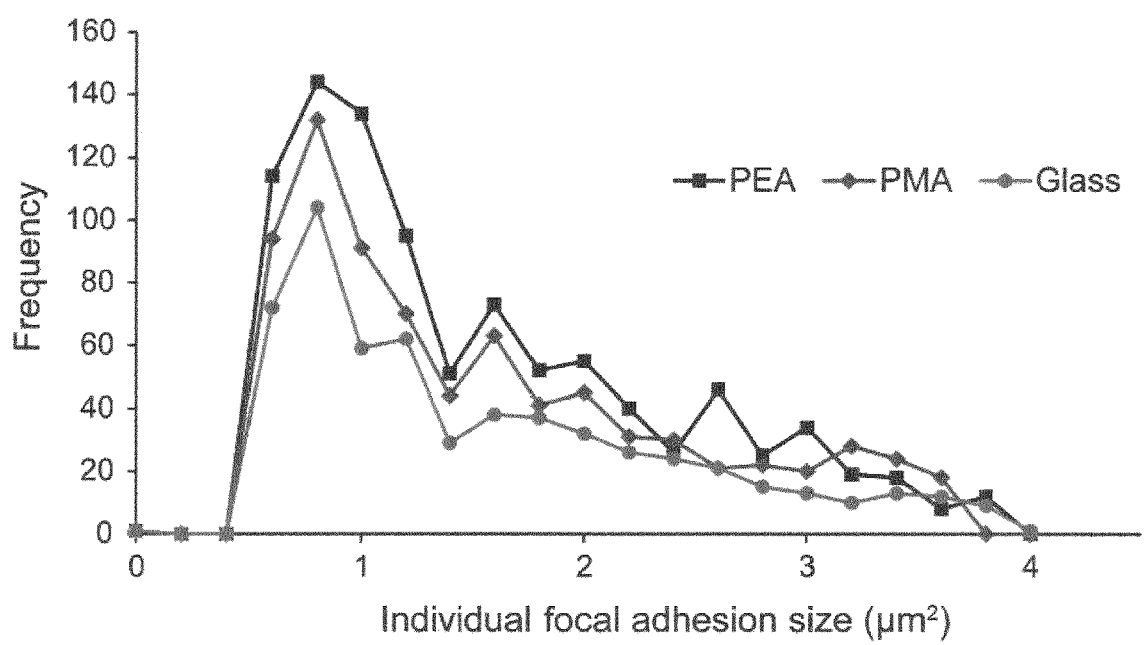
Figure 19:
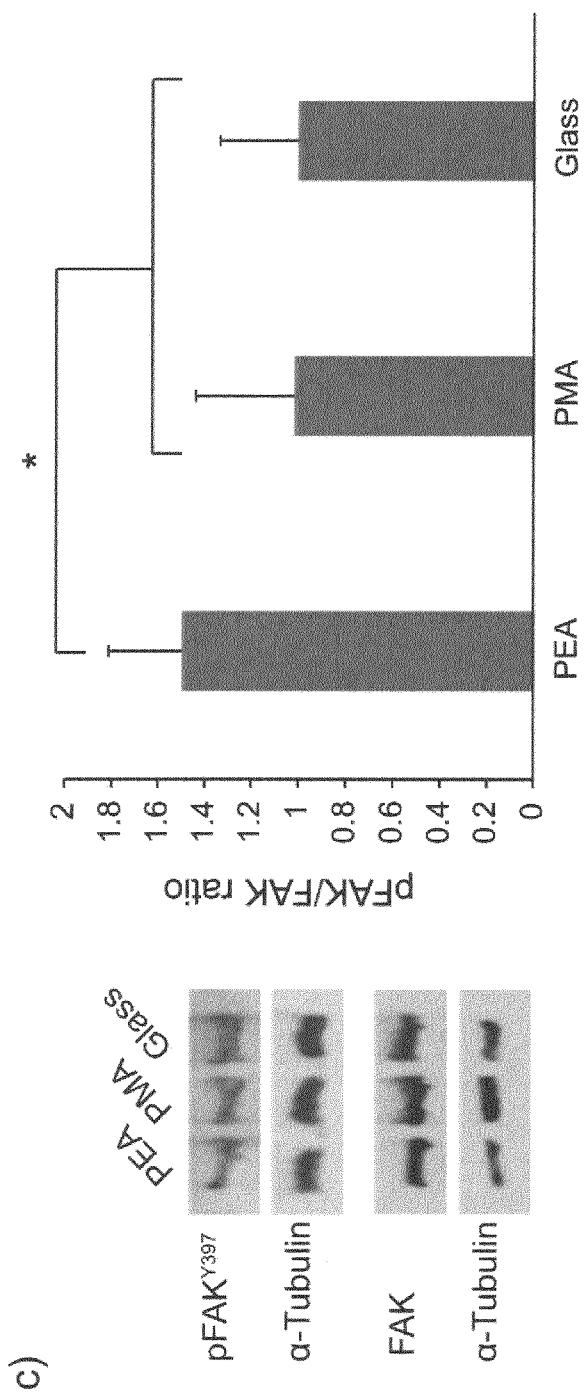

FIG. 19. Focal adhesion and cell signalling. a) Quantification of focal adhesion area on cells cultured on different substrates. PEA showed the highest values followed by PMA and Glass. b) Frequency distribution for focal adhesion size. PEA showed the higher number of individual focal adhesions, the trend was similar for all substrates. c) Western blot for pFAK and FAK from cells grown onto different substrates. Normalised pFAK/FAK ratio showed high levels for PEA compared to PMA and Glass substrates. a) (n=10 cells) and c) 3 independent experiments represented as mean±standard deviation. $*p<0.05$.

Figure 20:
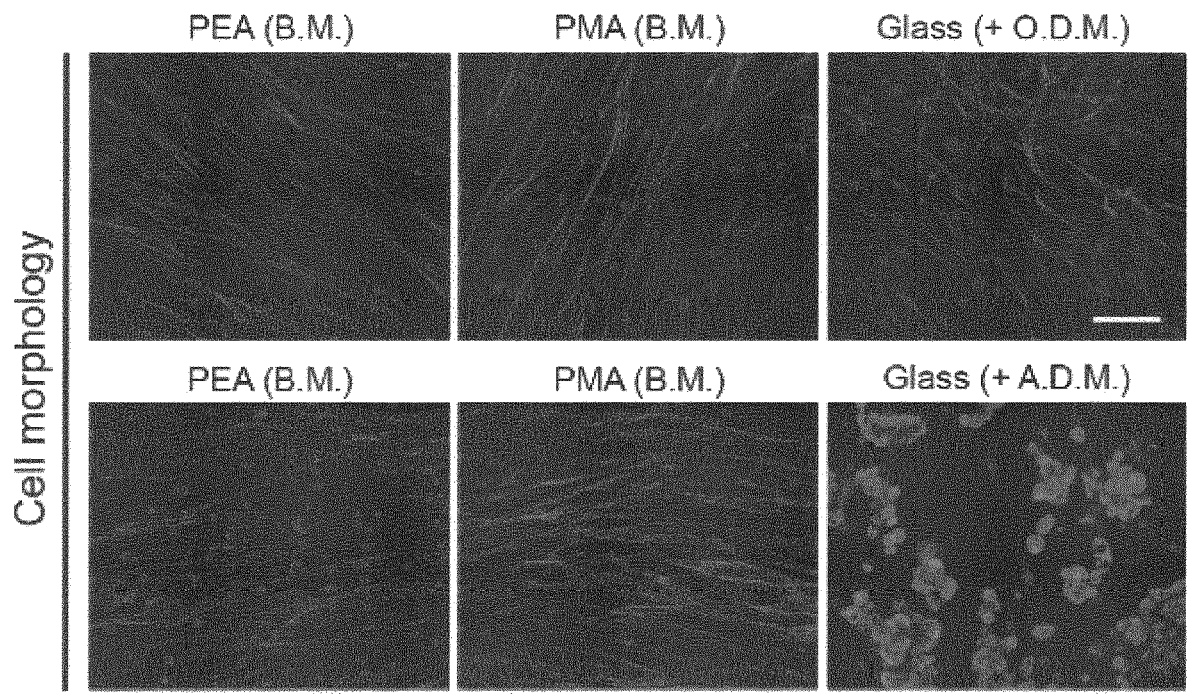

FIG. 20. mMSC phenotypes. Fluorescence staining showing actin cytoskeleton (green) and nuclei (blue) for evaluation of morphological features of mMSC. Cells cultured onto FN-coated PEA and PMA substrates under basal media conditions (B.M.) during 15 days. No spontaneous differentiation was observed. Control Glass was cultured under osteogenic (osteogenic differentiation medium, +O.D.M.) and adipogenic stimulating conditions (adipogenic differentiation medium, +A.D.M.). Cell morphology showed characteristic morphologies of osteoblast and adipocytes respectively. Scale bar 50 μm.

Figure 21:
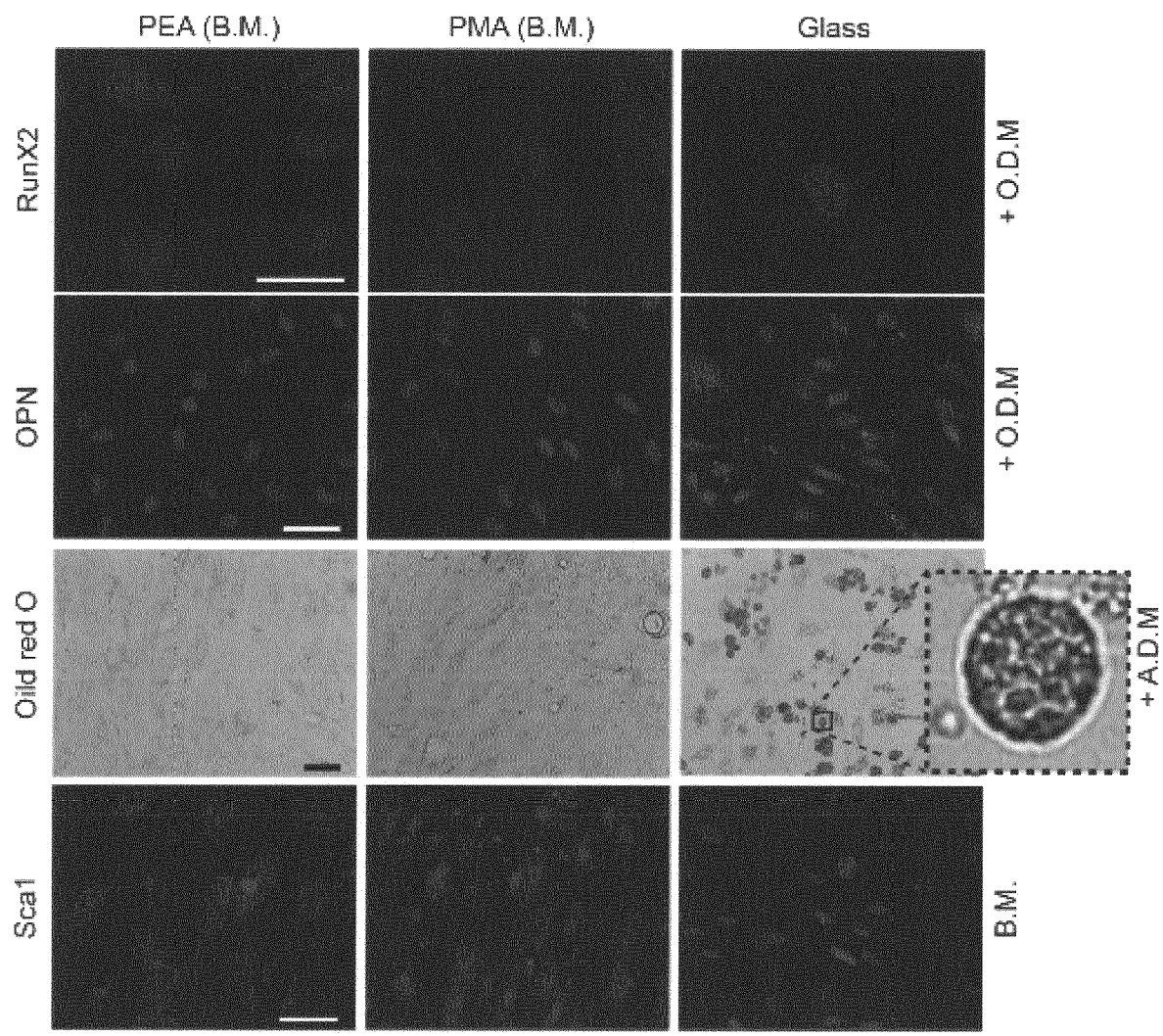

FIG. 21. mMSC differentiation under basal conditions. Immunofluorescence for osteogenic markers Runx2 (red), OPN (green); Sca 1 was used as stemness marker (red); Nuclei are showed in blue; adipogenic commitment was evaluated by Oil red O staining. Control substrates were cultured under differentiation medium (+O.D.M.) and adipogenic differentiation medium (+A.D.M.). PEA and PMA showed minimum levels of OPN and Oil red O staining under basal conditions (B.M.). Runx2 expression was higher on PEA. Stemness marker (Sca1) expression was elevated only in FN-coated PEA and PMA substrates under basal conditions (B.M.). Scale bar 50 μm.

Figure 22:
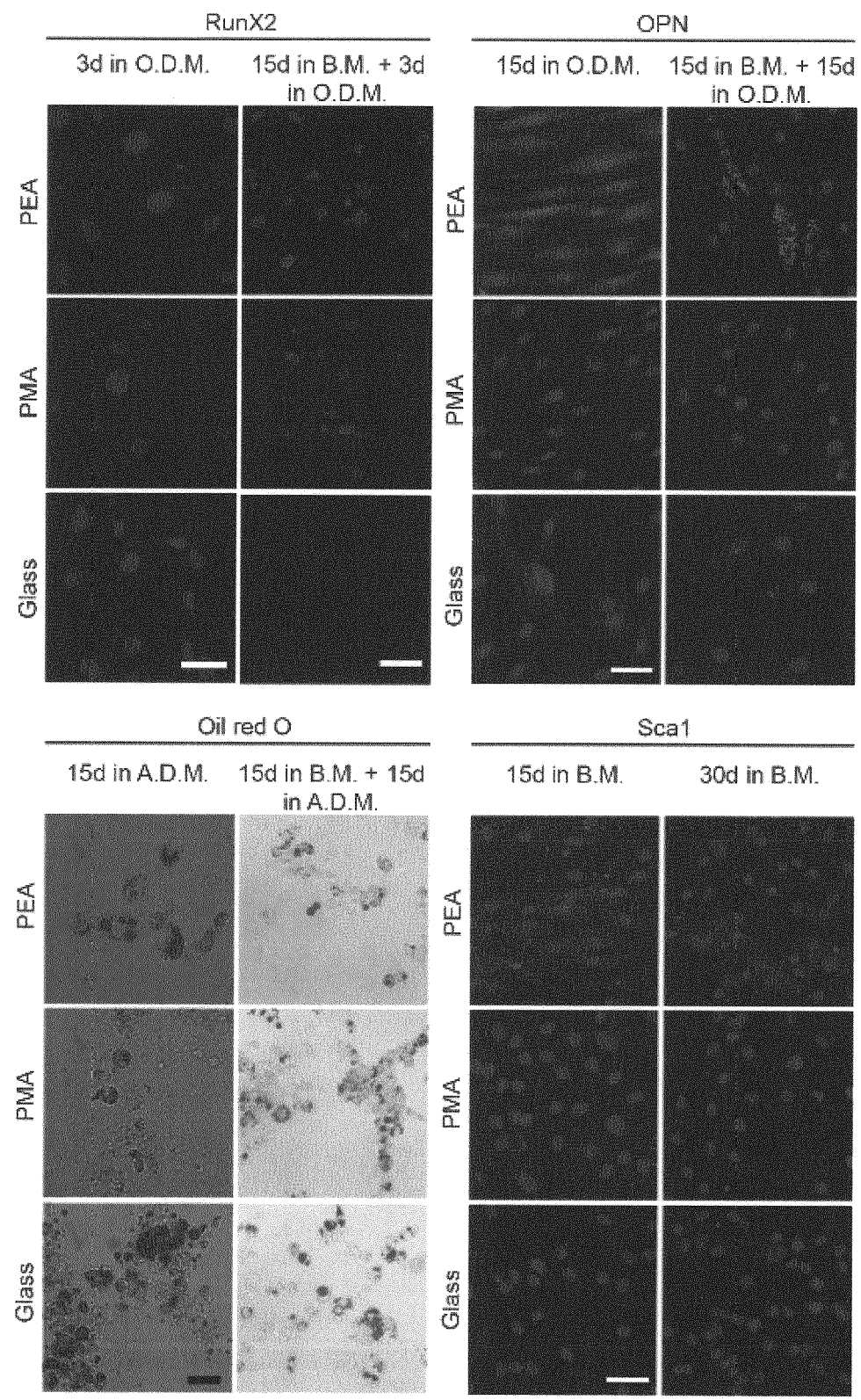

FIG. 22. mMSC under differentiation conditions. Immunofluorescence for osteogenic differentiation: Runx2 (red), OPN (green); Sca1 was used as stemness marker (red); nuclei are shown in blue; adipogenic commitment by Oil red O staining. FN-coated PEA and PMA showed similar potential to induce osteogenic/adipogenic phenotypes under differentiation conditions (osteogenic, O.D.M and adipogenic, A.D.M.) during 15 days of culture compared to Glass differentiated control. When cell cultures where performed with a previous treatment of 15 days in basal media (B.M.) and subsequently induced to differentiate, FN-coated PEA showed the high levels in osteogenic markers, as well as stemness maintenance after 30 days of culture.

Figure 23:
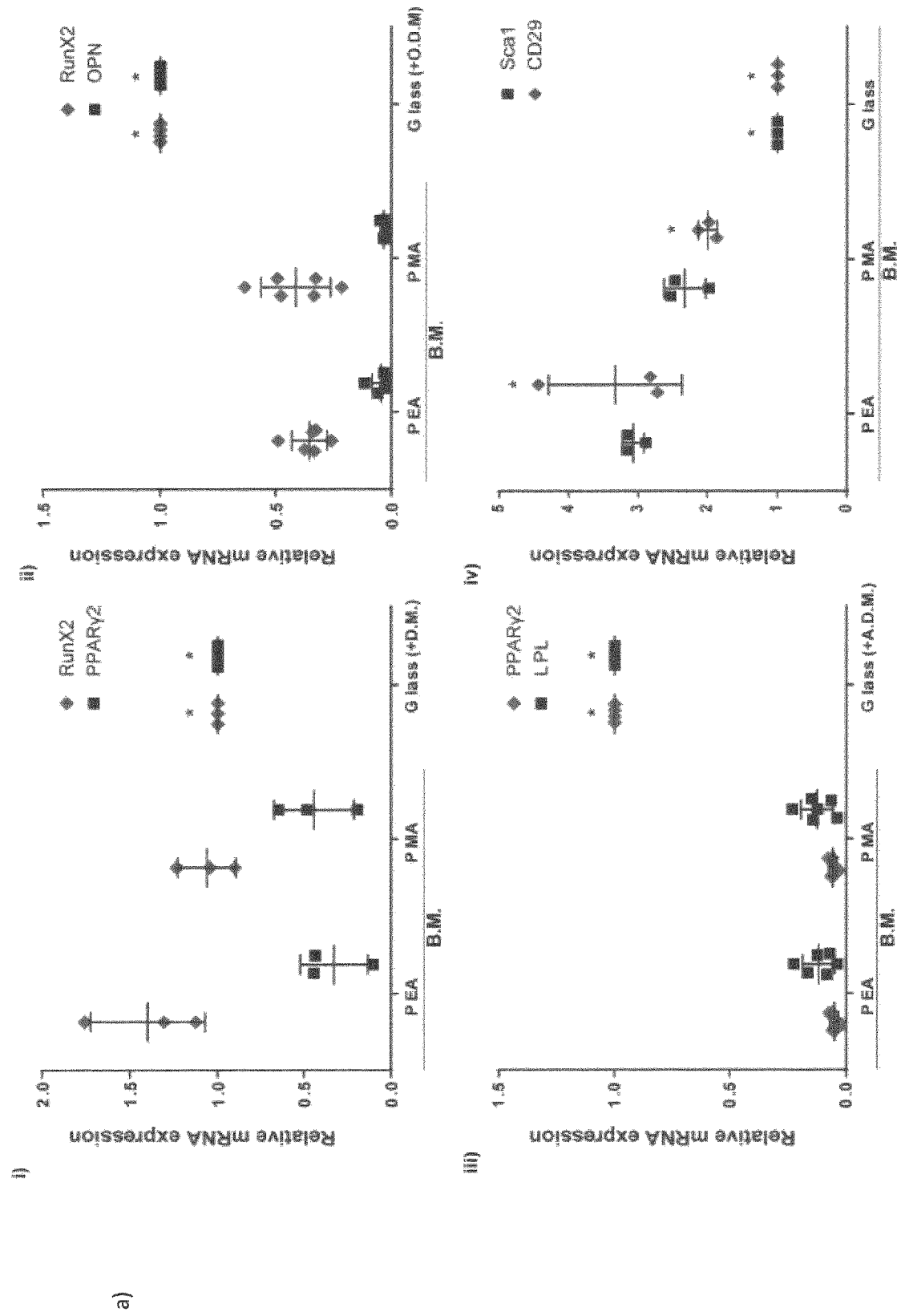
Figure 23:
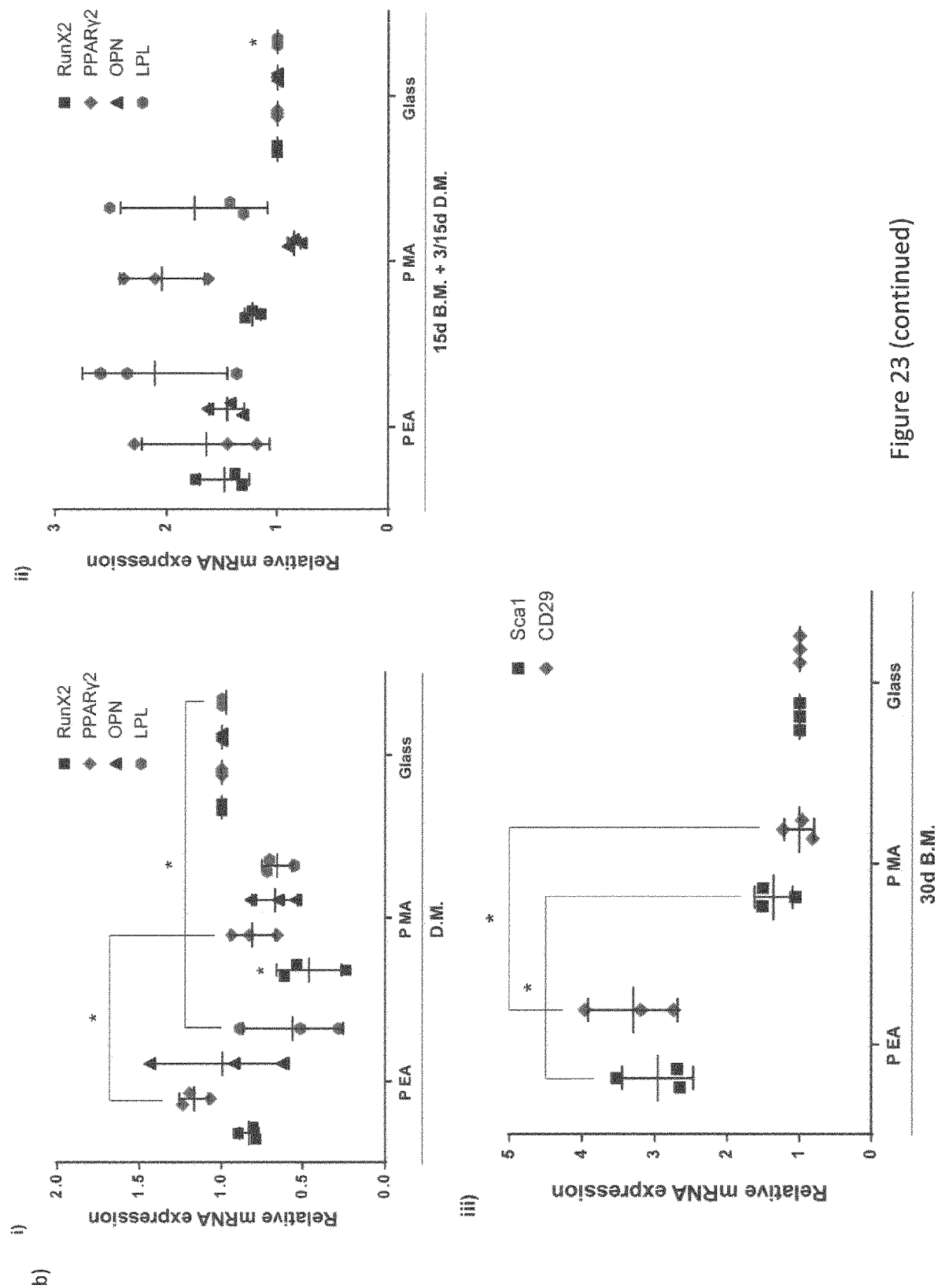

FIG. 23. Analysis of relative mRNA expression under basal and differentiation conditions.

7-a) mRNA expression under basal conditions.

i) Cells cultured under basal conditions (B.M.). Representation of relative levels of mRNAs of early transcription factors that determine lineage commitment after 3 days of culture: Runx2 for osteogenic commitment and PPARγ2 for adipogenic commitment. ii) and iii) Cells cultured under basal conditions (B.M.). Control glass was induced to differentiate under osteogenic (O.D.M.) and adipogenic medium (A.D.M.). Representation of relative levels of mRNAs of genes markers of osteogenesis (Runx2 and OPN) and adipogenesis (PPARγ2 and LPL). iv) Cells cultured under basal conditions (B.M.).

Representation of relative levels of mRNAs of genes markers of stemness maintenance (Sca1 and CD29) after 15 days of culture.

7-b. mRNA expression under differentiation conditions.

i) Cells cultured under differentiation conditions (osteogenic, O.D.M and adipogenic medium A.D.M). Representation of relative levels of mRNAs of genes markers of osteogenesis (Runx2 and OPN) and adipogenesis (PPARγ2 and LPL) after 3 days (Runx2 and PPARγ2) and 15 days of culture (OPN and LPL).

ii) Cells previously cultured under basal conditions for 15 days, and subsequently stimulate to differentiate with osteogenic (O.D.M.) or adipogenic (A.D.M.) medium. Representation of relative levels of mRNAs of genes markers of osteogenesis (Runx2 and OPN) and adipogenesis (PPARγ2 and LPL) after 3 days (Runx2 and PPARγ2) and 15 days of culture (OPN and LPL).

iii) Cells cultured under basal conditions for 30 days. Representation of relative levels of mRNAs of genes markers of markers of stemness maintenance (Sca1 and CD29). FN-coated PEA showed high expression of stemness markers.

Figure 24:
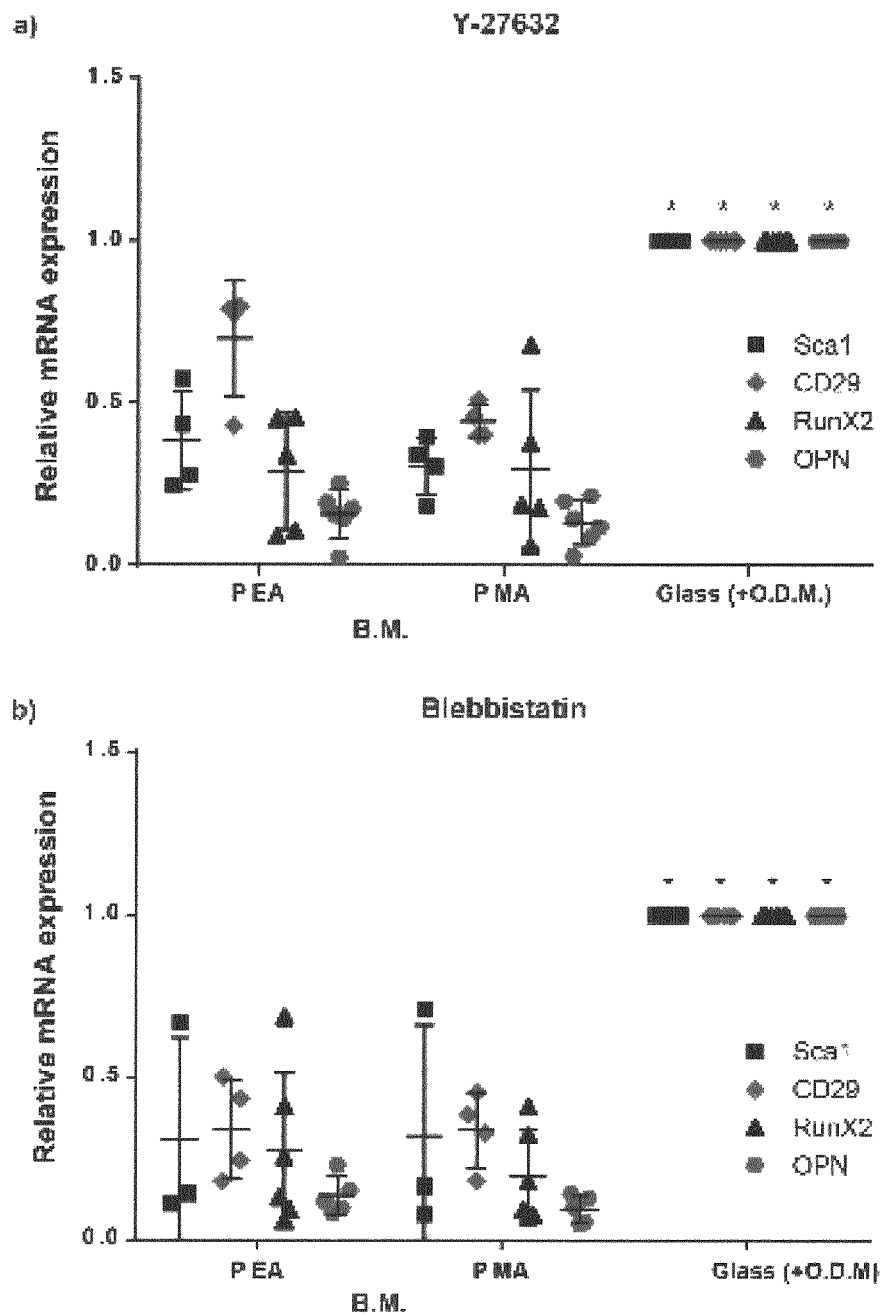

FIG. 24. Analysis of relative mRNA expression after inhibition of contractility. a) and b) Cells cultured under basal conditions (B.M.). Cells on control glass were induced to differentiate to osteogenic commitment (+O.D.M.). Representation of relative levels of mRNAs of genes markers of osteogenesis (Runx2 and OPN) and stemness maintenance (Sca1, CD29) after 15 days of culture with addition of inhibitors of contractility Y-27632 and Blebbistatin respectively. Inhibition of contractility strongly reduced expression of stemness markers.

DETAILED DESCRIPTION OF THE INVENTION

Cell Culture Surfaces with BMP-2 to Control Stem Cell Differentiations

Here we report, for the first time, a simple, robust and translational material-based approach to present BMP-2 in combination with the integrin binding domain of fibronectin (FN). This strategy is based on the self-organization of FN into (nano)networks at the material interface upon adsorption on poly(ethyl acrylate) (PEA) and exploiting this nanofibrillar matrix to capture and present BMP-2. This approach unlocks the potential for artificial synergistic signalling using chemistries that can be applied to large areas of complex (2D and 3D) biomaterial scaffolds. We examined the effects of these surfaces on human mesenchymal stem cells (MSCs) as a clinically-relevant stem cell type and demonstrate that our simple approach can influence cell adhesion through colocalisation of FN and BMP-2 which synergistically drives integrin-GF receptor signalling and ultimately directs stem cell differentiation.

Materials and Methods

Preparation of Materials and Synergistic Surfaces

Polymer sheets were obtained by radical polymerization of a solution of the corresponding alkyl acrylate, i.e., methyl (MA) and ethyl (EA) (Sigma-Aldrich) using 1 wt % and 0.35 wt % benzoin respectively (98% pure, Scharlau) as a photoinitiator. The polymerisation was carried out up to limiting conversion. After polymerisation, low molecular-mass substances were extracted from the material by drying in vacuo to constant weight. Thin films were prepared by making use of a spin-coater (Brewer Science, Rolla USA). To do that, PMA and PEA were dissolved in toluene at a concentration of 6% and 2.5%. Spin casting was performed on glass coverslips at 2000 rpm for 30 s. Samples were dried in vacuo at 60° C. before their use. Fibronectin (FN) from human plasma (Sigma; Invitrogen) was adsorbed from solutions of 20 μg/ml concentration during 1 h at RT and blocked in BSA (Sigma) 1% BSA/Dulbecco's phosphate-buffered saline (DPBS) for 30 minutes at RT. For growth factor adsorption, 25 ng/ml BMP-2 (R&D Systems, 355-BM or 355-BM/CF for AFM studies) in DPBS was used during 1 h at RT. For AFM studies, FN was adsorbed from solutions of 3 μg/ml concentration in DPBS; to observe the sole growth factor on the surface, the concentration used was 100 ng/ml. For synergy blocking assays, $FNIII_{12-14}$ domains were blocked before BMP-2 coating using the monoclonal P5F3 antibody against this specific region (SantaCruz Biotechnology, sc-18827, 1:30). Finally, samples were rinsed in DPBS to eliminate the non-adsorbed protein.

Atomic Force Microscopy

AFM experiments were performed using a Multimode AFM equipped with NanoScope IIIa controller from Bruker operating in tapping mode; the Nanoscope 5.30r2 software version was used. Si cantilevers from Bruker were used with force constant of 2.8 N/m and resonance frequency of 75 kHz. The phase signal was set to zero at a frequency 5-10% lower than the resonance one. Drive amplitude was 600 mV and the amplitude setpoint Asp was 1.8 V. The ratio between the amplitude setpoint and the free amplitude Asp/A0 was kept equal to 0.8.

Immunogold Staining

Immunogold staining for AFM was done using fixed samples (4% formaldehyde, 30 minutes, RT) with the different protein coating conditions. Samples were incubated with anti-BMP2/4 antibody (SantaCruz Biotechnology, sc-9003, 1 h, RT). After washing 3 times with DPBS/0.5% Tween-20 in agitation, samples were incubated with 15 nm gold particle conjugated anti-Rabbit IgG (Aurion, 815.011, 1 h, RT). Finally, samples were washed and fixed (2% gluteraldehyde, 5 min, RT).

Availability of the $FNIII_{12-14}$ Domain

After coating with FN, a monoclonal antibody for the $FNIII_{12-14}$ domain (also known as Heparin domain) was used (SantaCruz Biotechnology, sc-18827, 1:30, 2 h, 37° C.). Samples were washed three times with DPBS/0.5% Tween 20. An anti-mouse IgG HRP-conjugated antibody (Invitrogen, 626520, 1:2000, 1 h, RT) was then used. After washing twice, samples were exposed to the substrate solution (R&D, DY999) and incubated for 20 minutes at RT in dark. A stop solution (R&D, DY994) was added before reading the absorbance at 450 nm.

Quantification of BMP-2 Adsorption

Both on bare or FN coated surfaces, the amount of non-adsorbed growth factor remaining in the supernatant was measured via a sandwich ELISA (DY355, R&D) following manufacturer instructions. The standard curve was calculated using a 4-PL curve-fit (Prism). For stability studies, the release of the BMP-2 was measured at 10 different time points (2 h, 1, 2, 3, 4, 5, 6, 7, 11, 14 days) using the same sandwich ELISA.

Cell Culture

Human bone marrow mesenchymal stem cells (hMSCs) from Promocell were maintained in basal media (αMEM, 10% FBS, 1% P/S, 1% fungizone, 2 mM L-glutamine, 1 ng/ml FGF-2) at 37° C. with 5% $CO_2$. Cells were seeded onto the materials at 104 cells/cm2 using seeding media (DMEM high glucose, 1% P/S, 1% FBS,) and media were changed twice a week. For all cultures the first 2 hours (initial cell adhesion) were in absence of serum and GF. Cells were used at passages P0-P3. Each experiment was performed in triplicate.

Co-Immunoprecipitation

After 45 minutes of cell culture, cell lysates (RIPA buffer) were used to perform immunoprecipitation of integrin β1 and BMP-2 receptor BMPRIA. 15 μg of protein were collected using NanoDrop (ThermoScientific). First, an integrin β1 antibody (Abcam, 183666, 10 ul/reaction) was used together with protein A-agarose beads (SantaCruz Biotechnology, sc-2001). Then, after denaturation and elution of beads, samples were run in NuPAGE 4-12% bis-tris gels (Life Technologies). A mouse BMPRIA antibody was used to probe the membrane (Abcam, 166707, 1:1000). An anti-mouse secondary antibody was used (SantaCruz Biotechnology, sc-2031, 1:5000). The enhanced chemiluminescence detection system (GE Healthcare) was used prior to exposing the blot to X-ray.

Phosphorylated ERK 1/2

Phosphorylated ERK 1/2 was quantified using phospho-ELISA kits. Briefly, ELISA plates were coated with a capture antibody for ERK 1/2 and then incubated with cell lysates after 45 minutes of cell culture. Phosphorylated states were detected with an anti-phospho-tyrosine antibody and normalised to a standard according to manufacturer instructions (DYC1018B, R&D Systems).

SMADDs Phosphorylation

Cell lysates (RIPA buffer) after 45 minutes of culture were used. 10 μg of proteins were collected per sample. Western blot assays were run in denaturalising conditions for SMAD-1, SMAD-1/5 and GAPDH. NuPAGE 4-12% bis-tris gels were purchased from LifeTechnologies. pSMADDs antibodies (pSMAD-1 & pSMAD-1/5) were obtained from Cell Signaling Technology (12656, 1:1000). As secondary antibody an antirabbit IgG antibody (Cell Signaling Technology, #7074, 1:2000) was used. A substrate for sensitive immunodetection system (Novex, Life Technologies) was used prior to exposing the blot to X-ray. Protein expression was quantified by image analysis using ImageJ.

SMADs Protein Expression:

RNA extraction was performed after 5 days of cell culture. Cells were lysed and total RNA extracted using a Qiagen RNeasy micro kit (DNase treatment included) and the quantity and integrity of the RNA was measured with NanoDrop (ThermoScientific). Real-time qPCR was carried out and analysed to assess the expression of SMAD-1, SMAD-5 and GAPDH. Briefly, RNA samples were reverse transcribed using the QuantiTect Reverse Transcription (Applied Biosystems). Real-time qPCR was carried out using SYBR® Select Master Mix (Life Technologies) and the 7500 Real Time PCR system from Applied Biosystems. GAPDH served as the house-keeping gene, and expression for the genes of interest was normalized to GAPDH expression. As the SYBR Green method was used, primer sequences for the genes were validated by dissociation curve/melt curve analysis. The comparative cycle-threshold method was used for quantification of gene expression. The relative transcript levels were expressed as mean±standard deviation (n=3 for each group).

Immunofluorescence Staining for Stem Cell Differentiation

After 14 days of culture cells were washed in DPBS and fixed with 4% formaldehyde in DPBS at 37° C. for 15 minutes. Afterwards, the samples were rinsed in DPBS and a permeabilising buffer (10.3 g sucrose, 0.292 g NaCl, 0.06 g MgCl2, 0.476 g Hepes buffer, 0.5 mL Triton X, in 100 mL PBS, pH 7.2) was added at 4° C. for 5 minutes. The samples were then saturated with 1% BSA/DPBS at 37° C. for 5 minutes. Subsequently, they were incubated at 37° C. for 1 h with primary antibody against osteocalcin (1:50, sc-73464, SantaCruz Biotechnology) or osteonectin (1:50, sc13 10758, SantaCruz Biotechnology) in 1% BSA/DPBS. After washing in PBS/0.5% Tween 20, an anti-rabbit secondary antibody (Vector Laboratories, 1:50) was incubated for 1 h at 37° C. Finally the samples were rinsed in DPBS before mounting in Vectashield containing DAPI staining (Vector Laboratories). A Zeiss fluorescence microscope was used for imaging.

Quantitative Real Time PCR

Cells were cultured on materials for 14 days. Following the same procedure as for SMAD protein expression, osteogenesis differentiation was analysed to assess the expression of osteocalcin (OCN) and osteonectin (ON) using GAPDH to normalize gene expression.

Primers for qPCR

|  | Forward | Reverse |
| --- | --- | --- |
| Osteocalcin | CAGCGAGGTAGTGAAGAGACC SEQ ID NO: 1 | TCTGGAGTTTATTTGGGAGCAG SEQ ID NO: 2 |
| Osteonectin | AGAATGAGAAGCGCCTGGAG SEQ ID NO: 3 | CTGCCAGTGTACAGGGAAGA SEQ ID NO: 4 |
| GAPDH | GTCAGTGGTGGACCTGACCT SEQ ID NO: 5 | ACCTGGTGCTCAGTGTAGCC SEQ ID NO: 6 |

Alkaline Phosphatase Staining

Cells were cultured on materials for 28 days. Noggin (50 ng/ml) was added in a set of samples and phosphate deposition was analysed by an Alkaline Phosphatase assay (Sigma, 86C-1KT). Cells were fixed with the fixative solution (citrate-acetone-formaldehyde solution) at RT for 30 s. Afterwards, samples were stained with the alkaline-dye mixture and incubated at RT in darkness for 15 min. Samples were counterstained for 2 minutes with neutral red solution and rinsed in tap water.

Statistical Analysis

The Tukey-Kramer method was used with multiple-comparisons post-test analysis of variance (ANOVA).

Results and Discussion

Figure 1:
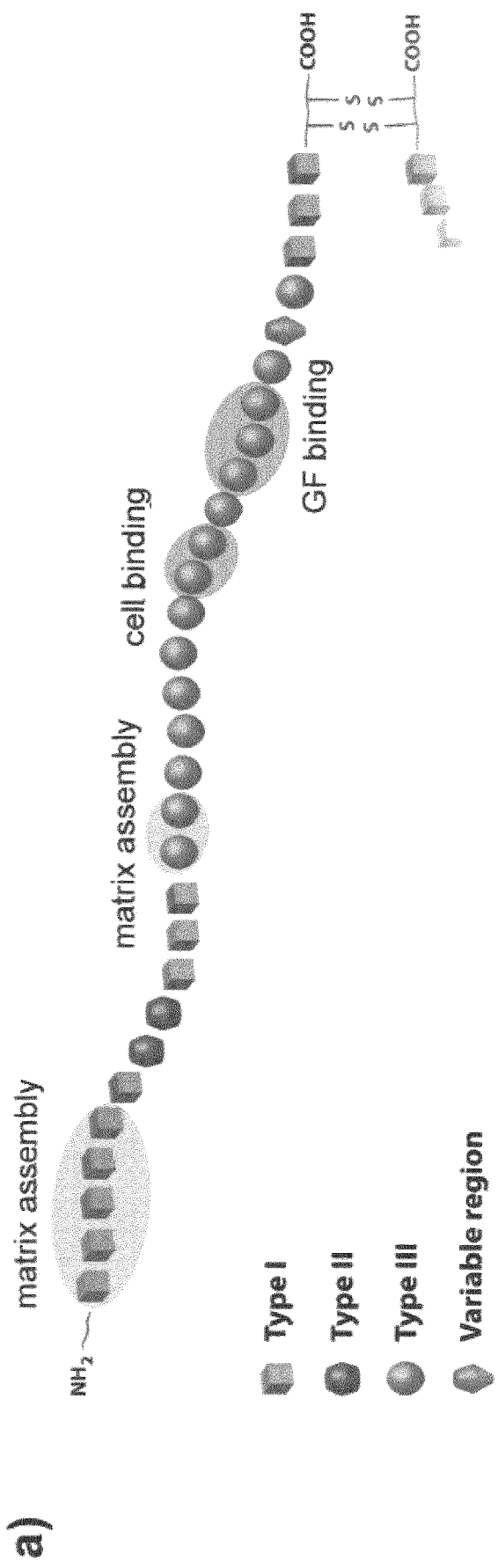
FIG. 1. Material-driven fibronectin (FN) fibrillogenesis. a. FN contains three types of domains that promote integrin binding (III9-10), growth factor sequestration (III12-14) and FNFN interactions (I1-5). b. Material driven FN-fibrillogenesis results in a FN (nano)network that is spontaneously assembled on the material surface of PEA but not on PMA. c. The assembly of FN at the material interface allows synergistic integrin-GF receptor signalling to direct stem cell differentiation.
Figure 1:
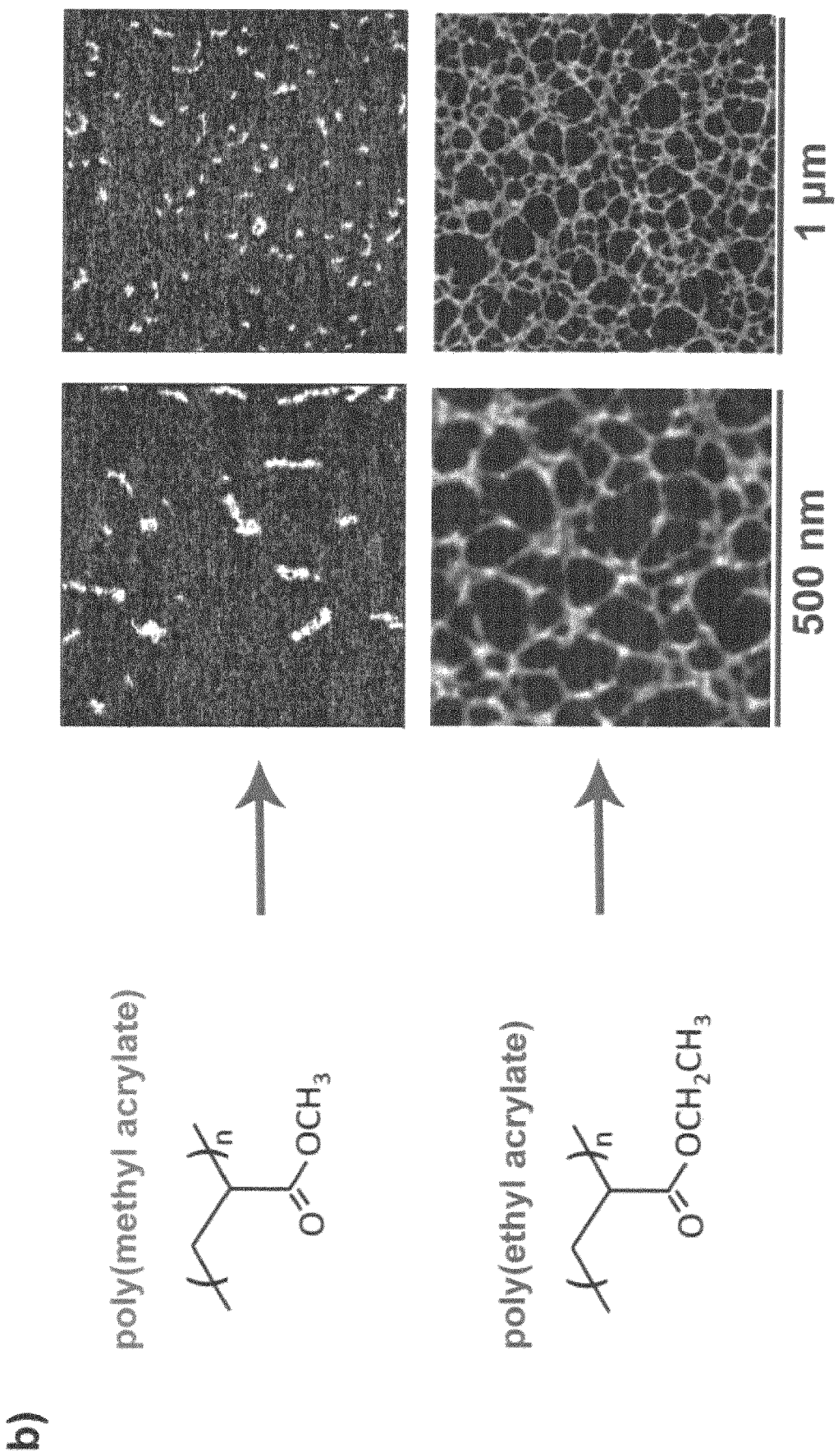
Figure 1:
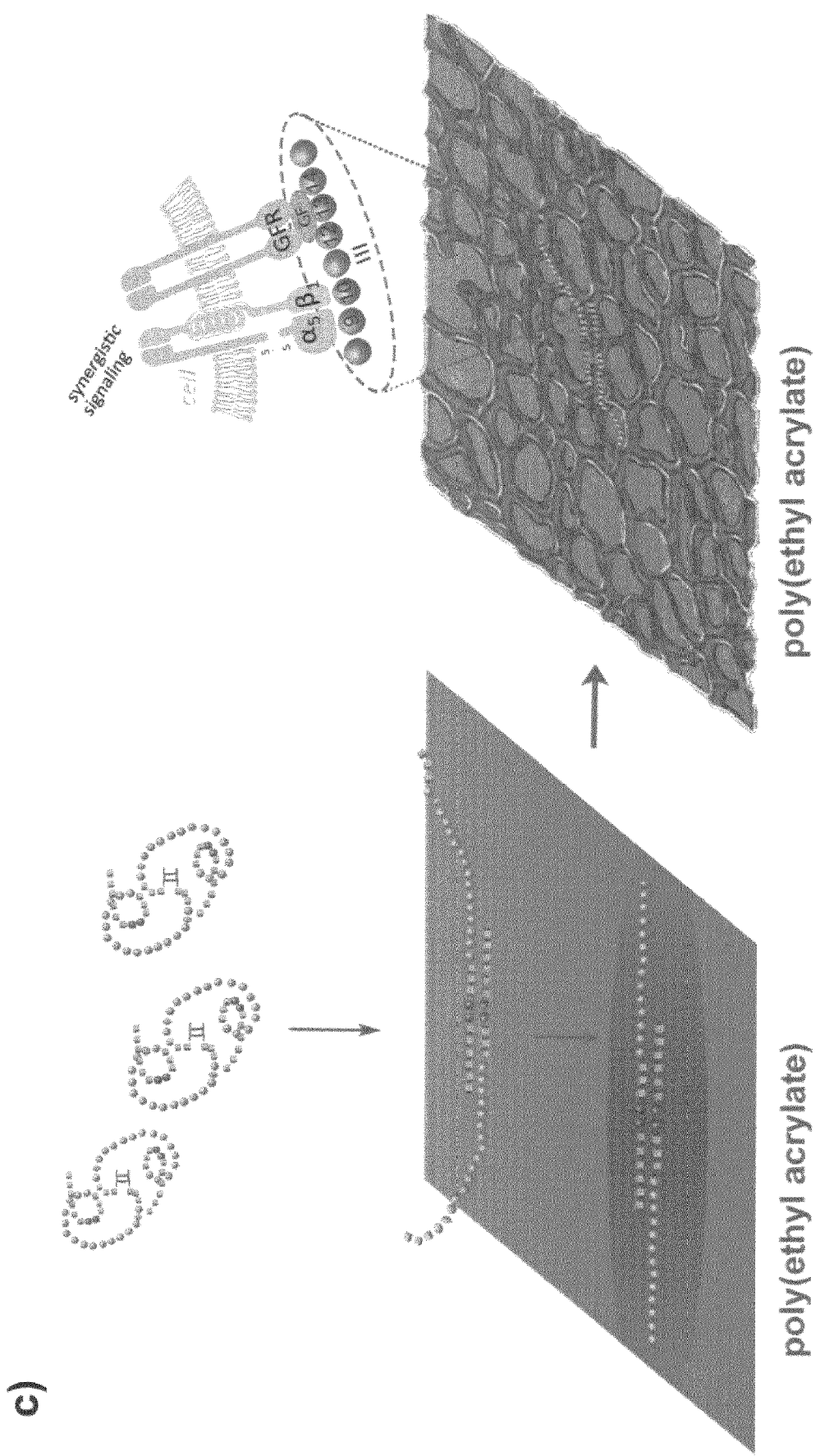

Fibronectin (FN) is a glycoprotein which forms dimers consisting of two subunits (~220 kDa) linked by a single disulfide bond near the carboxyl termini. Each subunit contains three types of repeating modules (types I, II and III), which mediate interactions with other FN molecules ($FNI_{1-5}$, $FNIII_{1-2}$), other extracellular matrix (ECM) components, integrins ($FNIII_{9-10}$) and GFs ($FNIII_{12-14}$) (FIG. 1a) (14). Cells primarily interact with FN via integrins, a family of transmembrane cell adhesion receptors. Integrin-mediated adhesion is a complex process that involves integrin association with the actin cytoskeleton and clustering into supramolecular complexes that contain structural proteins (vinculin, talin, tensin, etc.) and signalling molecules (FAK, Src, etc) (15). We have shown that adsorption of individual FN molecules onto a particular surface chemistry—poly (ethyl acrylate), PEA—induces exposure of self-assembly sites ($FNI_{1-5}$) to drive FN assembly at the material interface (FIG. 1b) (16). We have demonstrated that this process involves the 70 kDa amino terminal fragment of FN, which is the hallmark of physiological, cell-induced, FN fibrillogenesis (22), giving rise to a new process which we refer to as material-driven FN fibrillogenesis (FIG. 1c) (12). Poly (methyl acrylate) is used as a reference polymer on which FN is adsorbed and maintains a globular conformation as in solution (FIG. 1b). PMA behaves similarly to PEA in terms of surface wettability, stiffness and total surface density of adsorbed FN (FIG. 1b) (12).

Figure 2:
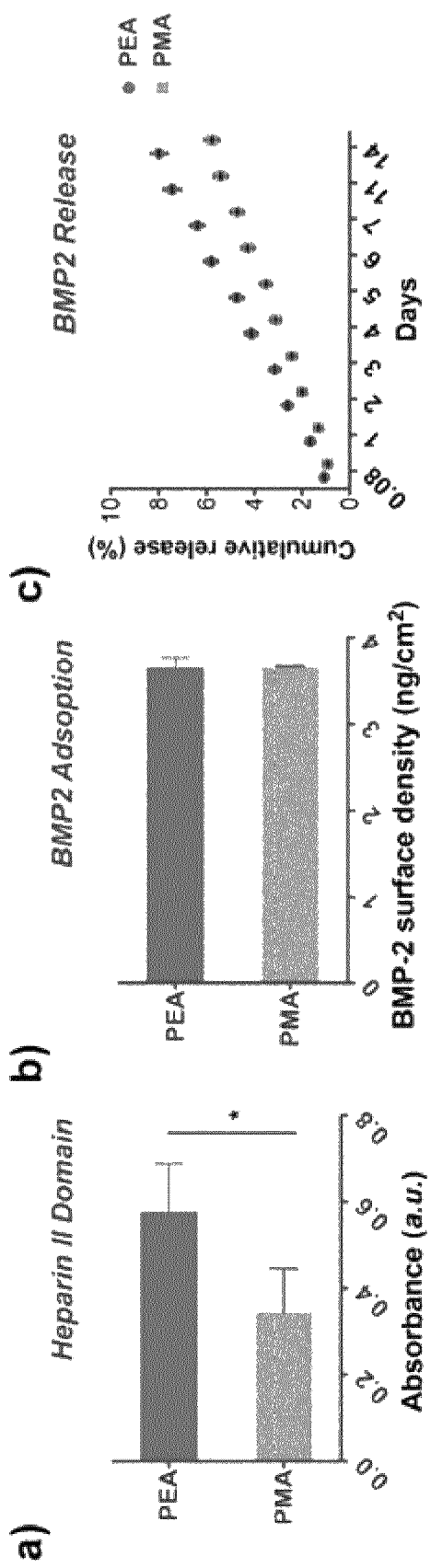
FIG. 2. Interactions between BMP-2 and FN on material-driven FN (nano)networks. a. Fibronectin organised into fibrils on PEA displays higher availability of the GF binding region ($FNIII_{12-14}$) than FN adsorbed on PMA in a globular conformation. b. Similar surface density of BMP-2 on FN-coated PEA and PMA occurs regardless of the organisation and conformation of FN on both surfaces. c. Cumulative release of BMP-2 over 14 days as determined by ELISA. d. AFM images at different magnifications after the sequential adsorption of FN (3 µg/ml) and BMP-2 (25 ng/ml) on PEA and PMA. No trace of FN and BMP-2 interactions were found on PMA whereas FN molecules in an extended conformation with globular aggregates compatible with BMP-2 molecules are displayed on PEA. e. AFM images of BMP-2 interacting with FN molecules on PEA. A secondary antibody bound to a 15 nm gold nanoparticle was used to univocally identify BMP-2 on the material surface. Symbols show statistical significant differences with all the other conditions on PEA (* p 0.001). f. Bare PEA and PMA surfaces. g. BMP-2 directly adsorbed on PEA and PMA (without FN) are seen as individual globules.
Figure 2:
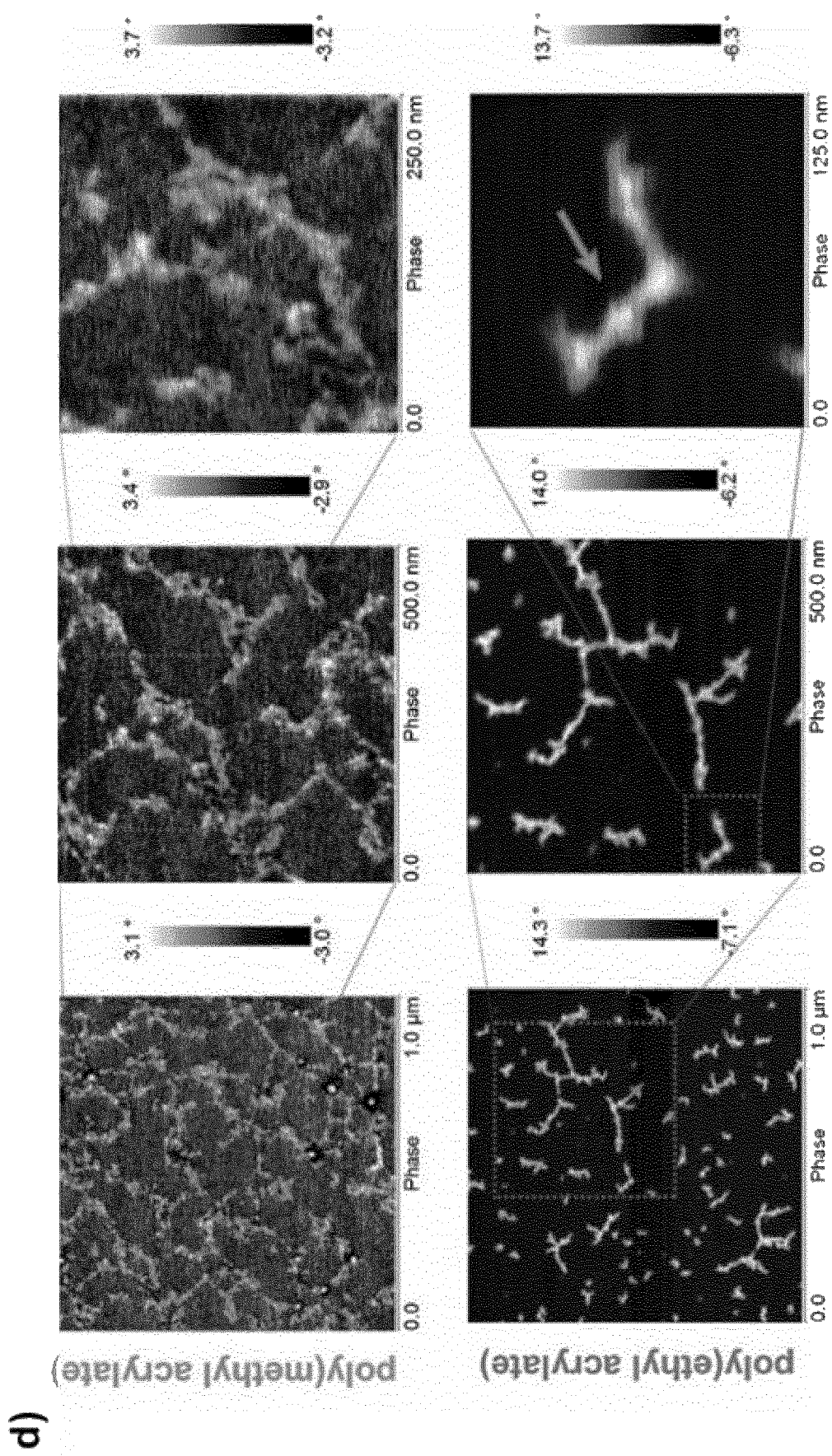
Figure 2:
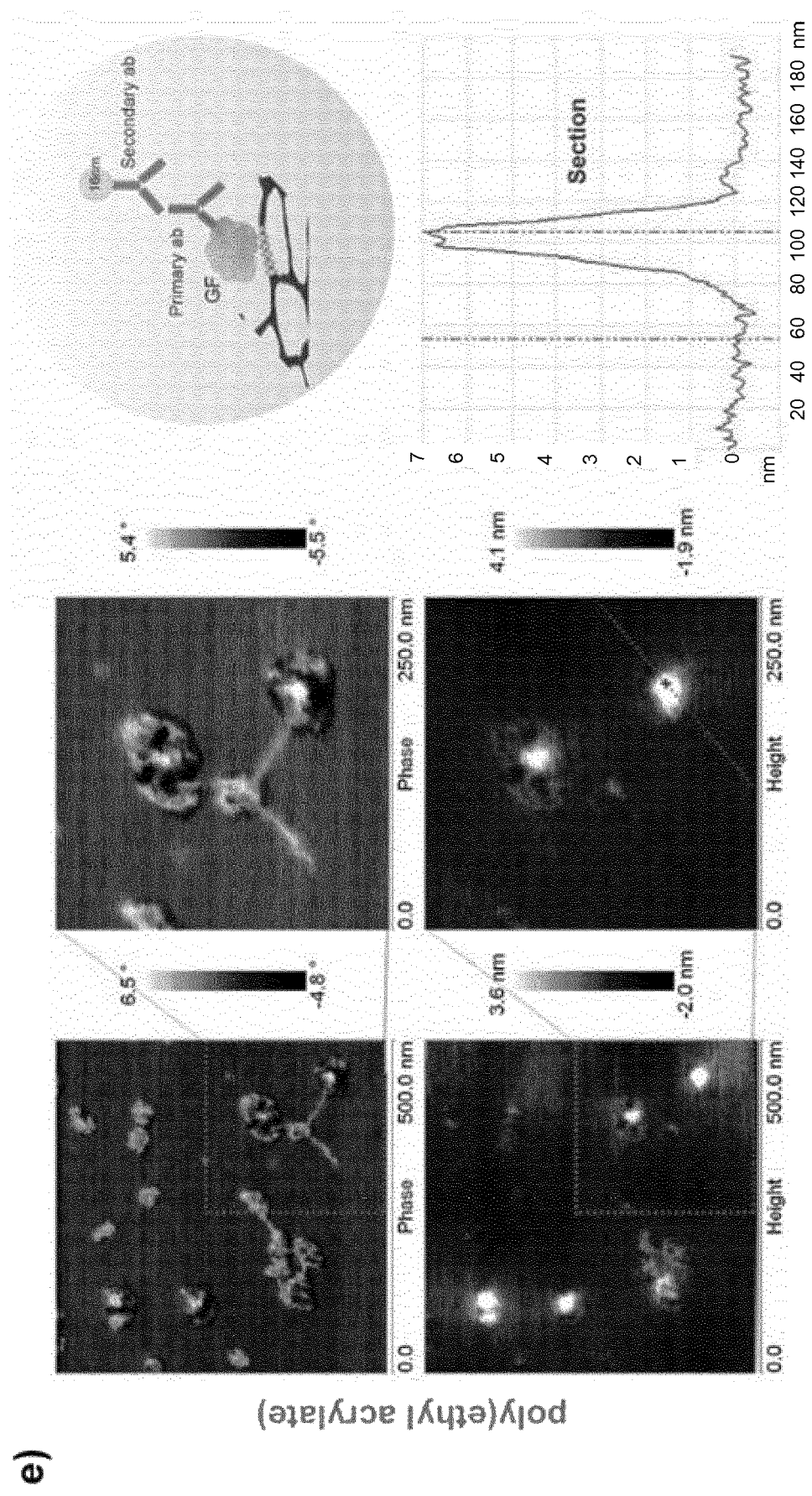
Figure 2:
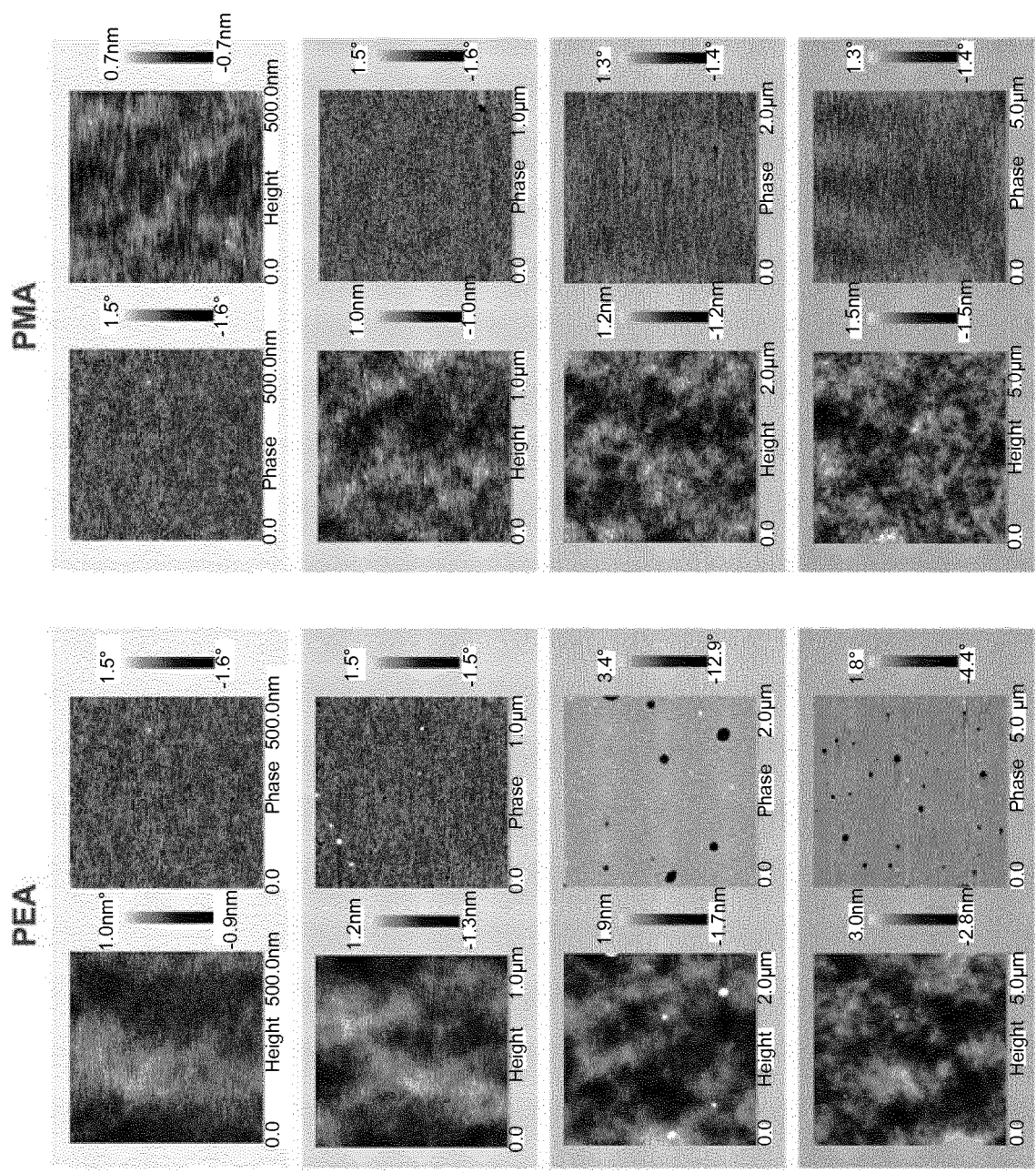
Figure 2:
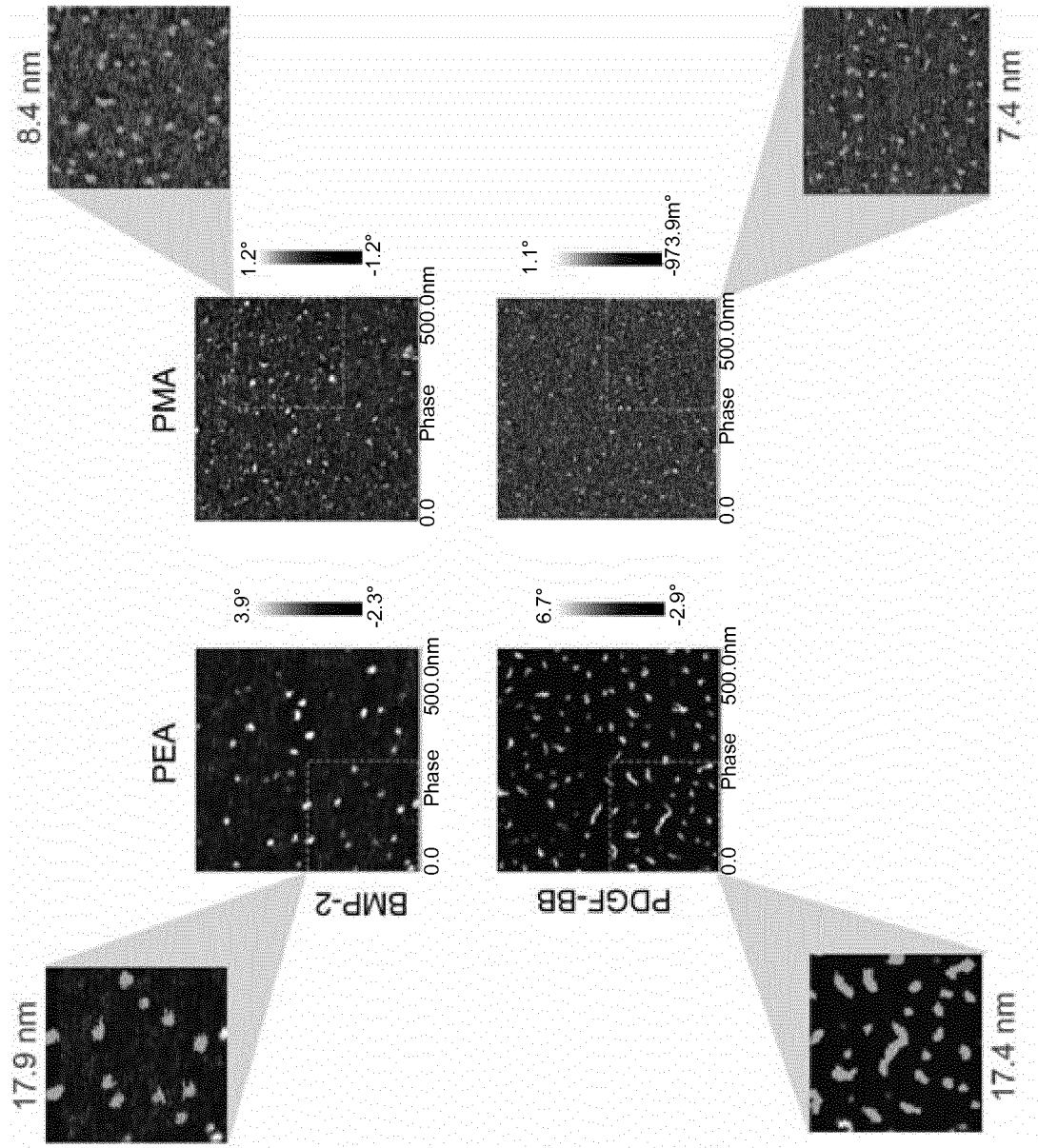

FIG. 2 shows that FN was adsorbed on PEA in a conformation that favours the simultaneous availability of the GF binding domain ($FNIII_{12-14}$) next to the integrin binding region ($FNIII_{9-10}$) (FIG. 2a) (17). Note that this change in the structure of FN occurs without the application of external force, a well-known method to alter the exposure of cryptic type III domains (18). Then, upon adsorption on FN-coated material surfaces, BMP-2 was sequestered by the (nano)network of FN fibrils assembled on PEA but not by globular FN adsorbed on PMA. The total surface density of BMP-2 on these two FN-coated surfaces, quantified by ELISA, was similar for PEA and PMA (FIG. 2b). BMP-2 remained stably adsorbed on these surfaces as a function of time, with less than 10% released after 14 days (FIG. 2c).

AFM images show that BMP-2 was preferentially adsorbed on top of FN molecules on PEA, whereas no evidence of any direct interactions between FN and BMP-2 occurred on PMA; on PMA the GF was preferentially adsorbed on the polymer surface (FIG. 2d). Bare PEA and PMA surfaces are shown (FIG. 2f). BMP-2 molecules directly adsorbed on PEA and PMA (without FN) are shown as individual globules (FIG. 2g).

FIG. 2e shows molecular scale AFM images of individual BMP-2 molecules sequestered on top of FN dimers previously adsorbed on PEA where the FN has an extended conformation (open arms) (21). To confirm that these globular-shaped molecules that interact with FN on PEA do correspond to BMP-2 molecules, we have adapted a technique that involves a secondary antibody bound to a 15-nm gold nanoparticle (19). The identification of BMP-2 molecules was then assessed using first an anti-BMP-2 antibody and then a gold-labelled secondary antibody that allows the unequivocal identification of these gold nanoparticles in AFM images (FIG. 2d). Individual FN molecules were simultaneously observed on PEA by using the phase magnitude in AFM (as described for direct observation of proteins on material surfaces (20)), with gold nanoparticles depicted using the height magnitude. A high resolution AFM image of one of these FN molecules in an extended conformation adsorbed on PEA with one gold nanoparticle per FN arm is shown in FIG. 2e. The section shows a height profile that is compatible with the dimensions of the gold nanoparticles buried within the antibody cluster.

Figure 3:
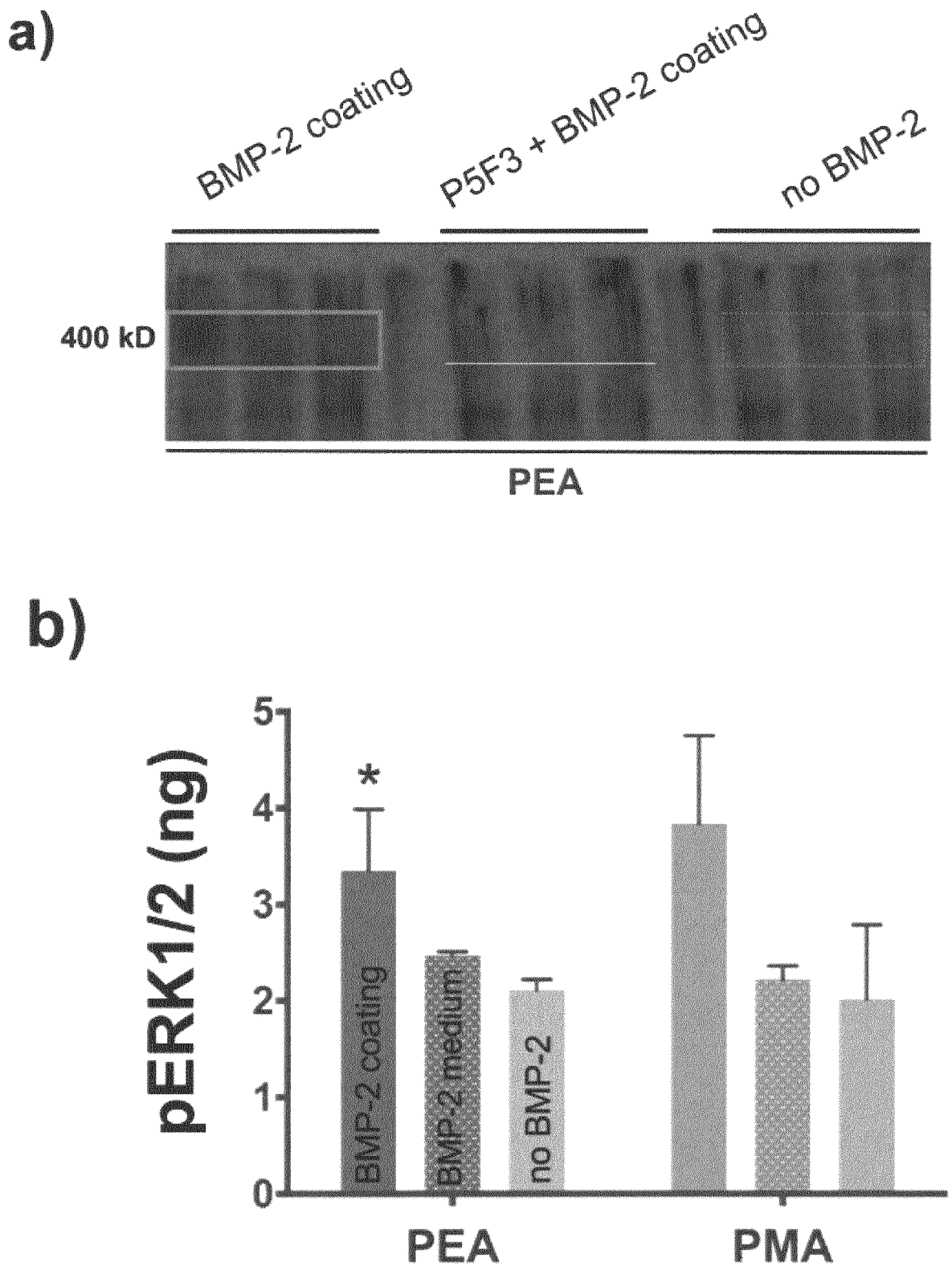
Figure 3:
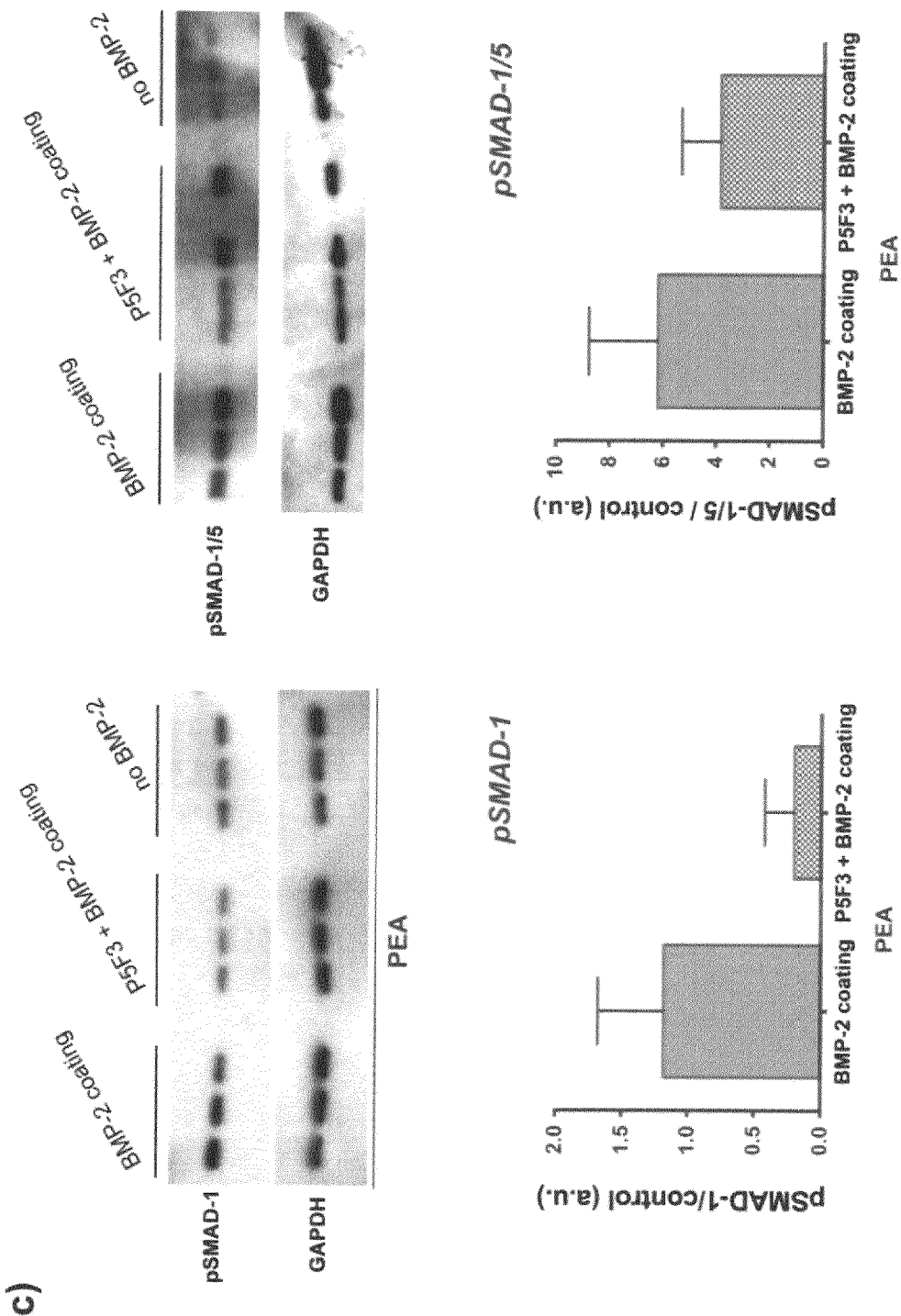

After having verified that FN adsorbed on PEA in the form of (nano)networks sequestered and retained BMP-2, we tested whether this material-based platform allowed co-ligation of integrins and BMP-2 receptors to modulate signalling and direct mesenchymal stem cell (MSC) differentiation more efficiently (i.e., with lower BMP-2 doses) compared to the presence of soluble BMP-2. Co immunoprecipitation of integrin β1 and BMP-2 receptors showed that clusters of β1 integrins and BMP-2 receptors were formed only when BMP-2 was presented via the FN network assembled on PEA (FIG. 3a), and that these integrin-GF receptor clusters were much less defined on either FN (nano)networks assembled on PEA without any BMP-2 or if the GF binding site of FN ($FNIII_{12-14}$) had been previously blocked with a monoclonal antibody to prevent binding of BMP-2 (FIG. 3a—note that when doing co-IP on 13 mm diameter coverslips we are dealing with vanishingly small amounts of protein and so the blot has to be overexposed). The formation of these BMP-2 receptor/integrin clusters had clear effects in terms of subsequent cell signalling. First, integrin regulated signalling through the phosphorylation of the mitogen activated protein kinase ERK1/2 (21) was higher for MSCs that bind BMP-2 sequestered on FN fibrils compared to standard delivery of BMP-2 as a soluble factor in the culture medium (FIG. 3b). Interestingly, however, no significant difference in ERK phosphorylation was noted between PEA and PMA. This suggests that non-canonical BMP signalling (BMP signalling through mitogen activated protein kinases) (21, 22) was enhanced by the presence of immobilized BMP-2 at the material interface, but that synergistic presentation conferred no advantage. However, as well as initiating non-canonical BMP signalling, e.g. ERK, BMP-2 can also initiate canonical signalling through Smads (small mothers against decapentaplegic) 1/5/8 that are phosphorylated by BMP-2 type I receptor (BMPR1) and then translocated into the nucleus to activate RUNX2 (runt related transcription factor 2—the osteogenic master transcription factor) (23). At the transcript level, Smad 1 and 5 were not affected by BMP in absorbed or soluble format and this observation concurs with previous reports (3). However, FIG. 3c shows that Smad 1 phosphorylation was significantly increased when BMP-2 is presented after binding to FN assembled on PEA, i.e. in synergistic conformation. Phosphorylation of Smads 1/5 was also significantly higher in MSCs on BMP-2 sequestered on FN (FIG. 3c). Blocking the GF binding region of FN ($FNIII_{12-14}$) with the P5F3 antibody and adding BMP-2 in the medium reverse pSmad-1 and pSmad1/5 phosphorylation to control levels, confirming that enhanced Smad signalling is due to BMP-2 bound to the integrin binding FN region. These results support that enhanced canonical BMP-2 signalling is a consequence of the simultaneous occupancy of integrins and BMP-2 receptors (23).

FIG. 4 shows qPCR results for osteogenic markers and the corresponding immunofluorescence images. Significantly higher osteocalcin and osteonectin expression was found both at the transcription and protein levels when BMP-2 was adsorbed on FN fibrils on PEA and hence presented synergistically. Importantly, this system was significantly more effective than the soluble administration of the GF alone. Also, when the same experiments were done using PMA—where FN was adsorbed in a globular conformation and no GF binding occurred on FN—the level of cell differentiation was the same regardless the route used to present the GF (FIG. 4a—OCN and FIG. 4b—ON). These results suggest that the presentation of BMP-2 was less effective after non-specific adsorption of PMA compared to the physiological presentation after FN sequestration, perhaps due to BMP-2 not being presented at integrin binding sites. These results indicate that the presentation of BMP-2 in synergy with adhesion sites on FN on PEA is more effective at triggering MSC osteoblastic differentiation compared to both the same concentration of the GF on PMA and the soluble administration of the GF. FIG. 4c shows that bone related alkaline phosphatase (ALP) activity was higher when BMP-2 was presented bound on FN on PEA compared to the soluble administration. FIG. 4c further demonstrates that blocking of the BMP-2 receptor with noggin reduced PEA driven FN/BMP-2 osteogenic differentiation further implicating BMP-2 signalling.

Over the last decade, there has been major focus on materials chemistry, stiffness and nanoscale topography and how these parameters control MSC fate (24-30). In vivo, the synergistic presentation of structural and signalling proteins is key to MSC regulation in the niche to control cell growth and differentiation in response to tissue regenerative demand with discrete areas of the niche having specific roles (1). Furthermore, the critical importance of protein conformation is now being shown in vitro (31, 33). Until now, however, a simple engineered system that allows reliable control of this interface, and synergistic signalling within the interface, has been elusive. Our approach is facile, in that the surface can be spin coated onto planar substrates or plasma polymerised onto complex 3D substrates (34). It is a material-based system that does not require either complex protein engineering or surface chemistry.

Instead it takes advantage of the ability of certain synthetic polymers to spontaneously organise adsorbed FN in a conformation that allows BMP-2 to bind and be presented in a cell-exploitable manner.

It is interesting to observe that controlling the synergy of the interface may be key to fully unlocking the potential of future biomaterials. Here it was shown, and agrees with previous work (35), that while FN fibrillogenesis gives a physiological-like conformation to FN, this is not enough in itself to increase osteogenesis in a major way. Rather it is the ability of this biomimetic network to interact with GFs that provides the desired bioactivity. Such observations may help explain how nature can combine cues to give far better cell control than current engineering approaches allow.

The system can be further exploited with other growth factors that bind FN, including vascular endothelial growth factor (VEGF), and platelet-derived growth factor-BB (PDGFBB), transforming growth factor-β and other GFs engineered for super-affinity to the extracellular matrix (3, 4).

Cell Culture Surfaces with VEGF to Promote Vasculogenesis

In this study, a PEA surface coated with fibrillar FN was tested for VEGF binding followed by interaction with endothelial cells (FIG. 5c) in order to investigate its potential to enhance vasculogenic response in comparison with a system using a similar polymer where no FN fibrillogenesis is happening. Specifically, we explored effects of two synthetic biocompatible polymers, PMA and PEA on promoting vasculogenesis in vitro. These polymers are very similar in structure but dramatically differ in interaction with specific proteins, and particularly with FN, a protein crucial for ECM formation and function. PEA triggering spontaneous FN fibrillogenesis allows FN binding domains to be available, and enables particularly the heparin binding domain ($FN_{III\text{-}12\text{-}14}$) known to bind growth factors, and the integrin binding domain ($FN_{III\text{-}9,10}$), to be available for ligand binding at the same time. In this study, the focus was on VEGF signalling that is crucial for initial stages of vascularization events. A detailed role of secreted GFs and cytokines orchestrating this process has still not been fully elucidated, however a prominent role of VEGF family and its membrane receptors has been repeatedly described (40), as well as importance of FGF (41). Although contribution of ECM proteins might seem to be less important, recent findings show the opposite: The complex ECM structure consisting from proteins such as fibrin, fibronectin, collagens, laminin and others serve not only as a mechanical scaffold for cell migration and proliferation and for non-specific detention of GFs but create rather a dynamic environment able to bind cells and GFs specifically, forming gradients and possibly releasing them on demand during proteolytic degradation of its components (42, 43). We showed that VEGF specifically binds to FN domains on PEA but not on PMA, and we observed that vasculogenic response of HUVEC seeded on VEGF modified FN-PEA surface was significantly higher than on PMA substrate with the same conditions. In addition, EKR1/2 phosphorylation in HUVEC was increased only when VEGF was bound to FN-coated PEA, while soluble VEGF did not show any difference from the control without GF. These results clearly show that VEGF bound to FN fibrils on PEA are presented in a very efficient way to direct HUVECs towards vasculogenic response. This can be explained by VEGF immobilization on FN in close vicinity of the RGD domain which after cell adhesion provides a unique condition for VEGF receptor-2 to interact with bound integrins, so intracellular signalling can be enhanced and results in stronger effect on cell migration, proliferation and differentiation. Facilitating this, PEA represents a promising material that can be used for efficient presentation of different GFs in very low concentrations, and thus being advantageous in various tissue engineering applications.

Materials and Methods

Preparation of Polymer Surfaces

Poly(methyl acrylate) (PMA) and poly(ethyl acrylate) (PEA) sheets were obtained by radical polymerization of methyl acrylate and ethyl acrylate solutions using 1% and 0.35% benzoin as photoinitiator, as described above. Thin films used for experiments were prepared by spin-coating cleaned glass cover slips with PMA (6%) and PEA (2.5%) solutions in toluene for 30 s at 3000 rpm and 2000 rpm, respectively. Before use, samples were oven dried at 60° C. and vacuum extracted.

Substrate Functionalizing with Proteins

Spin-coated polymer substrate samples were sterilized under UV for 20 min; then, polymers were coated with FN solution (20 μg/ml) for 1 h, washed with PBS, and coated with VEGF solution (25 ng/ml) for 1 h. Control samples without either FN of VEGF were incubated in PBS for the same time as coated samples. After this, functionalized substrates were washed with PBS and were ready for further experiments. All incubations were carried out at room temperature.

Atomic Force Microscopy

Functionalized substrates were washed three times with ultrapure water followed by drying with nitrogen. Sample surfaces were imaged with atomic force microscope NanoWizard 3 (JPK) using MPP cantilever (Bruker) with spring constant 5 N/m and resonance frequency of 75 kHz in tapping mode.

ELISA Assays

VEGF bound to substrates was assayed indirectly by measuring remaining VEGF in coating solution with a sandwich ELISA kit according to the manufacturer's instructions (DuoSetDY293B, R&D Systems). Levels of phosphorylation of ERK1/2 in HUVECs seeded onto functionalized surfaces were assessed after 30 min incubation using DuoSet ELISA kit following the manufacturer's instructions (DuoSetDYC1018B, R&D Systems).

Immunogold Reaction

Samples coated with FN and with and without VEGF coating were fixed with 4% formaldehyde, incubated with primary antibody against human VEGF (sc-57496 Santa-Cruz Biotechnologies) diluted 1:50 in PBS for 1 h, and after three washes with 0.5% TWEEN 20 in PBS, goat anti-mouse secondary antibody labeled with 15 nm gold nanoparticles (Aurion 815.022) was added in dilution 1:20 in PBS and left to react for 1 h. After immunoreaction, excess of secondary Ab was removed by two PBS washes; samples were fixed with 4% formaldehyde, washed three times with ultrapure water, then gently dried with nitrogen and imaged with AFM.

Cell Culture

Human umbilical vein endothelial cells (HUVEC) (Cellworks) were maintained in HLVEC complete media (Cellworks). For any experiment, cells with not higher than 10 population doublings were used (usually corresponding up to P5). For network formation experiments, cell seeding density was optimized, and cells were eventually seeded at 10,000 cells/cm$^2$. Seeding was done on protein-functionalized and control polymer-coated substrates, and cells were left to adhere in a $CO_2$ incubator at 37° C. After 16 h, medium was removed and replaced with fibrinogen solution (20 mg/ml) in HLVEC complete media, containing also 50 U/ml of thrombin and 1.2 mg/ml of aprotinin; to allow complete fibrinogen clotting, samples were placed in $CO_2$ incubator for 1 h. After clotting, fibrin matrix was covered with 0.5 ml HLVEC complete media with 25 ng/ml of VEGF where required, and samples were kept at 37° C. for 6 day period, with media changed every second day. For phosphorylation experiments, cells were seeded at density 15,000 cells/cm$^2$ on protein-functionalized and control polymer-coated substrates, and incubated in $CO_2$ incubator at 37° C.; after 30 min, cells were washed with PBS, and then incubated with lysis buffer for 15 min on ice; cell lysates were harvested and stored at −80° C. until assayed.

Fluorescence Staining and Imaging

Prior to staining cells in fibrin matrix, cells were washed with PBS, and then they were fixed with 4% formaldehyde, and permeabilized with 0.1% TRITON X-100 in PBS. Cytoskeleton was labelled with BODIPY-FL Phallacidine (Life Technologies) diluted 1:100 in PBS, and nuclei were stained with Hoechst 33342 (NucBlue, Life Technologies) using 1 drop per 0.5 ml PBS. Images were taken with fluorescence microscope Zeiss Observer Z1 using green and blue filters; 5 areas were imaged per each sample.

Data Analysis

Image analysis for cell alignment in fibrin matrix samples was done in ImageJ using routine object counting, and area and length measurement algorithms (details in FIG. 11). Ten areas were analyzed for each sample, and means and standard deviations were calculated. For ELISAs, samples were assayed in triplicate, and means and SD were calculated. For statistical analysis, one way ANOVA with Tukey's post-test was performed where needed using GraphPad Prism5 software.

Results and Discussion

As the first step of this study, characterization of VEGF binding to our modified surfaces was necessary. For that, we performed two types of experiment: an ELISA to quantify the amount of GF that is bound to the surface, and AFM to visualize the protein on our substrates. Then, HUVEC culture on the surfaces was optimized with fibrin gel being used as matrix, and different parameters of cell behaviour like cell spreading, attachment and morphology were assessed, focusing on cell potential to align and to form a network, a prerequisite for vascular tube formation. Finally, level of phosphorylation of ERK1/2, a downstream effector of VEGF stimulation pathway, was estimated to compare an effect of surfaces on VEGF signaling.

VEGF Visualization on Polymer Substrates

We assumed that considering the size of growth factor molecule and the fact that FN on PEA is present in form of stretched fibers, we should be able to see additional structures in samples that were incubated with VEGF in comparison with samples in PBS only by scanning the surface with AFM. Indeed, a higher degree of thickening of FN fibers was observed in VEGF positive samples than in control samples (FIG. 6a). In order to be able to detect an approximate position of this thickening, lower FN concentration was used for polymer coating, so individual FN molecules/dimers could be seen. However, because this direct technique of VEGF visualization was lacking a proof of specificity, we performed immunogold reaction to strengthen an evidence of VEGF presence on PEA. An interaction of bound VEGF with specific antibody was detected by a secondary antibody labelled with gold nanoparticles of bigger height than of FN network on the polymer surface; bound nanogold was then visualized with AFM. For this, we used PEA samples as well as PMA samples, both with and without VEGF coating. From FIG. 6d it is apparent that VEGF was present only in FN-coated PEA samples treated with this growth factor, while FN-modified PMA samples after VEGF treatment did not show almost any gold nanoparticles attached to the surface. Both PEA and PMA controls without VEGF coating were nanogold-negative, the PEA sample confirming specificity of the immunoreaction.

VEGF Quantification

For assessment of total amount of VEGF bound to the surfaces, an indirect ELISA was employed. As can be seen from FIG. 6b, the concentration of VEGF on PEA surface was higher than on PMA; however, this difference was not statistically significant. From an experiment assessing availability of GF binding domains of FN in the same systems (FN-coated PMA and PEA) which showed significantly higher availability of these domains on PEA in comparison to PMA (FIG. 6c), it is expected that at least a part of VEGF detected by ELISA on PMA is bound non-specifically. Non-specific VEGF binding to FN-coated PMA is also supported by results from AFM/ImmunoGold experiments, where no VEGF was found on PMA surfaces. As multiple washes are necessary for completing the immunoreaction, VEGF which was non-specifically bound to PMA (and detected by ELISA) was removed while specific binding to PEA was not affected.

HUVEC Network Formation

The two different polymer surfaces were then assessed in vitro for their ability to affect cell behaviour. HUVEC culture was used in an optimized setup where cells were first seeded onto polymer surface coated with FN and VEGF, after cell attachment the cultures were covered with fibrinogen solution that formed fibrin matrix, and finally the whole construct was immersed in growth media (FIG. 7a). In this system, cells on the polymer surface were receiving stimuli from the bottom layer while the top layer was providing a supporting 3D environment representing simplified extracellular matrix. After 6 days of incubation, cells seeded on PEA substrate showed clear 2D network alignment on the level of the polymer while on PMA substrate a cellular network was not as obvious and cell attachment was impaired (FIG. 7b). Moreover, cell sprouting into fibrin matrix was observed when cells were growing on PEA substrate (FIG. 7c). Quantification through image analysis of 2D events revealed significant differences between several parameters shown in FIG. 8. Even the total cell number between PEA and PMA coated substrates did not vary for individual conditions apart from higher populated controls with VEGF present in the medium; cell attachment and spreading was better developed on PEA surfaces when compared to PMA as shown by the total area coverage. This was also supported by larger single cell area on PEA surfaces when comparing PEA with PMA, both coated with FN only where no GF was present, and also comparing these two polymers coated with both FN and GF. An interesting observation that in case of PEA surfaces single cell area slightly decreased when VEGF was present while for all PMA surfaces stayed constant, suggests that individual cells can cover a smaller area when at higher level of cell organization (FIG. 8a). Analyzing parameters related to cell alignment, total lengths of aligned structures as well as average lengths of these structures were quantified together with a number of junctions per image (FIG. 8b). Statistical analysis of all these three parameters showed higher level of cell alignment on FN-coated PEA substrates with VEGF (both coating and in the medium) when compared to their respective FN-coated PMA controls. Total lengths and number of junctions were significantly higher in PEA-FN coated substrate samples coated with VEGF when compared to PEA-FN control without any GF which clearly shows that VEGF available on the surface of the substrate has a positive effect in HUVECs reorganization into aligned structures which is an early step towards forming primary vessels.

Effect on Phosphorylation in Signaling Pathway

The most direct way to look at VEGF effect on downstream signaling was to assess its receptor phosphorylation. An immunofluorescence test for presence of phosphorylated VEGFR-2 was performed on standard HUVEC culture on tissue plastics, when cells were stimulated with 25 ng/ml of VEGF for two different time periods (2 min and 30 min). After 2 min of stimulation the phosphorylated receptor was present while after 30 min incubation no phosphorylation was detected anymore (FIG. 12), which showed that the cells are stimulated by VEGF in the expected timescale. However, at the same time this result confirmed that the timescale when VEGFR-2 phosphorylation can be observed before it passes is too short for an experimental setup where VEGF is firstly adsorbed onto polymer surface and then cells are seeded on top, requiring some time to adhere. Therefore it was decided to assay phosphorylation of one of the downstream effectors, ERK1/2 which is activated via MAPK branch of GF receptor signaling. After 30 min incubation of cells with individual substrates, significantly higher phosphorylation was observed in cells on PEA than on PMA (FIG. 9), assuming that better signaling is related to better cell adhesion to PEA substrate in general. More importantly, differences were found also between PEA samples themselves: PEA substrates coated with VEGF showed higher level of ERK1/2 phosphorylation in comparison with PEA without bound VEGF as expected. Interestingly, PEA samples with VEGF present in the medium did not show any difference in ERK1/2 phosphorylation from PEA sample without VEGF (FIG. 9). This result was further consistent with phosphorylation level in PEA sample where VEGF was present both in the coating and in the medium, as this sample behaved the same as sample with VEGF coating only, with no additional phosphorylation coming from stimulation by VEGF from the medium. This indirectly proved the hypothesis about synergistic effect of FN-bound ligands, as only the adhered VEGF in close vicinity of integrin binding sites was able to stimulate cells, while VEGF in the medium did not have any effect at this early time point. Considering a fast onset of stimulatory effect when the cells are not even completely adhered, VEGF bound to FN appeared to be presented in very efficient way to deliver its message into the cell.

Many studies have been done on developing biosynthetic environments that would allow specific interaction with cells applicable in regenerative medicine. Long term focus is on incorporation of RGD motif into these systems to mimic integrin binding domains naturally present in ECM proteins facilitating cell adhesion, using RGD sequence prepared as synthetic peptide or as a part of recombinant proteins or their fragments, often covalently linked to different hydrogels or polymer matrices. It has been shown that also presence of other ECM protein domains, particularly GF binding sites is crucial for required cell response, and distribution of these two types of domains seems to be more efficient when being organized rather than random (44). There is an increasing evidence of GF receptor activation related to integrin stimulation during cell attachment leading to synergistic stimulatory effect on cell signalling e.g. in wound healing (3). For engineering of such synergistic environments, different strategies have been used for anchoring RGD motifs as well as natural or recombinant GFs to synthetic matrices based on poly(ethylene glycol), poly(lactic-co-glycolic acid) or cross-linked heparin, often requiring chemical syntheses and functionalization and/or genetic modifications (45, 46, 2).

In order to simplify the process of functionalized microenvironment preparation, we employed recently discovered PEA phenomenon of initiation of FN fibrillogenesis and network formation (47) to obtain a system that is very close to native ECM environment. Studies investigating cellular interactions with FN-coated PEA already showed enhanced biological activity of PEA-based system promoting myogenic differentiation (12) and stimulating protein remodeling (17). Recently, a study of FN-coated PEA substrates showed good availability of integrin binding domains (48), suggesting PEA as promising platform for directing cell behaviour in tissue engineering. Indeed, in a pilot study testing potential of FN-coated PEA substrate in bone differentiation revealed that PEA-FN-bound BMP-2 increased osteogenic marker expression in mesenchymal stem cells when compared with soluble BMP-2 (Virginia 2015). Here we focused on VEGF signalling that is crucial for initial stages of vascularization events, also because VEGF use in pro-angiogenic therapies was not very effective so far (49, 50). In this system, we tested whether FN molecules can expose more domains to the medium making them available for spontaneous interaction with VEGF and endothelial cells. As a control, PMA was used to compare interactions of FN in globular conformation with the same GF and cell type. We found a specific interaction between VEGF and FN molecules that was exclusively present on PEA samples but not on PMA surfaces, and subsequently showed that HUVECs vasculogenic response was significantly enhanced on VEGF-FN-coated PEA substrates in comparison with PMA surfaces treated in exactly the same way. On PEA, endothelial stimulation could take place thanks to highly efficient VEGF presentation in close vicinity of FN integrin binding domains. Advantage of this system over other strategies used so far stems not only from a small amount of GF used (once the GF coating is done prior cell attachment, no further GF supply was necessary) but also from very close mimicking of native ECM environment considering a natural VEGF bond to FN.

These results also show that although VEGF itself is critical in soft tissue repair (40) regulating events such as cell migration and proliferation of existing EC as well as recruitment of EC-progenitors and perivascular cells to the remodelling site, the importance of its crosstalk with integrins in endothelial cell signalling cannot be underestimated. It was shown that phosphorylation of VEGF receptor-2 (VEGFR-2) was prolonged in association with $\beta 1$ integrins (51), and ERK1/2 crucial for gene expression and DNA synthesis is phosphorylated as a result of activation of both, integrins and VEGFR-2 via FAK/Ras/Raf pathway and PLC$\gamma$/Raf pathway respectively (52, 53). In addition, Src activated by GF receptors can also stimulate FAK/Ras pathway (54) that is usually linked to integrin activity. Also PI3K stimulation leading to Akt activation for cell migration and survival is triggered by integrin-stimulated FAK as well as by phosphorylated VEGFR-2 (55). As the RGD domain of $FNIII_{10}$ binds particularly integrins $\alpha_5\beta_1$ and $\alpha_v$ dimers, we can hypothesize that these integrins are the molecules cooperating with VEGFR-2 stimulated by VEGF captured in our system that eventually leads to vasculogenic HUVEC behavior we could observe. The role of $\alpha_5\beta_1$ is supported by previous finding that in presence of VEGF in collagen, integrin $\beta_1$ recruitment and VEGFR-2 clustering was linked to increased DNA synthesis and cell migration (51). For the two $\alpha_v$ dimers known for their prominent role in vascularization, $\alpha_v\beta_3$ and $\alpha_v\beta_5$ integrins, two distinct pathways promoting angiogenic response were described: $\alpha_v\beta_3$ is crucial for angiogenesis after bFGF stimulation, while $\alpha_v\beta_5$ is necessary for VEGF stimulated response (56). As in our system we used explicitly VEGF, we expect the $\alpha_v\beta_5$ is taking part in HUVEC alignment stimulation rather than $\alpha_v\beta_3$. This might be also supported by the fact that endothelial constitutively expressed $\alpha_v\beta_5$ is activated after VEGFR-2 mediation (57) while $\alpha_v\beta_3$ expression is only induced after stimulation (54). However, the role of $\alpha_v\beta_3$ linked to FN cannot be ruled out as previous studies described $\alpha_v\beta_3$ role in VEGF-stimulated EC proliferation in vitro, although cells on FN showed much weaker response in comparison to cells plated on vitronectin, an ECM protein with an exclusive binding site for $\alpha_v\beta_3$ (58).

It is important to mention there are other integrin binding sites on FN molecule, specifically extradomain A and a variable region that are also very close to $FNIII_{12-14}$ and so close to the site where VEGF is bound. Because these modules are binding preferentially $\alpha_4$ integrins which are present mainly on B-cells, T-cells and hematopoietic stem cells, it is possible to expect that these integrins are not involved in endothelial cell activation observed in this study.

In order to deeper understand the mechanism in which our PEA-FN-GF microenvironments are able to stimulate endothelial cells, further studies are required to investigate the system, focusing particularly on what integrins are playing a role in the stimulation. Nevertheless, this study brings a proof that a simply engineered system with only a small input of proteins can serve as a stimulatory environment for triggering vasculogenic response which can be potentially used for much needed vascularization in tissue regeneration, as well as for sustained GF supply in various tissue engineering applications.

Construct for a Critical Size Bone Defect in a Small Animal Model

A 3 to 4 mm long hollow sleeve of biocompatible porous material was prepared with a PEA, FN and BMP-2 coating for use in a model of a critical size bone defect in a mouse radius. To create defects, the mid-section of the radius and the ulna in the right front paw of the mouse was exposed. A custom built bone cutter was used to precisely generate a 3 mm segmental defect on the radius without disturbing the ulna. A 3.5 mm long sleeve containing the materials was fitted over the ends of the defect, in contact with both distal and proximal bone ends. The sleeve does not interfere significantly with the healing process and no differences in bone formation were observed between empty sleeves and untreated defects. A sleeve filled with a PEG-based hydrogel loaded with a very high dose of BMP-2 was used as a positive control. Constructs were implanted in 3 to 5 animals per group, including a group only with PEA coating, a group with PEA, FN coating and BMP-2 coating, a group without FN coating, a group without BMP-2 coating, and control groups with empty sleeves and sleeves filled with hydrogel and BMP-2. The experiment was designed to minimize the number of animals used, as the evolution of the repair process is performed on the same animal, using in vivo techniques, after different time points.

Bone volume measured with pCT scans after 4 weeks showed a comparable response for the PEA+FN+BMP-2 group and the positive controls, as shown in FIG. 13. After euthanasia, constructs were explanted and evaluated for mechanical properties.

Materials and Methods

Implant Preparation

Polyimide implant tubes presenting holes were coated by solvent casting from solutions of the corresponding synthesized polymers PEA or PMA, creating a polymer layer on the tube. Implant tubes were dried under vacuum at 60° C. to remove solvent traces and were rinsed with milli-Q water several times before UV sterilization. FN (Sigma) was adsorbed overnight on the polymer layer from a protein solution of 20 µg/ml in PBS at 37° C. Then, 1% BSA/PBS solution was adsorbed for 30 min at RT to block non-specific binding sites before the adsorption of the BMP-2 growth factor (R&D systems) from a solution of 5 µg/ml in PBS for 1 h. The adsorption of the proteins was performed by creating vacuum to force the incoming of the solution into the implant tubes. After each protein adsorption, samples were rinsed in PBS to remove the non-adsorbed protein and finally the samples were kept in PBS until implantation. GFOGER-functionalized PEG-MAL hydrogels, which have been shown that promote osteogenic differentiation and bone healing of radial segmental defects (62), were used as a positive control. Hydrogels were synthesized by reacting the four-arm, maleimide-end functionalized (>95%) PEG macromer (PEG-MAL, 20 kDa, Laysan Bio) with the adhesive peptide GYGGGPG(GPP)5GFOGER(GPP)5GPC (GFOGER) (Activotec) and BMP-2 (R&D system), followed by mixing with VPM cross-linker (AAPTEC) at a volume ratio of 2:1:1:1. The final concentration of the BMP-2 growth factor in the hydrogels was 75 μg/ml. The concentration of VPM used was calculated to provide the same number of cysteine residues than the number of free (unreacted) maleimide groups remaining in the adhesive peptide-functionalized PEG-maleimide solution.

Bone Radial Segmental Defect Surgery

IRB and IACUC guidelines were followed to perform in vivo experiments. C57B1/6J male mice (8-10 weeks old, Jackson Laboratories) were anesthetized under isoflurane and the right forelimb was shaved and swabbed with isopropyl alcohol and chlorhexidine. After anaesthesia induction, mice were provided with a single dose of sustained-release buprenorphine for pain relief. An incision was made in the skin along the forearm and the muscle tissue over the radius was blunt dissected. A 2.5 mm defect was created in the centre of the radius by using a custom-made double-bladed bone cutter. The implant tube was placed into the defect by fitting it at the proximal and distal ends of the radial defect, and the incision was then closed with degradable vicryl suture. The defect created was checked by the imaging with a radiography system right after the surgery and before the recovery of the animal. Mice were monitored post-surgery for signs of distress, movement and weight loss.

Faxitron and uCT Imaging

The radial defects were imaged with the MX-20 Radiography Equipment (Faxitron, 23 kV energy, 15 s scan time) at different time points: 0, 14, 28, 42 and 56 days. For μCT imaging, a 3.2 mm length of the radius centred on the 2.5 mm radial defect was scanned in anesthetized live mice using a VivaCT system (Scanco Medical, 142 mA intensity, 55 kVp energy, 300 ms integration time, and 15 μm resolution) at 0, 4 and 8 weeks after surgery. Bone formation was evaluated by contouring 2D slices (including only the radius) which were used to obtain 3D pCT reconstructions, displaying the total length of the radius scanned. However, the quantification of the volume of new bone within the defect was performed by evaluating only the middle 2.0 mm of the defect, in order to ensure that only new bone formation was measured.

Histology

At the end of the experiment (8 weeks), mice were euthanized and radial bones were explanted, fixed in 10% neutral-buffered formalin solution, decalcified (Ricca, decalcifying solution) and embedded in paraffin. Sections 5 μm thick were cut and were deparaffinised before the Safranin-O/Fast Green staining. Samples were deparaffinized, rehydrated in water and incubated in Mayer's hematoxylin solution for 10 minutes. After rinsing in tap water, they were incubated in 0.5% fast green solution for 10 s and rinsed in 1% acetic acid for 3 s. Finally, samples were incubated in 0.5% safranin-O for 2 min, and then dehydrated and clear in xylene before mounting them using DPX.

Statistical Analysis

The Tukey-Kramer method was used with multiple-comparisons post-test analysis of variance (ANOVA).

Results and Discussion

We evaluated the potential of the synergistic presentation of GFs and adhesion sites on biomaterials in vivo using a murine non-healing radial bone defect model (62). This bone repair model has significant advantages: i) the 2.5-mm defect does not spontaneously heal, providing a rigorous critical-sized model, ii) it allows for simple in vivo imaging approaches (e.g. Faxitron, and μ-CT), iii) the ulna provides sufficient stabilisation of the defect and no fixation plates/hardware are required, thereby simplifying the surgical procedure and reducing the risk of infection; a major advantage over the rat calvaria and segmental femur defect models (62).

Implant consisted of polyimide sleeves (4 mm long, FIG. 15a) coated with a thin layer of the polymers PEA and PMA (green fluorescent dye in FIG. 15a). Then either FN or FN/BMP-2 was adsorbed on the cylindrical polymer surface. We used a very low concentration of BMP-2 which resulted in ~15 ng of BMP-2 on the wall of the coated tubes (surface density of 100±8 ng/cm$^2$ as measured using ELISA). This BMP-2 amount is still at least 50% lower than most advanced materials systems that have been tested in murine models based on integrin-specific PEG hydrogels loaded with BMP-2 (62). Note that even if human and rodents do not metabolise biologics at the same rate, the amount of BMP-2 we used is ~300 lower than the clinical standard (7). The material system is highly demanding as we intend to promote bone regeneration of a non-healing defect—a volumetric defect—by engineering the material surface of a tube where this volume is contained. This is fundamentally different to what has been done up to now to promote bone formation in vivo using engineered space-filling materials such as hydrogels and porous scaffolds (62). We have included a PEG hydrogel loaded with a 75 μg/ml of BMP-2 (~175 ng within the defect) as a positive control in FIG. 15. This represents more than 100 times the amount used in our system to achieve a similar quantitative result (FIG. 15c).

We evaluated bone healing by radiography and micro-computed tomography (μCT) at 4 and 8 weeks post-implantation (FIG. 15 a,b). We examined three groups for each of the coatings (PEA and PMA): 1) polymer only; 2) polymer coated with FN (20 μg/ml); 3) polymer coated with FN and BMP-2 (~15 ng). Results for pCT, including quantification of bone volume (FIG. 3c), show that only when FN and BMP-2 were adsorbed on PEA did the defect become fully repaired and bridged. Thus, the effect could only be ascribed to the simultaneous presence of FN and BMP-2 promoting enhanced activity of the GF. The sleeve coated with either PEA only or PEA+FN did not promote the same level of bone growth, although FN did have some effect by itself with PEA (FIG. 15b). Also, this very low amount of BMP-2 was not effective in promoting bone growth when presented on PMA surfaces with FN (FIG. 15b). This result supports the specificity of the synergistic integrin/GF receptor mechanism on PEA shown in FIGS. 3 and 4. Histological analysis at 8 weeks showed fibrous tissue with no significant bone formation within the defect for all the conditions except for PEA+FN+BMP-2 where bone formation and establishment of bone marrow in the centre of the defect was noted (FIG. 16). Higher magnifications images within the defect confirm different tissue architecture among PEA, PEA+FN and PEA+FN+BMP-2 (FIG. 15d). Without BMP-2 cells are organized along a fibrillar ECM with a fibroblastic morphology. However, on PEA+FN+BMP-2 cells are organized into cavities-like structures as in the bone marrow (arrows in FIG. 15d). There is also lack of bone marrow related structures in the cell organisation observed on PEA+FN (arrows).

The critical importance of protein structure in determining cell behaviour is known (31, 33, 34), but it has been challenging to translate this strategy into clinically relevant therapies. Here we describe a facile yet robust engineering approach that allows reliable control of synergistic integrin/GF signalling to promote stem cell differentiation and tissue repair. Notably, PEA can be readily applied to diverse biomedical devices, both planar and complex 3D geometries by spin coating, solvent casting and plasma polymerisation (35). We demonstrate that FN nanonetworks, simply adsorbed onto PEA from a solution, allow for simultaneous availability of the integrin binding region ($FNIII_{9-10}$) and the GF binding region ($FNIII_{12-13}$) (48) of this important extracellular matrix protein. The $FNIII_{12-14}$ region is classically described as the heparin binding region shown to be a promiscuous GF binding region able to sequester different GF families (e.g. PDGF, FGF, and TGF-b) (2). As a proof of concept, we show here that BMP-2 is bound onto the FN nanonetworks at the material interface and this binding/presentation promotes enhanced BMP-2 signalling in MSCs with very low doses of BMP-2 driving osteogenesis and complete repair of non-healing defects in vivo. It is critical to note that this is achieved at a ~300-fold less GF dose than clinical use with collagen sponge delivery. Remarkably, we show, for the first time, a surface-induced regeneration of bone (volume) in a critical size defect, emphasising clinical potential. Previous studies have shown the importance of FN conformation in driving osteogenic differentiation on material surfaces, with correct FN conformation required to allow enhanced availability of the integrin binding site (33). Coating implants with FN fragments leads to better osteointegration, which reveals the importance of integrin specificity related mechanisms also in vivo. Our results show a moderate effect for fibrillar FN nanonetwork presentation on PEA to induce osteogenesis both in vitro, as previously reported (36) and in vivo (FIG. 15). This may be related to the presence GFs in the regenerative environment (media/serum) which are adsorbed on FN nanonetworks to induce synergistic signalling.

Other strategies to present GFs from a material surface, including protein engineering techniques, the use of peptides that bind heparin and then GFs and the use of layer-by-layer technologies (5) have been shown to be more effective than the soluble administration of GFs but, critically, do not exploit synergy between GF and integrin receptors to accelerate healing. The potential importance of crosstalk between integrins and GFs was revealed in biological sciences more than a decade ago (13) and was explicitly engineered into a fibrin matrix using a recombinant fragment of FN consisting of $FNIII_{9-10}/_{12-14}$ that promoted bone regeneration and wound healing (3). More recently, it has been shown that matrix-bound BMP-2 induced integrin-dependent Smad signalling, which helped indicate that both receptors in synergy can potentiate each other to increase control over cell fate. Note that this work only presented BMP-2 from the material surface and it was hypothesised that cell secreted FN was used to promote receptor crosstalk and simultaneous integrin BMP receptor signalling. However, we have engineered the cellular microenvironment to target integrins and GF receptors synergistically with facile and translatable materials technology.

Currently, while widely employed in clinic for e.g. bone repair, the use of GFs has been only partially successful and even controversial. Our polymer system has the potential to drastically reduce GF dose and topically deliver the GFs to the site of regenerative demand, maximising effects by targeting integrins and GF receptors in synergy. Furthermore, the GFs remain bound and localized to the material and so off target effects should be reduced.

Cell Culture Surfaces with BMP-2 to Investigate the Effect of Surface Properties on Cell Differentiation Alkyl acrylate polymers having a vinyl backbone chain with the side groups —$COO(CH_2)_xCH3$, where x=0, 1, 3, 5 were prepared and used to surface coat a substrate as described herein. FN from plasma (Invitrogen) was then adsorbed on the different polymer surfaces by immersing the surfaces in FN solutions at concentrations from about 2 to 50 µg/ml in PBS. After adsorption, surfaces were rinsed in PBS to eliminate non-adsorbed protein. AFM was performed in the tapping mode immediately after FN adsorption to verify FN fibrillogenesis. BMP-2 from recombinant sources (R&D Systems) was then adsorbed on the different surfaces by immersing the surfaces in BMP-2 solutions at concentrations of 25 ng/ml. After adsorption, surfaces were rinsed in PBS to eliminate non-adsorbed protein. AFM may be performed in the tapping mode immediately after BMP-2 adsorption to determine BMP-2 sequestration by any (nano) network of FN fibrils assembled on the polymer surface.

The subtle variations in polymer chemistry led to differences in FN adsorption on the polymer surfaces: the same FN density was obtained on every polymer surface but the supramolecular organisation of the FN protein at the material interface was different for the polymer surface where x=0 and for the other polymer surfaces (where x=1, 3, 5). One set of polymer surfaces (x=1, 3, 5) produced the same supramolecular organisation of the FN protein, while the poly(methyl acrylate) (PMA) surface (where x=0) did not induce FN fibrillogenesis.

These polymers (x=1, 3, 5) may be used to further investigate the effect on cell behaviour of surface mechanical properties as the unique physical parameter, i.e. after ruling out any influence of the length of the side group on protein conformation, all while BMP-2 protein is being delivered at a low dose as a means to direct differentiation.

Cell Culture Surfaces with BMP-2 to Investigate the Mechanisms of Biomaterial-Extracellular Matrix Protein-Cell Interaction Polymer solutions were prepared from bulk co-polymers of poly(ethyl acrylate) (PEA) and poly(methyl acrylate) (PMA): PEA (100%), PEA/PMA (70/30), PEA/PMA (50/50), PEA/PMA (30/70) and PMA. As described herein, bulk polymers were synthesized by radical polymerization. Polymer solutions were made in toluene and thin films were prepared by spin-casting the polymer surface onto substrate samples. The substrate samples were then coated with FN and BMP-2, also as described herein.

These chemically similar polymer surfaces may be used to study the mechanisms that govern biomaterial-cell interaction, and cell processes like adhesion, migration and differentiation. While being chemically similar, these surfaces elicit structural conformational changes of FN resulting in a graded degree of FN organisation according to the content of the two polymers, with the same amount of adsorbed FN found on the surfaces. At the same time these systems allow the delivery of BMP-2 protein at a low dose as a means to direct differentiation.

The FN protein network conformation on these surfaces was verified using AFM in tapping mode as described herein. FIG. 14*a* shows height (a) and phase (b) AFM images on spin-coated samples for each of the polymer compositions. ELISAs may be carried out to characterise the availability of essential FN binding sites on these surfaces as described herein. The antibodies used may be directed against the flexible linker between the 9th and 10th type III repeats (HFN7.1 antibody) and the 8th type III repeat (mAb1937 antibody).

ELISAs may also be carried out to characterise BMP-2 adsorption on FN-coated samples. The supernatant from BMP-2 incubated samples was collected, and adsorbed BMP-2 was quantified by subtracting the amount of BMP-2 in the collected supernatants from the amount used in the coating solution. FIG. 14*b* shows the amount of BMP-2 on FN-coated and non-FN-coated surfaces used in this experiment. The amount of BMP-2 adsorbed on the FN-coated substrates decreases as the proportion of PMA in the co-polymer surface increases. The opposite is observed on substrate samples coated only with BMP-2 where BMP-2 adsorption is higher on PMA.

Cell culture experiments may be used to study cell migration behaviour. Adhesion experiments with the polymer surfaces described in this example showed that hMSCs attach and develop focal adhesions on all surfaces. FIG. 14c shows cell adhesion of hMSCs on FN/BMP-2-coated samples 1 d after seeding, with fluorescent staining of focal adhesion (red), actin cytoskeleton (green) and nuclei (blue). Migration experiments with the polymer surfaces described in this example showed that human fibroblasts maintain constant speed on PMA, whereas they get faster on PEA over time.

Material-Driven FN Assembly Promotes Maintenance of Mesenchymal Stem Cell Phenotypes Mesenchymal stem cells (MSC) are both a research tool to investigate self-renewal and differentiation as well as candidates for use in regenerative medicine. Significant efforts have been devoted to developing technologies to control stem cell fate, including the use of soluble factors in culture medium. However, material properties (e.g. stiffness, nanotopography) offer alternative approaches that avoid the use of soluble factors. Here, we report for the first time a material system capable to sustain growth of stem cells (maintaining stemness) as well as to promote highly efficient differentiation upon external stimulation. Poly(ethyl acrylate) (PEA) induces assembly of fibronectin (FN) into nanonetworks (FN fibrillogenesis) upon simple adsorption from solutions. Here, we show that these FN nanonetworks allow growth of MSCs and maintenance stemness for long periods of time (up to 30 days) using basal media in absence of soluble factors. Also, the system promotes enhanced levels of differentiation when defined supplemented media are used. Our study reveals the critical role of the intermediate protein layer (and consequently its conformation) at the material interface to control MSC fate regardless of the properties of the underlying material and it introduces a new material system as a candidate to be used in MSC niche design.

Materials and Methods
Materials

Polymers were synthesized by radical polymerization of methyl acrylate and ethyl acrylate (Sigma-Aldrich). The initiator was benzoin at 1 wt % and 0.35 wt % respectively (98% pure, Scharlau). Afterwards, the samples were dried to constant weight. Spin coating was used to coat glass coverslips and produce thin films of these polymers (Brewer Science). Polymer solutions were made in toluene with 6% PMA or 2.5% PEA and spun at 2000 rpm for 30 sec. Finally, samples were dried at 60° C. in vacuum. For cell culture experiments samples were sterilized by UV exposure for 30 min.

Atomic Force Microscopy

AFM was performed in a NanoScope III from Digital Instruments (Santa Barbara, CA) operating in the tapping mode in air; the Nanoscope 5.30r2 software version was used. Si-cantilevers from Veeco (Manchester, UK) were used with force constant of 2.8 N/m and resonance frequency of 75 kHz. The phase signal was set to zero at a frequency 5-10% lower than the resonance one. Drive amplitude was 200 mV and the amplitude setpoint Asp was 1.4 V. The ratio between the amplitude setpoint and the free amplitude Asp/A0 was kept equal to 0.7.

Protein Adsorption

Fibronectin (FN) from human plasma (Sigma-Aldrich) was adsorbed on the different substrates by covering the material films with FN solutions of concentration 20 µg/ml in Dulbecco's Phosphate Saline Buffer (DPBS). After adsorption, samples were rinsed in DPBS to eliminate the non-adsorbed protein.

Cell Culture

Murine embryonic mesenchymal stem cells (mMSCs) C3H10T1/2 (RIKEN Cell Bank, Japan) were cultured in Dulbecco's modified Eagle's growth medium (DMEM) with 10% fetal bovine serum (FBS) and antibiotics 1% (penicillin/streptomycin) at 37° C. in a humidified atmosphere of 5% $CO_2$. For differentiation experiments, mMSCs were plated on glass covers coated with FN, at a density of 10,000 cells/cm$^2$ for osteogenic and 30,000 cells/cm$^2$ for adipogenic differentiation and cultured for 48 h in DMEM growth media. After cells reached 70-80% confluence, differentiation was induced with osteogenic media consisting of DMEM growth medium supplemented with Ascorbic Acid 50 µg/ml, Glycerophosphate 10 mM and Dexamethasone 0.1 µM or adipogenic media consisting of DMEM growth medium supplemented with 3-isobutyl-1-methyl-xanthine (IBMX) 0.5 mM, indomethacin 60 µM and Hydrocortisone 0.5 µM. Media was changed every 3 days until end-point assay. All differentiation experiments were finished after 15 days.

Differentiation media were used only in differentiation control samples and differentiation induced experiments.

Immunohistochemistry Assays

After culture, cells were washed in DPBS and fixed in a 10% formalin solution (Sigma-Aldrich) at 4° C. for 30 min. Samples were then rinsed with DPBS and maintained in a permeabilizing buffer (103 g/L sucrose, 2.92 g/L NaCl, 0.6 g/L $MgCl_2$, 4.76 g/L HEPES buffer, 5 mL/L Triton X-100, pH 7.2) at room temperature for 5 min. Afterwards, samples were incubated with primary antibody in blocking buffer 1% BSA/DPBS at room temperature for 1 h; The samples were then rinsed twice in 0.5% Tween 20/DPBS and incubated with the secondary antibody and BODIPY FL phallacidin (Invitrogen) 1:100 at room temperature for 1 h. Finally, samples were washed twice in 0.5% Tween 20/DPBS before mounting with Vectashield containing DAPI (Vector Laboratories) and observed under an epifluorescence microscope (Nikon Eclipse 80i).

For cell adhesion studies monoclonal primary mouse antibodies diluted 1:400 against vinculin (Sigma-Aldrich), talin (Sigma-Aldrich) and tensin (abcam) and $Cy^3$ conjugated secondary antibody (Jackson Immunoresearch) diluted 1:200 were used to detect focal adhesions. For evaluation of contractility anti phospho myosin light chain antibody (Cell signalling) diluted 1:200 and $Cy^3$ conjugated secondary antibody (Jackson Immunoresearch) diluted 1:200 were used. For experiments including contractility inhibitors, Y-27632 or blebbistatin was added to culture medium at different concentrations (10 and 20 µM) after 2 h of culture.

For evaluation of differentiation, several specific markers were used. Osteogenic differentiation was assessed using Runx2 (abcam) and osteopontin (Santa cruz Biotechnology) dilution 1:100 as primary antibodies. $Cy^3$ (Jackson Immunoresearch) and Alexa Fluor 488 (Invitrogen) diluted 1:200 were used as secondary antibodies.

Adipogenic differentiation was detected by observation of lipid levels that were qualitatively assessed by a standard Oil RedO staining protocol. Briefly, cells were washed in PBS, fixed with 10% formalin for 30 min and washed in diH2O.

Immediately before use, 30 ml of a stock solution of Oil Red O (3 mg/ml in 99% isopropanol) was mixed with 20 ml diH2O, filtered and applied for 10 min to cells pre-equilibrated with 60% isopropanol.

Maintenance of stemness was evaluated by detection of specific mMSC marker Sca1 (abcam) diluted 1:200 as primary antibody and Alexa Fluor 488 antibody (Jackson Immunoresearch, diluted 1:200) as secondary antibody.

Gene expression analysis by quantitative real time PCR

Total RNA was extracted from MC3T3 cells cultured for 3 or 15 days under different experimental conditions using RNeasy micro kit (Qiagen) according to the manufacturer's protocol. RNA quantity and integrity was measured with a NanoDrop 1000 (ThermoScientific). Then, 150 ng of RNA were reverse transcribed using the Superscript Ill reverse transcriptase (Invitrogen) and oligo dT primer (Invitrogen). Real-time qPCR was carried out using the Sybr select master mix and 7500 Real Time PCR system from Applied Biosystems. The reactions were run in triplicate for both technical and biological replicas. The primers used for amplification were designed based on sequences found in the GenBank database and included: Runx2 (NM_001 146038.1, Forward: 5"-TGA GAG TAG GTG TCC CGC CT-3' SEQ ID NO:7, Reverse: 5'-TGT GGA TTA AAA GGA CTT GGT GC-3' SEQ ID NO:8) and Osteopontin (NM 001204201.1, Forward: 5"-ITT GCC TGT TTG GCA TTG C-3' SEQ ID NO:9, Reverse: 5"-TGG GTG CAG GCT GTA AAG CT-3' SEQ ID NO:10) for osteogenic differentiation. PPARγ2 (NM_001127330.1, Forward: 5'-AGC AAA GAG GTG GCC ATC C-3' SEQ ID NO:11, Reverse: 5'-CTT GCA CGG CTT CTA CG-3' SEQ ID NO:12) and LPL (NM_008509.2, Forward: 5'-TGC CCT AAG GAC CCC TGA A-3'SEQ ID N0:13, Reverse: 5"-CAG TTA GAC ACA GAG TCT GC-3' SEQ ID NO:14) were used for adipogenic differentiation. Sca1 (NM_001271416.1, Forward: 5"-GAC CCT GGA GGC ACA CAG CC-3'SEQ ID NO:15, Reverse: 5"-CAT GTG GGA ACA TTG CAG GAC CCC-3' SEQ ID NO:16) and CD29 (Forward: 5"-GGA GGA ATG TAA CAC GAC TG-3' SEQ ID NO:17, Reverse: 5"-TGC CCA CTG CTG ACT TAG GAA TC-3' SEQ ID NO:18) were used for assessment of maintenance of sternness.

The fractional cycle number at which fluorescence passed the threshold ($C_t$ values) was used for quantification using the comparative $C_t$ method. Sample values were normalized to the threshold value of housekeeping gene GAPDH: $\Delta C_t = C_t(\text{experiments}) - C_t(\text{GAPDH})$. The $C_t$ value of the control (glass substrate coated with Collagen I) was used as a reference. $\Delta\Delta C_T = C_T(\text{experiment}) - \Delta C_T(\text{control})$. Relative mRNA expression was calculated by the following equation: fold change=$2^{-\Delta\Delta C_T}$ FAK and pFAK Detection and Quantification For FAK assays cells were cultured under serum-free conditions in order to reduce background signal. Cells were then seeded on FN-coated materials in serum-free medium. After 3 h of culture, cells were lysed with RIPA buffer (Tris-HCl 50 mM, 1% Nonidet P-40, 0.25% Na deoxycholate, NaCl 150 mM, EDTA 1 mM) containing protease inhibitor cocktail tablets (Roche). Proteins were concentrated using Microcon YM-30 Centrifugal Filter devices (Millipore) as the manufacturer described. To determine FAK protein expression and its phosphorylated form (pFAK), concentrated samples were subjected to 7% SDS-PAGE gel electrophoresis. Proteins were transferred to a positively charged PVDF membrane (GE Healthcare) using a semidry transfer cell system (Biorad) and blocked by immersion in 5% semi-skimmed milk in PBS for 30 min at room temperature. The blot was incubated with anti-FAK (abcam, 400 ng/mL) and anti-pFAK (abcam, 1 mg/mL) in PBS containing 0.1% Tween 20 and 2% semi-skimmed milk. After several washes with PBS/0.1% Tween 20, the blot was incubated in horseradish peroxidase-conjugated antibody (GE Healthcare) diluted 1:25000 for FAK and 1:10000 for pFAK in PBS containing 0.1% Tween 20 and 2% semi-skimmed milk for 1 hour at room temperature. Supersignal West Femto Maximum Sensitivity Substrate (Pierce) was used before X-ray exposition.

Image Analysis

To analyse focal adhesions, vinculin images were segmented by ImageJ, using Trainable Weka Segmentation plugin to create a binary mask. After segmentation, focal adhesion size and number were determined using different commands of the same software. Values of focal adhesion size frequency were obtained using GraphPad Prism 6.0. taking a bin width of 0.2 μm.

Cell morphology was analysed by calculation of different parameters using ImageJ software. Cell spreading area and roundness ($4 \times \text{area}/\pi \times [\text{major axis}]^2$) were calculated by evaluation of at least 40 cells for each condition.

Western blot bands pixel density was quantified using ImageJ software.

Statistical Analysis

All experiments were performed at least three times, unless otherwise noted. Data are reported as mean±standard error. Results were analyzed by one-way ANOVA using SYSTAT 8.0 (SPSS). If treatment level differences were determined to be significant, pair-wise comparisons were performed using a Tukey post hoc test. A 95% confidence level was considered to be significant.

Results and Discussion

Mesenchymal stem cells (MSCs) are capable of self-renewal and multi-lineage differentiation—classically into osteoblasts, adipocytes, chondrocytes and fibroblasts[1,2]. Multipotent cells remain in their niche as slow proliferating, metabolically quiescent cells in order to maintain multipotency. When using MSCs for regenerative medicine, it is important to obtain a sufficient number of cells that maintain pluripotency without compromising MSC senescence[3,4].

Material systems that mimic the natural niche environment of MSCs may offer an alternative to the use of complex cocktails of soluble factors used in the culture media. Previous studies show that the cell/material interface plays an essential role on MSC function and differentiation, encompassing promising approaches to manipulate differentiation of stem cells ranging from chemistry[5,6,7], surface modifications[8,9], topography[10,11,12], stiffness[13,14] and even dynamic material properties such as stress relaxation[15].

While we are starting to identify the range of materials properties that can be used to drive stem cell differentiation, there is much left to discover and understand. In addition, cells don't feel the surface of materials directly, but through an intermediate layer of adsorbed proteins. The conformation and distribution of this protein layer will determine integrin binding and the organisation of focal adhesions, which in turn will influence cell signalling and hence fate[16,17,18,19,20].

Acrylates are common biomaterials with tuneable physical properties[21]. In this work we used substrates that slightly differ in surface chemistry, varying only one methyl group in the side chain—poly(ethyl acrylate) (PEA) and poly(methyl acrylate) (PMA). Using this material system we have previously demonstrated that this subtle variation in surface chemistry modulates the conformation of adsorbed fibronectin (FN). Typically, FN adsorbs to synthetic materials in a globular morphology, as it does on PMA. However, on PEA, the FN molecules spontaneously organise into nanonetworks, a process that we have termed material-driven fibronectin fibrillogenesis[22,23,24]. We hypothesise that these FN nanonetworks assembled on PEA influence the behaviour of mesenchymal stem cells (MSCs). In this new report, we have investigated the role of FN nanonetworks on MSC adhesion, differentiation (osteogenic, adipogenic) and growth, by culturing cells in absence of differentiation factors.

We have used C3H10T1/2 cells, an established murine multipotent mesenchymal stem (mMSC) cell line from 14-to 17-day-old C3H whole mouse embryo[25]. These cells display fibroblastic morphology in high-density cell cultures and are functionally similar to mesenchymal stem cells. They have the potential to differentiate into mesodermal lineages (reticular, adipogenic, osteogenic and chondrogenic) under defined conditions, maintain a stable morphology in culture and present no tumorigenic activity[26].

Fibronectin Adsorption

Samples of PEA and PMA consisting of a vinyl backbone chain with side group —COO(CH2)$_x$H, with x=1 for PMA and x=2 for PEA were coated with 20 μg/ml FN. We had previously described the molecular distribution of FN on the different substrates by AFM[16]. FIG. 17 shows FN organised into nanonetworks upon adsorption on PEA and globular FN aggregates on PMA.

The surface density of adsorbed FN was previously determined by western blot analysis and the results showed similar values for both PEA and PMA, resulting in ~340 ng/cm$^2$ [22].

Cell Adhesion

We first examined the effect of FN organisation (fibrillar on PEA vs globular on PMA) on mMSC adhesion after 3 h of culture. It is important to highlight that cell adhesion was performed in the absence of serum in the media, thus initial cell/material contact occurs only via interaction with adsorbed FN on the material substrates. Cells were seeded at a low density (5,000 cells/cm$^2$) to maximize cell/material interactions and to minimise cell-cell contacts. FIG. 18-a shows cell morphology after staining actin fibres and vinculin within focal adhesion complexes (other focal adhesion proteins, e.g. Tensin and Talin, also show immunofluorescence staining, data not shown). Cells displayed prominent actin stress fibres terminating at well-developed focal adhesion sites. Cell area presented similar values for all surfaces (FIG. 18-b) although circularity of cells was slightly higher on PMA than PEA (FIG. 18-c).

Focal adhesion size distribution was quantified by image analysis on the different substrates (FIGS. 19-a and 19-b). We found significant differences for the total area occupied by focal adhesions (FIG. 19-a): PEA>PMA>control glass. The frequency distribution was similar on all surfaces, with a higher fraction of smaller plaques (1 or 2 μm$^2$) that decreased monotonically up to larger, 4 μm$^2$, plaques (FIG. 19-b). Immunofluorescence staining for other focal adhesion proteins, e.g. talin and tensin revealed similar trends (data not shown).

To gain insights into the initial signalling mechanism, we examined activation (phosphorylation) of Focal Adhesion Kinase (FAK) after 3 h of culture in absence of serum in medium. FAK localizes to focal adhesions and forms a main part of the adhesion signalling strata. FIG. 19-c shows expression of pFAK/FAK. Higher levels of pFAK were obtained on PEA compared with PMA and glass, revealing increased FAK activation from the FN nanonetworks assembled on PEA fitting nicely with the observation of increased adhesion area.

Cell Differentiation

We first evaluated the effect of FN assembly (globular on PMA vs nanonetworks on PEA) on mMSC differentiation using basal medium (B.M.) containing 10% FBS without any supplements or growth factors in it. Considering the range of stiffness of PEA and PMA used in our experiments (~1000-2000 kPa)[27], and the range of stiffness that cells are sensitive to (~1-40 kPa)[13], cells are unable to deform the underlying substrates that will be sensed simply as rigid substrates. We evaluated the phenotypical behaviour of mMSC during commitment along two different lineages: osteogenic and adipogenic, and also their ability to grow maintaining stemness.

We used cell seeding densities of 10,000 cells/cm$^2$ to promote osteogenesis and 30,000 cells/cm$^2$ to favour adipogenesis[28]. Immunofluorescence images were taken after 15 days of culture in order to analyse morphology of cells onto FN-coated materials (glass was used as positive control with differentiation medium, D.M.). FIG. 20 shows that mMSC grew to confluence and consistently displayed a spindle-like, fibroblastic morphology across FN-coated PEA and PMA surfaces, which suggests no spontaneous differentiation[28,29]. Cells on glass substrates (control using D.M.) presented a polygonal morphology typical of osteoblasts after an osteogenic induction (osteogenic differentiation medium, O.D.M.) period and a rounded shape due to the high content of vacuoles characteristic of adipocytes after adipogenic induction (adipogenic differentiation medium, A.D.M.)[30].

Further, we investigated specific markers of osteogenic differentiation (osteopontin (OPN) and Runt related transcription factor 2 (Runx2)) as well as Oil red O staining to assess adipogenic commitment. Immunofluorescence was done after 15 days of culture for OPN, while Runx2, an early expression transcription factor in osteogenenesis, was detected after 3 days of culture[31]. Oil Red O staining confirmed the presence of adipocytes after 15 days of culture. FIG. 21 shows representative images on the different substrates. Both mMSCs on FN-coated PEA and PMA (using B.M.) showed minimum levels of OPN compared with glass (using D.M., positive control of differentiation). In contrast Runx2 levels were similar between PMA and glass, whereas Runx2 levels were slightly higher on PEA. In respect to adipogenic markers, Oil red O staining only revealed lipid vacuoles that had developed fat droplets (FIG. 5, inset magnification) on the positive control of differentiation (glass+A.D.M). We also analysed other osteogenic markers such as osteocalcin (OCN) and integrin binding sialoprotein (IBSP) with similar results (PEA and PMA showing minimum levels of staining, data not shown).

Based on these results, we hypothesised that mMSCs cultured on FN-coated substrates maintained their self-renewal potential rather than differentiating into specific lineages. FIG. 21 shows high levels of Sca1 staining for PEA and PMA, a specific marker of undifferentiated murine mesenchymal cells[32,33].

These results suggest that FN-coated PEA and PMA promote maintenance of stemness rather than lineage commitment in the absence of soluble factors in media. Next, we evaluated their ability to sustain MSC differentiation under defined media conditions and also the self-renewal maintenance in longer-term cultures. To do this, we designed three different experimental conditions: i) mMSCs cultured for 15 days using differentiation media (to evaluate the potential of FN-coated PEA and PMA to support osteogenic/adipogenic commitment); ii) mMSCs cultured for 15 days under basal conditions and then stimulated to differentiate with differentiation media for another 15 days; and iii) mMSCs cultured for 30 days under basal conditions.

FIG. 22 shows representative images of different experimental conditions. Runx2 and OPN expression was detected at similar levels in cells on PEA, PMA and control Glass after 3 (Runx2) and 15 days (OPN) of stimulation with osteogenic medium (O.D.M). Likewise, Oil red O staining showed formation of lipid vacuoles containing fat droplets in all substrates after 15 days of stimulation with adipogenic medium (A.D.M.). These results show the ability of FN-coated substrates (PEA and PMA) to support efficient lineage commitment under differentiation conditions. However, when mMSC were cultured for 15 days under basal conditions (B.M.) and afterwards stimulated with osteogenic/adipogenic media (B.M.+O.D.M./A.D.M.), the capacity of FN-coated substrates to promote lineage commitment was particularly strong for cells cultured on FN nanonetworks on PEA, as revealed by the higher levels of osteoblastic differentiation (FIG. 22).

Furthermore, after 15 d and 30 d of culture in basal medium, PEA presented again higher levels of stemness markers (Sca 1) compared to PMA and Glass that showed minimal levels of expression (FIG. 22).

Analysis of Gene Expression

After this initial evaluation of results obtained for cell differentiation on the FN-coated substrates, we performed qPCR analysis of specific genes related to osteogenic or adipogenic commitment under basal conditions (B.M.). Runx2 and adipocyte peroxisome proliferation-activated receptor (PPARγ2) are transcription factors involved in osteogenic and adipogenic commitment respectively. As both transcripts/proteins are involved in early onset of lineage commitment, we first analysed their expression after 3 days of culture in B.M. FIG. 23-a (i) shows that Runx2 levels were higher in PEA while in PMA and control glass remain similar. In contrast, PPARγ2 levels were low both in PEA and PMA. Further qPCR analysis was performed after 15 days of culture. FIG. 23-a (ii) represents Runx2 and OPN as markers of osteogenesis whereas FIG. 23-a (iii) represents relative expression of PPARγ2 and lipoprotein lipase (LPL) as markers of adipogenesis. Expression levels of PPARγ2 and LPL were minimal in all substrates compared to the positive control for differentiation. OPN levels were also low and Runx2 levels were lower than that observed at 3 days; this is in agreement with previous immunofluorescence data (FIG. 21). We also analysed relative expression of stemness markers Sca 1 and CD29 under basal conditions. PEA presented the highest levels of Sca 1 and CD29 followed by PMA and then minimum expression levels for these markers was noted for the positive differentiation controls (FIG. 23-a (iv)). These results are consistent with data obtained in immunofluorescence images (FIG. 21 and FIG. 22).

We next used qPCR analysis to study expression of the osteogenic, adipogenic and stem cell-related genes for cells on the FN-coated substrates cultured for 15 days with 1) mMSCs under differentiation conditions (FIG. 23-b (i)); 2) mMSCs cultured for 15 days with basal media and then stimulated to commitment with differentiation media (FIG. 23-b (ii)); and finally evaluation of stemness after a 30 days of long-term culture in B.M. (FIG. 23-b (iii)).

FN-coated PEA and PMA substrates showed a similar potential to support induction of both osteogenic and adipogenic differentiation under defined media conditions compared to inducement on glass control (FIG. 23-b (i)). When mMSCs were cultured for 15 days prior to addition of defined medias, a trend of increased induction on PEA was noted (FIG. 23-b (ii)) in agreement with results obtained at protein level (FIG. 22). Note that only on PEA cells maintain their ability to differentiate into osteogenic and adipogenic lineages, whereas on PMA only the ability to undergo adipogenesis is maintained after 15 days of culture in B.M ((FIG. 23-b (ii)).

Importantly, high levels of stemness markers were only found in PEA after 30 days of culture (FIG. 23-b (iii)), in line with data previously obtained by immunofluorescence assays (FIG. 22).

Analysis of Contractility

Forces generated by cells regulate different processes including cell contraction and differentiation[34], and cell migration[35] via phosphorylation of the myosin light chain (MLC)[36]. We examined whether this contractility process was related to differentiation or self-renewal of mMSCs cultured on PEA and PMA. Immunofluorescence staining for phosphorylated MLC (pMLC) revealed co-localisation of pMLC coincident with the actin cytoskeleton in cells cultured on all substrates (data not shown). Cells were then cultured in the presence of pharmacological inhibitors that impair contractility. We used Y-27632 as specific inhibitor of Rho-kinase, and blebbistatin as specific inhibitor of myosin II activity[37,38]. Staining for pMLC was reduced in a dose-dependent manner (10 and 20 µM respectively) in the presence of these inhibitors in cells on the different substrates (data not shown).

The expression of osteogenic markers requires high cell contractility, as expected, inhibition of cell contractility (blebbistatin and Y-27632 at final concentrations of 20 µM) greatly reduced osteogenic marker expression from the MSCs on all substrates (FIG. 24).

Self-renewal markers were also studied and CD29 and Sca1 expression levels were strongly reduced regardless of the FN distribution on PEA and PMA (FIGS. 24-a and b), which suggests a role of material-activated cell contractility in stemness maintenance.

The application of materials science to modulate the cellular microenvironment and direct MSC fate will be fundamental to developing an understanding of stem cell function. Different attempts include cues such as topography[39] and stiffness[13] or chemistry[40]. While these studies demonstrate that material properties influence cell fate decisions, no examples so far have observed material-induced conditions that permit first MSC growth and then enhanced differentiation[12,14]. Here we show that FN-nanonetworks assembled on PEA promotes enhanced, prolonged maintenance of self-renewal and retention of functional multipotency when basal media is used. However, when defined medias, traditionally used to induce specific differentiations, enhanced levels of differentiation is noted; i.e. the cells were more sensitive to the defined medias when cultured on the FN nanonetworks.

It is well documented that cell-material interaction takes place through an intermediate layer of proteins adsorbed onto substrates. The amount of protein adsorbed and its conformation on materials depends of surface chemistry[40]. Proper conformation of adsorbed proteins directs integrin binding, focal adhesion assembly and cell differentiation[41,42,19]. We have previously reported the amount of FN adsorbed on PEA and PMA to be similar at ~340 ng/cm² afor both polymers[22]. However, FN distribution and conformation differ significantly with interconnected FN nanonetworks on PEA whereas globular aggregates appeared on PMA (FIG. 17)[16]. This new work demonstrates the critical nature of this protein interface in MSC functionality. The MSCs acted with far greater growth and differentiation potential when biomimetic FN networks rather than FN with globular morphology was used as the culture substrate.

Adhesion-derived tension is critical for several processes, including cell survival[43] and MSC differentiation[13,44]. In this work we first evaluated the role of FN nanonetworks in initial cell adhesion of mMSC and signalling. Focal adhesions are multiprotein associated complexes that act as a link between ECM and actin cytoskeleton. Their structure, composition and dynamics depend on the information received from the extracellular protein environment—in this case adsorbed FN in different confirmations. In fact, it has been found a direct correlation between their size and functionality. Classically, adipogenesis (small adhesions, low intracellular tension) and osteogenesis (large adhesions, high intracellular tension) as used as exemplars[5,6,45]. However, much less in understood about the MSC phenotype itself in terms of tension phenotype.

PEA, supporting fibrillogenesis, presented enhanced focal adhesion formation in terms of vinculin, talin and tensin expression (FIG. 18-a). Quantification of focal adhesion surface area showed significantly higher values for MSCs on the fibrillar networks although the size distribution of totality of focal adhesions remained similar for all substrates (FIGS. 19-a and 19-b). This suggests that the FN network assembled on PEA enhances focal adhesion number but not size.

FAK, a downstream effector of integrin ligation to the extracellular environment[5,6] such as FN, can simultaneously activate multiple signalling pathways that regulate cell migration, survival, proliferation and differentiation[46]. Activation of FAK is produced after phosphorylation at Y-397, the autophosphorylation site and a binding point for Src and PI-3 Kinases[47]. The pFAK/FAK ratio was significantly higher in PEA than on PMA or glass (FIG. 19-c), which correlates to the unfolding of FN during fibrillogenesis and subsequent availability of critical domains for cell adhesion such as RGD and PHSRN as we, and others[48], have described before[23,49].

These data show that MSCs on PEA are adhesion primed to increase responsiveness, but do not reveal if tension itself is important in stem cell growth. Addition of blebbistatin or Y-27632 both reduced ability to commit to osteogenic differentiation (as expected) and ability to retain the MSC phenotype showing that MSC growth requires intracellular tension. This ties in with literature on human MSCs showing that while adipogenesis requires almost no intracellular tension, the MSC growth requires slightly reduced tension than fibroblastic differentiation and much lower tension than osteobalstic differentiation[50,51].

This work shows, for the first time, that in order to fully potentiate the ability of biomaterials to control MSC growth and differentiation (as in the niche), full attention needs to be given to the intermediate protein layer. We hypothesise that biology has evolved to use certain protein conformations to achieve a full range of cell control. Thus, when we use a biomimetic protein confirmation, we achieve a significantly more dynamic range of MSC growth and differentiation ability. FN nanonetworks on PEA sustain stem cell growth maintaining stemness and then MSCs can be induced to differentiation on the same substrate by changing the external conditions.

References for Material-Driven FN Assembly Promotes Maintenance of Mesenchymal Stem Cell Phenotypes 1. Control of osteoblast function and regulation of bone mass. at <http://www.nature/com/nature/journal/v423/n6937/pdf/nature01660.pdf>
2. Gregory, C. A., Ylostalo, J. & Prockop, D. J. Adult bone marrow stem/progenitor cells (MSCs) are preconditioned by microenvironmental 'niches' in culture: a two-stage hypothesis for regulation of MSC fate. Sci. STKE 2005, pe37 (2005).
3. Replicative Senescence of Mesenchymal Stem Cells: A Continuous and Organized Process. at <http://www.plosone.org/article/fetchObject.action?uri=info:doi/10.1371/journal.pone.0002213&representation=PDF>
4. Long-term In vitro Expansion Alters the Biology of Adult Mesenchymal Stem Cells. at <http://cancerres.aacrjournals.org/content/68/11/4229.full.pdf>
5. Cell Shape, Cytoskeletal Tension, and RhoA Regulate Stem Cell Lineage Commitment. at <https://www.princeton.edu/~cmngroup/8_McBeath_DevCell_2004.pdf>
6. Geometric cues for directing the differentiation of mesenchymal stem cells. at <file:///D:/PRT-back up 191214/biomateriales/proyectos en los que participo/mMSCs/células madre mesenquimales/2010_PNAS_Kilian-Mrksich_GeometricCuesDirectingDifferentiationMSC.pdf>
7. Mechanical memory and dosing influence stem cell fate. at <http://www.nature.com/nmat/journal/v13/n6/pdf/nmat3889.pdf>
8. The guidance of human mesenchymal stem cell differentiation in vitro by controlled modifications to the cell substrate. at <http://ac.els-cdn.com/S0142961206004340/1-s2.0-S0142961206004340-main.pdf?_tid=198eb024-9d91-11e4-a841-00000aab0f02&acdnat=1421420905_c677cd0bb6cbf162e0061f7357e8bc54>
9. Small functional groups for controlled differentiation of hydrogel-encapsulated human mesenchymal stem cells. at <http://www.nature.com/nmat/journal/v7/n10/pdf/nmat2269.pdf>
10. Dalby, M. J., Gadegaard, N., Curtis, A. S. G. & Oreffo, R. O. C. Nanotopographical control of human osteoprogenitor differentiation. Curr. Stem Cell Res. Ther. 2, 129-38 (2007).
11. Stem cell fate dictated solely by altered nanotube dimension. at <file:///D:/PRT-back up 191214/biomateriales/proyectos en los que participo/mMSCs/células madre mesenquimales/2009_PNAS_Oh-Jin_StemCellFateDictatedSolelybyNanotubeDimension.pdf>
12. McMurray, R. J. et al. Nanoscale surfaces for the long-term maintenance of mesenchymal stem cell phenotype and multipotency. Nat. Mater. 10, 637-644 (2011).
13. Engler, A. J., Sen, S., Sweeney, H. L. & Discher, D. E. Matrix elasticity directs stem cell lineage specification. Cell 126, 677-89 (2006).
14. Gilbert, P. M. et al. Substrate elasticity regulates skeletal muscle stem cell self-renewal in culture. Science 329, 1078-81 (2010).
15. Chaudhuri, O. et al. Hydrogels with tunable stress relaxation regulate stem cell fate and activity. Nat. Mater. (2015). doi:10.1038/nmat4489
16. Role of material-driven fibronectin fibrillogenesis in cell differentiation. at <file:///D:/PRT-back up 191214/biomateriales/proyectos en los que participo/mMSCs/manuscript/bibliografia/células madre mesenquimales/2011_Biomaterials_Salmeron-Sanchez-Garcia_RoleMaterialDrivenFNFibrillogenesis.pdf>
17. Ballester-Beltrán, J. et al. Effect of topological cues on material-driven fibronectin fibrillogenesis and cell differentiation. J. Mater. Sci. Mater. Med. 23, 195-204 (2012).
18. Keselowsky, B. G., Collard, D. M. & García, A. J. Surface chemistry modulates focal adhesion composition and signaling through changes in integrin binding. Biomaterials 25, 5947-5954 (2004).

19. Integrin binding specificity regulates biomaterial surface chemistry effects on cell differentiation. at <file:///D:/PRT-back up 191214/biomateriales/proyectos en los que participo/mMSCs/manuscript/bibliografia/células madre mesenquimales/2005_PNAS_Keselowsky-Garc5953-7.pdf>
20. Michael, K. E., Dumbauld, D. W., Burns, K. L., Hanks, S. K. & García, A. J. Focal adhesion kinase modulates cell adhesion strengthening via integrin activation. *Mol. Biol. Cell* 20, 2508-19 (2009).
21. Combinatorial development of biomaterials for clonal growth of human pluripotent stem cells. at <http://www.nature.com/nmat/journal/v9/n9/pdf/nmat2812.pdf>
22. Rico, P. et al. Substrate-induced assembly of fibronectin into networks: influence of surface chemistry and effect on osteoblast adhesion. *Tissue Eng. Part A* 15, 3271-3281 (2009).
23. Rico, P., González-García, C., Petrie, T. A., García, A. J. & Salmerón-Sánchez, M. Molecular assembly and biological activity of a recombinant fragment of fibronectin (FNIII7-10) on poly(ethyl acrylate). *Colloids Surfaces B Biointerfaces* 78, 310-316 (2010).
24. Guerra, N. B. et al. Subtle variations in polymer chemistry modulate substrate stiffness and fibronectin activity. *Soft Matter* 6, 4748 (2010).
25. Reznikoff, C. a, Brankow, D. W. & Heidelberger, C. Establishment and Characterization of a Cloned Line of C3H Mouse Embryo Cells Sensitive to Postconfluence Inhibition of Division Establishment and Characterization of a Cloned Line of C3H Mouse Embryo Cells Sensitive to Postconfluence Inhibition of. 3231-3238 (1973).
26. 1OT1/2 Cells: An In Vitro Model for Molecular Genetic Analysis of Mesodermal Determination and Differentiation. at <file:///D:/PRT-back up 191214/biomateriales/proyectos en los que participo/mMSCs/células madre mesenquimales/mouse MSC/1989_EnvHealthProsp_Pinney-Emerson_10T1CellsAnInVitroModelForMolecularGeneticAnalysis.pdf>
27. González-García, C., Moratal, D., Oreffo, R. O. C., Dalby, M. J. & Salmerón-Sánchez, M. Surface mobility regulates skeletal stem cell differentiation. *Integr. Biol. (Camb)*. 4, 531-9 (2012).
28. Multilineage Potential of Adult Human Mesenchymal Stem Cells. at <http://www.sciencemag.org/content/284/5411/143.full.pdf>
29. Dominici, M. et al. Minimal criteria for defining multipotent mesenchymal stromal cells. The International Society for Cellular Therapy position statement. *Cytotherapy* 8, 315-7 (2006).
30. Chamberlain, G., Fox, J., Ashton, B. & Middleton, J. Concise review: mesenchymal stem cells: their phenotype, differentiation capacity, immunological features, and potential for homing. *Stem Cells* 25, 2739-49 (2007).
31. Genes and Proteins Involved in the Regulation of Osteogenesis. at <http://www.oulu.fi/spareparts/ebook_topics_in_t_e_vol³/abstracts/kirkham_chapter_01.pdf>
32. Kim, R. J. et al. Ras activation contributes to the maintenance and expansion of Sca-1pos cells in a mouse model of breast cancer. *Cancer Lett.* 287, 172-181 (2010).
33. Satelli, A. & Li, S. Vimentin in cancer and its potential as a molecular target for cancer therapy. *Cell. Mol. Life Sci.* 68, 3033-46 (2011).
34. Griffin, M. a, Sen, S., Sweeney, H. L. & Discher, D. E. Adhesion-contractile balance in myocyte differentiation. *J. Cell Sci.* 117, 5855-63 (2004).
35. Finding the weakest link—exploring integrin-mediated mechanical molecular pathways. at <http://jcs.biologists.org/content/125/13/3025.full.pdf>
36. Kaibuchi, K., Kuroda, S. & Amano, M. Regulation of the cytoskeleton and cell adhesion by the Rho family GTPases in mammalian cells. *Annu. Rev. Biochem.* 459-486 (1999).
37. Narumiya, S., Ishizaki, T. & Ufhata, M. *Regulators and Effectors of Small GTPases—Part D: Rho Family. Methods Enzymol.* 325, (Elsevier, 2000).
38. Mechanism of Blebbistatin Inhibition of Myosin II*. at <file:///D:/PRT-back up 191214/biomateriales/proyectos en los que participo/mMSCs/manuscript/bibliografia/células madre mesenquimales/2004_JBiolChem_Kovacs-Sellers_MechanismBlebbistatinInhibition.pdf>
39. The control of human mesenchymal cell differentiation using nanoscale symmetry and disorder. at <http://www-.nature.com/nmat/journal/v6/n12/pdf/nmat2013.pdf>
40. Phillips, J. E., Petrie, T. a, Creighton, F. P. & Garcia, a J. Human mesenchymal stem cell differentiation on self-assembled monolayers presenting different surface chemistries. *Acta Biomater* 6, 12-20 (2010).
41. Keselowsky, B. G., Collard, D. M. & García, A. J. Surface chemistry modulates fibronectin conformation and directs integrin binding and specificity to control cell adhesion. *J. Biomed. Mater. Res. A* 66, 247-59 (2003).
42. Surface chemistry modulates focal adhesion composition and signaling through changes in integrin binding. at <http://ac.els-cdn.com/S0142961204001176/1-s2.0-S0142961204001176-main.pdf?tid=600abcd4-bbf8-11e4-9706-00000aab0f6b&acdnat=1424763796_2efe6883c1bf6645139f3c1ba1e254d3>
43. Geometric Control of Cell Life and Death. at <http://www.sciencemag.org/content/276/5317/1425.full.pdf>
44. Growth factors, matrices, and forces combine and control stem cells. at <file:///D:/PRT-back up 191214/biomateriales/proyectos en los que participo/mMSCs/células madre mesenquimales/2009_Science_Discher-Zandstra_GFMatricesAndForcesCombineAndControlSC.pdf>
45. Geiger, B., Bershadsky, A., Pankov, R., Yamada, K. M. & Correspondence, B. G. Transmembrane extracellular matrix—cytoskeleton crosstalk. *Nat. Rev. |Molecular Cell Biol.* 2, 793-805 (2001).
46. Mitra, S. K., Hanson, D. A. & Schlaepfer, D. D. Focal adhesion kinase: in command and control of cell motility. *Nat. Rev. Mol. Cell Biol.* 6, 56-68 (2005).
47. Autophosphorylation of the Focal Adhesion Kinase, pp125FAK Directs SH2-Dependent Binding of pp60src. at <file:///D:/PRT-back up 191214/biomateriales/proyectos en los que participo/mMSCs/manuscript/bibliografia/células madre mesenquimales/1994-Mol. Cell. Biol_Schaller-Parsons_AutophosphorylationFAKDirectsSH2Binding.pdf>
48. Lee, S. T. et al. Engineering integrin signaling for promoting embryonic stem cell self-renewal in a precisely defined niche. *Biomaterials* 31, 1219-1226 (2010).
49. A Material-Based Platform to Modulate Fibronectin Activity and Focal Adhesion Assembly. at <file:///D:/PRT-back up 191214/biomateriales/proyectos en los que participo/mMSCs/manuscript/bibliografia/células madre mesenquimales/2014_BioResOpenAccess_Vanterpool-Salmeron-Sanchez_MaterialBasedPlatformModulateFNActivity.pdf>
50. Harnessing nanotopography and integrin-matrix interactions to influence stem cell fate. at <http://www.nature.com/nmat/journal/v13/n6/pdf/nmat3980.pdf>

51. Tsimbouri, P. M. et al. Using nanotopography and metabolomics to identify biochemical effectors of multipotency. *ACS Nano* 6, 10239-10249 (2012).

While the invention has been described in conjunction with the exemplary embodiments described above, many equivalent modifications and variations will be apparent to those skilled in the art when given this disclosure. Accordingly, the exemplary embodiments of the invention set forth are considered to be illustrative and not limiting. Various changes to the described embodiments may be made without departing from the spirit and scope of the invention. All documents cited herein are expressly incorporated by reference.

General References

1. Dave P C, Dingal P, Discher D E (2014) Combining insoluble and soluble factors to steer stem cell fate. *Nat Mater* 13(6):532-537.
2. Martino M M, Hubbell J A (2010) The 12th-14th type III repeats of fibronectin function as a highly promiscuous growth factor-binding domain. *FASEB J* 24(12):4711-4721.
3. Martino M M, Tortelli F, Mochizuki M, Traub S, Ben-David D, Kuhn G A, Müller R, Livne E, Eming S A, Hubbell J A (2011) Engineering the growth factor microenvironment with fibronectin domains to promote wound and bone tissue healing. *Sci Transl Med* 3:100ra89.
4. Martino M M, Briquez P S, Ranga A, Lutolf M P, Hubbell J A (2013) Heparin-binding domain of fibrin(ogen) binds growth factors and promotes tissue repair when incorporated within a synthetic matrix. *Proc Natl Acad Sci USA* 110(12):4563-4568.
5. Martino M M, Briquez P S, Esra G, Tortelli F, Kilarski W W, Metzger S, Rice J J, Kuhn G A, Müller R, Swartz M A, Hubbell J A (2014) Growth factors engineered for super-affinity to the extracellular matrix enhance tissue healing. *Science* 343(6173):885-888.
6. Lo K W, Ulery B D, Ashe K M, Laurencin C T (2012) Studies of bone morphogenetic protein-based surgical repair. *Adv Drug Deliv* 64912):1277-1291.
7. Woo E J (2012) Recombinant human bone morphogenetic protein-2: adverse events reported to the manufacturer and user facility device experience database. *Spine J* 12(10):894-899.
8. Panel Executive Summary for P050036 Medtronic's AMPLIFY™ rhBMP-2 Matrix. U S. Food and Drug Administration, Silver Spring, MD, 2010.
9. Vo T N, Kasper F K, Mikos A G (2012) Strategies for controlled delivery of growth factors and cells for bone regeneration. *Adv Drug Del Rev* 64(12):1292-1309.
10. Lutolf M P, Hubbell J A (2005) Synthetic biomaterials as instructive extracellular microenvironments for morphogenesis in tissue engineering. *Nat Biotechnol* 23(1):47-55.
11. Wylie R G, Ahsan S, Aizawa Y, Maxwell K L, Morshead C M, Shoichet M S (2011) Spatially controlled simultaneous patterning of multiple growth factors in three-dimensional hydrogels. *Nat Mater* 10(10):799-806.
12. Salmeron-Sanchez M, Rico P, Moratal D, Lee T T, Schwarzbauer J E, García A J (2011) Role of material-driven fibronectin fibrillogenesis in cell differentiation. *Biomaterials* 32(8):2099-2105.
13. Comoglio P M, Boccaccio C, Trusolino L (2003) Interactions between growth factor receptors and adhesion molecules: Breaking the rules. *Curr Opin Cell Biol* 15(5): 565-571.
14. Pankov R, Yamada K M (2002) Fibronectin at a glance. *J Cell Sci* 115(Pt20):3861-3863.
15. Kanchanawong P, Shtengel G, Pasapera A M, Ramko E B, Davidson M W, Hess H F, Waterman C M (2010) Nanoscale architecture of integrin-based cell adhesions. *Nature* 468(7323):580-584.
16. Gugutkov D, Gonzalez-Garcia C, Hernandez J C R, Altankov G, Salmeron-Sanchez M (2009) Biological activity of the substrate-induced fibronectin network: insight into the third dimension through electrospun fibers. *Langmuir* 25(18):10893-10900.
17. Llopis-Hernandez V, Rico P, Moratal D, Altankov G, Salmeron-Sanchez M (2013) Role of material-driven fibronectin fibrillogenesis in protein remodelling. *BioRes Open Access* 2(5):364-373.
18. Klotzsch E, Smith M L, Kubow K E, Muntwyler S, Little W C, Beyeler F, Gourdon D, Nelson B J, Vogel V (2009) Fibronectin forms the most extensible biological fibers displaying switchable force-exposed cryptic binding sites. *Proc Nat Acad Sci USA* 106(43):18267-72.
19. Müller C, Stamov D R, Werner C, Pompe T (2012) Nanoscale characterization of cell receptors and binding sites on cell-derived extracellular matrices. *Ultramicroscopy* 118:44-52.
20. Hernandez J C, Salmeron-Sanchez M, Soria J M, Ribelles J L G, Pradas M M (2007) Substrate chemistry-dependent conformations of single laminin molecules on polymer surfaces are revealed by the phase signal of atomic force microscopy. *Biophys J* 93(1), 202-207.
21. Fu L, Tang T, Miao Y, Zhang S, Qu Z, Dai K (2008) Stimulation of osteogenic differentiation and inhibition of adipogenic differentiation in bone marrow stromal cells by alendronate via ERK and JNK activation. *Bone* 43(1): 40-47.
22. Greenblatt M B, Shim J H, Zou W, Sitara D, Schweitzer M, Hu D, Lotinun S, Sano Y, Baron R, Park J M, Arthur S, Xie M, Schneider M D, Zhai B, Gygi S, Davis R, Glimcher L H (2010) The p38 MAPK pathway is essential for skeletogenesis and bone homeostasis in mice. *J Clin Invest* 120(7):2457-2473.
23. Phimphilai M, Zhao Z, Boules H, Roca H, Franceschi R T (2006) BMP signaling is required for RUNX2-dependent induction of the osteoblast phenotype. *J Bone Miner Res* 21(4):637-646.
24. Benoit D S, Schwartz M P, Durney A R, Anseth K S (2008) Small functional groups for controlled differentiation of hydrogel-encapsulated human mesenchymal stem cells. *Nat Mater* 7(10):816-823.
25. Engler A J, Sen S, Sweeney H L, Discher D E (2006) Matrix elasticity directs stem cell lineage specification. *Cell* 126(4):677-689.
26. Huebsch N, Arany P R, Mao A S, Shvartsman D, Ali O A, Bencherif S A, Rivera-Feliciano J, Mooney D J (2010) Harnessing traction-mediated manipulation of the cell/matrix interface to control stem-cell fate. *Nat Mater* 9(6):518-526.
27. Trappmann B, Gautrot J E, Connelly J T, Strange D G, Li Y, Oyen M L, Cohen Stuart M A, Boehm H, Li B, Vogel V, Spatz J P, Watt F M, Huck W T (2012) Extracellular-matrix tethering regulates stem-cell fate. *Nat Mater* 11, 642-649.
28. Wen J H, Vincent L G, Fuhrmann A, Choi Y S, Hribar K C, Taylor-Weiner H, Chen S, Engler A J (2014) Interplay of matrix stiffness and protein tethering in stem cell differentiation. *Nat Mater* 13(10):979-987.
29. McMurray R J, Gadegaard N, Tsimbouri P M, Burgess K V, McNamara L E, Tare, R, Murawski K, Kingham E, Oreffo, R O, Dalby M J (2011) Nanoscale surfaces for the long-term maintenance of mesenchymal stem cell phenotype and multipotency. *Nat Mater* 10(8):637-644.

30. Dalby M J, Gadegaard N, Tare R, Andar A, Riehle M O, Herzyk P, Wilkinson C D, Oreffo R O (2007) The control of human mesenchymal cell differentiation using nanoscale symmetry and disorder. *Nat Mater* 6(12):997-1003.

31. Baneyx G, Baugh L, Vogel, V. Coexisting conformations of fibronectin in cell culture imaged using fluorescence resonance energy transfer (2001) *Proc Natl Acad Sci USA* 98(25):14464-14468.

33. Keselowsky B G, Collard D M, García A J (2005) Integrin binding specificity regulates biomaterial surface chemistry effects on cell differentiation. *Proc Natl Acad Sci USA* 102(17):5953-5957.

34. Watt F M, Hogan B L (2000) Out of Eden: stem cells and their niches. *Science* 287(5457):1427-1430.

35. Cantini, M, Rico P, Moratal D, Salmeron-Sanchez M (2012) Controlled wettability, same chemistry: biological activity of plasma-polymerized coatings. *Soft Matter* 8:5575-5584.

36. González-García C, Moratal D, Oreffo R O, Dalby M J, Salmerón-Sánchez M (2012) Surface mobility regulates skeletal stem cell differentiation. Integr Biol (Camb) 4(5):531-539.

37. Geiger B, Bershadsky A, Pankov R, Yamada K M (2001) Transmembrane extracellular matrix-cytoskeleton crosstalk. *Nat Rev Mol Cell Bio* 2, 793-805

38. Ulmer J, Geiger B, Spatz J (2008) Force-induced fibronectin fibrillogenesis in vitro. *Soft Matter* 4, 1998-2007.

39. Pompe T, Renner L, Werner C (2005) Nanoscale features of fibronectin fibrillogenesis depend on protein-substrate interaction and cytoskeleton structure. *Biophys J* 88, 527-534.

40. Olsson A K, Dimberg A, Kreuger J, Claesson-Welsh L. VEGF receptor signalling—in control of vascular function. Nature Reviews Molecular Cell Biology. 2006; 7:359-71.

41. Stratman A N, Davis M J, Davis G E. VEGF and FGF prime vascular tube morphogenesis and sprouting directed by hematopoietic stem cell cytokines. Blood. 2011; 117:3709-19.

42. Hallmann R, Horn N, Selg M, Wendler O, Pausch F, Sorokin L M. Expression and function of laminins in the embryonic and mature vasculature. Physiological Reviews. 2005; 85:979-1000.

43. Moulton K S, Olsen B R, Sonn S, Fukai N, Zurakowski D, Zeng X K. Loss of collagen XVIII enhances neovascularization and vascular permeability in atherosclerosis. Circulation. 2004; 110:1330-6.

44. Rice J J, Martino M M, De Laporte L, Tortelli F, Briquez P S, Hubbell J A. Engineering the Regenerative Microenvironment with Biomaterials. Advanced Healthcare Materials. 2013; 2:57-71.

45. Sacchi V, Mittermayr R, Hartinger J, Martino M M, Lorentz K M, Wolbank S, et al. Long-lasting fibrin matrices ensure stable and functional angiogenesis by highly tunable, sustained delivery of recombinant VEGF164. Proceedings of the National Academy of Sciences. 2014; 111:6952-7.

46. Traub S, Morgner J, Martino M M, Hoening S, Swartz M A, Wickstroem S A, et al. The promotion of endothelial cell attachment and spreading using FNIII10 fused to VEGF-A(165). Biomaterials. 2013; 34:5958-68.

47. Rico P, Rodriguez Hernandez J C, Moratal D, Altankov G, Monleon Pradas M, Salmeron-Sanchez M. Substrate-Induced Assembly of Fibronectin into Networks: Influence of Surface Chemistry and Effect on Osteoblast Adhesion. Tissue Engineering Part A. 2009; 15:3271-81.

48. Vanterpool F A, Cantini M, Seib F P, Salmeron-Sanchez M. A material-based platform to modulate fibronectin activity and focal adhesion assembly. BioResearch open access. 2014; 3:286-96.

49. Hanft J R, Pollak R A, Barbul A, van Gils C, Kwon P S, Gray S M, et al. Phase I trial on the safety of topical rhVEGF on chronic neuropathic diabetic foot ulcers. Journal of wound care. 2008; 17:30-2, 4-7.

50. Olea F D, Janavel G V, Cuniberti L, Yannarelli G, Meckert P C, Cors J, et al. Repeated, but not single, VEGF gene transfer affords protection against ischemic muscle lesions in rabbits with hindlimb ischemia. Gene Therapy. 2009; 16:716-23.

51. Chen T T, Luque A, Lee S, Anderson S M, Segura T, Iruela-Arispe M L. Anchorage of VEGF to the extracellular matrix conveys differential signaling responses to endothelial cells. Journal of Cell Biology. 2010; 188:595-609.

52. Hood J D, Frausto R, Kiosses W B, Schwartz M A, Cheresh D A. Differential alpha v integrin-mediated Ras-ERK signaling during two pathways of angiogenesis. Journal of Cell Biology. 2003; 162:933-43.

53. Takahashi T, Yamaguchi S, Chida K, Shibuya M. A single autophosphorylation site on KDR/Flk-1 is essential for VEGF-A-dependent activation of PLC-gamma and DNA synthesis in vascular endothelial cells. Embo Journal. 2001; 20:2768-78.

54. Eming S A, Hubbell J A. Extracellular matrix in angiogenesis: dynamic structures with translational potential. Experimental Dermatology. 2011; 20:605-13.

55. Fujio Y, Walsh K. Akt mediates cytoprotection of endothelial cells by vascular endothelial growth factor in an anchorage-dependent manner. Journal of Biological Chemistry. 1999; 274:16349-54.

56. Friedlander M, Brooks P C, Shaffer R W, Kincaid C M, Varner J A, Cheresh D A. DEFINITION OF 2 ANGIOGENIC PATHWAYS BY DISTINCT ALPHA(V) INTEGRINS. Science. 1995; 270:1500-2.

57. Avraamides C J, Garmy-Susini B, Varner J A. Integrins in angiogenesis and lymphangiogenesis. Nature Reviews Cancer. 2008; 8:604-17.

58. Soldi R, Mitola S, Strasly M, Defilippi P, Tarone G, Bussolino F. Role of alpha(v)beta(3) integrin in the activation of vascular endothelial growth factor receptor-2. Embo Journal. 1999; 18:882-92.

59. Rachit Agarwal, Andrés J. García. Biomaterial strategies for engineering implants for enhanced osseointegration and bone repair. Adv Drug Deliv Rev. 2015 Apr. 8. pii: S0169-409X(15)00048-4

60. Nyberg E1, Holmes C, Witham T, Grayson W L. Growth factor-eluting technologies for bone tissue engineering. Drug Deliv Transl Res. 2015 May 13. [Epub ahead of print]

61. Hastings et al. Adv Drug Deliv Rev. 2014 [in press]

62. A. Shekaran et al., Bone regeneration using an alpha 2 beta 1 integrin-specific hydrogel as a BMP-2 delivery vehicle. *Biomaterials* 35, 5453-5461 (2014).

The invention claimed is:

1. An implantable construct comprising:
   (a) a biocompatible substrate having a first surface, wherein the biocompatible substrate is selected from a synthetic polymer, a ceramic, a metal, an alloy and composites thereof;
   (b) a material surface comprising an alkyl acrylate polymer deposited on said first surface, wherein the alkyl acrylate polymer is capable of supporting the formation of a physiological fibrillar network of FN adsorbed on its surface;
   (c) fibronectin (FN) adsorbed on said material surface, wherein the FN forms a physiological fibrillar network of FN presenting colocalized growth factor binding domains and integrin binding domains; and
   (d) a growth factor (GF) adsorbed on said FN, wherein said growth factor is capable of binding $FNIII_{12-14}$.

2. The implantable construct of claim 1, wherein the FN and GF together provide a biologically active matrix assembled on the material surface.

3. The implantable construct of claim 1, wherein the construct is cell-free.

4. The implantable construct of claim 1, wherein the alkyl acrylate polymer is:
   (i) a member of the group of polymers having the formula $-(C-C-COO(CH_2)_xCH_3)r$, where x=1, 3, or 5;
   (ii) poly(ethyl acrylate) (PEA);
   (iii) a copolymer or blend comprising (1) an alkyl acrylate polymer capable of supporting the formation of a physiological fibrillar network of FN upon adsorption on its surface and (2) an alkyl acrylate polymer which alone is not capable of supporting the formation of a physiological fibrillar network of FN adsorbed on its surface, wherein the amount of (1) is about 50% or about 70%; or (iv) PEA/PMA (70%/30%) or PEA/PMA (50%:50%).

5. The implantable construct of claim 1, wherein the alkyl acrylate polymer surface is deposited as a thin (sub micron) layer surface on the substrate.

6. The implantable construct of claim 1, wherein the FN is isolated human FN from plasma.

7. The implantable construct of claim 1, wherein a growth factor is:
(i) BMP, VEGF, PDGF, TGF, FGF, IGF, HGF, BDNF or a neurotrophic GF; or
(ii) a recombinant human GF.

8. The implantable construct of claim 1, wherein the construct comprises one or more further ECM components selected from vitronectin (VN), collagen IV and laminin.

9. A method of promoting tissue regeneration or growth comprising locating an implantable construct of claim 1 at a site of injury or disease.

10. A method of promoting bone regeneration, optionally in treating critical size bone defects after trauma or cancer, or promoting bone growth, optionally for spinal fusion, comprising locating an implantable construct of claim 1 at a site of injury or disease.

11. A method of treating bone damage, optionally bone fracture or a critical size bone defect, comprising locating an implantable construct of claim 1 at a site of bone damage, optionally a site of bone fracture or a critical size bone defect.

12. A method of promoting vascularization in a subject in need of vascularization, optionally as a result of injury or disease, comprising locating an implantable construct of claim 1 at a site of tissue damage, optionally from injury or disease.

13. A method of wound healing or treating a wound, comprising locating an implantable construct of claim 1 at a site of tissue damage.

14. A method of preparing an implantable construct according to claim 1, comprising the steps of:
(a) depositing an alkyl acrylate polymer on a first surface of a biocompatible substrate to form a material surface wherein the biocompatible substrate is selected from a synthetic polymer, a ceramic, a metal, an alloy and composites thereof and further, wherein the alkyl acrylate polymer is capable of supporting the formation of a physiological fibrillar network of FN adsorbed on its surface; and
(b) applying fibronectin and a growth factor to said material surface to form a biologically active matrix, wherein said growth factor is capable of binding $FNIII_{12-14}$,
wherein the FN forms a physiological fibrillar network of FN presenting colocalized growth factor binding domains and integrin binding domains;
or the steps of:
(a) providing a biocompatible substrate having a first surface, wherein the biocompatible substrate is selected from a synthetic polymer, a ceramic, a metal, an alloy and composites thereof;
(b) depositing an alkyl acrylate polymer on said first surface to form a material surface; and
(c) applying fibronectin and a growth factor to said material surface to form a biologically active matrix, wherein the FN forms physiological fibrillar network of FN presenting colocalized growth factor binding domains and integrin binding domains.

15. A kit comprising an implantable construct of claim 1 and instructions for using the kit.

16. A kit for preparing an implantable construct according to claim 1 comprising:
(a) a biocompatible substrate having a first surface and a material surface comprising an alkyl acrylate polymer deposited on said first surface, wherein the biocompatible substrate is selected from a synthetic polymer, a ceramic, a metal, an alloy and composites thereof and further wherein the alkyl acrylate polymer is capable of supporting the formation of a physiological fibrillar network of FN adsorbed on its surface; and
(b) fibronectin (FN) and a growth factor (GF) capable of forming a biologically active matrix when applied to said material surface, wherein said growth factor is capable of binding $FNIII_{12-14}$; and
(c) instructions for adsorbing the fibronectin (FN) and a growth factor (GF) onto the material surface to form a biologically active matrix wherein the FN forms a physiological fibrillar network of FN presenting colocalized growth factor binding domains and integrin binding domains, thus forming an implantable construct.

17. A method of sustaining growth of stem cells or maintaining stem cells (maintaining stemness) comprising contacting a construct comprising:
a biocompatible substrate having a first surface, wherein the biocompatible substrate is selected from a synthetic polymer, a ceramic, a metal, an alloy and composites thereof, a material surface comprising an alkyl acrylate polymer deposited on said first surface, wherein the alkyl acrylate polymer is capable of supporting the formation of a physiological fibrillar network of FN adsorbed on its surface, fibronectin (FN) adsorbed on said material surface, wherein the FN forms a physiological fibrillar network of FN presenting colocalized growth factor binding domains and integrin binding domains, and a growth factor (GF) adsorbed on said FN, wherein said growth factor is capable of binding $FNIII_{12-14}$,
with a stem cell under conditions capable of supporting stem cell viability or growth.

18. The method of claim 17, wherein the construct is cell-free prior to contacting with the stem cell.

19. The method of claim 17, which is carried out in vitro.

20. A composition comprising a construct, said construct comprising a biocompatible substrate having a first surface, wherein the biocompatible substrate is selected from a synthetic polymer, a ceramic, a metal, an alloy and composites thereof, a material surface comprising an alkyl acrylate polymer deposited on said first surface, wherein the alkyl acrylate polymer is capable of supporting the formation of a physiological fibrillar network of FN adsorbed on its surface, fibronectin (FN) adsorbed on said material surface, wherein the FN forms a physiological fibrillar network of FN presenting colocalized growth factor binding domains and integrin binding domains, and a growth factor (GF) adsorbed on said FN, wherein said growth factor is capable of binding $FNIII_{12-14}$; and a murine mesenchymal stem cell (MSC).

21. The implantable construct of claim 7, wherein the PDGF is PDGF-BB.

22. The implantable construct of claim 7, wherein the TGF is TGF-β.

23. The implantable construct of claim 7, wherein the FGF is FGF2.

24. The implantable construct of claim 7, wherein the BMP is selected from BMP-2 and BMP-7.

25. The method of claim 17, wherein the stem cell is a mesenchymal stem cell (MSC).

26. The method of claim 18, wherein the stem cell is a mesenchymal stem cell (MSC).

27. The implantable construct of claim 1 wherein the synthetic polymer is selected from polyvinyl alcohol (PVA), oligo[poly[ethylene glycol) fumarate] (OPF), poly(glycolic acid) (PGA), poly(lactic acid) (PLA), poly(lactic-co-glycolic acid) (PLGA), polyether ether ketone (PEEK) and polycaprolactone (PCL).

28. The implantable construct of claim 1 wherein the ceramic is selected from hydroxyl carbonate apatite (HCA), calcium phosphate, hydroxyapatite (HA), tricalcium phosphate, bioactive glasses, alumina, zirconia, graphite and graphene.

29. The implantable construct of claim 1 wherein the metal or alloy is selected from stainless steel, cobalt-chromium, titanium and titanium alloys.

\* \* \* \* \*